(12) United States Patent
Funderburk et al.

(10) Patent No.: US 9,980,670 B2
(45) Date of Patent: May 29, 2018

(54) SENSOR INSERTER ASSEMBLY

(71) Applicant: Abbott Diabetes Care Inc., Alameda, CA (US)

(72) Inventors: Jeffery V. Funderburk, Stevenson Ranch, CA (US); Duane O. Yamasaki, El Cerrito, CA (US); Brian VanHiel, Marietta, GA (US); Stephen J. Flynn, Peachtree City, GA (US); Bradley D. Kelemen, Longmont, CO (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 1065 days.

(21) Appl. No.: 14/244,831

(22) Filed: Apr. 3, 2014

(65) Prior Publication Data

US 2014/0221800 A1     Aug. 7, 2014

Related U.S. Application Data

(63) Continuation of application No. 12/538,067, filed on Aug. 7, 2009, now abandoned, which is a
(Continued)

(51) Int. Cl.
*A61B 5/00* (2006.01)
*A61B 5/1473* (2006.01)
(Continued)

(52) U.S. Cl.
CPC .......... *A61B 5/1473* (2013.01); *A61B 5/1451* (2013.01); *A61B 5/14532* (2013.01);
(Continued)

(58) Field of Classification Search
CPC .............. A61B 5/14532; A61B 5/6849; A61B 17/3403; A61B 5/14503; A61B 5/1486;
(Continued)

(56) References Cited

U.S. PATENT DOCUMENTS 3,123,790 A    3/1964  Tyler
3,260,656 A    7/1966  Ross, Jr.
(Continued)

FOREIGN PATENT DOCUMENTS

DE        2903216      8/1979
DE         227029      9/1985
(Continued)

OTHER PUBLICATIONS

Abruna, H. D., et al., "Rectifying Interfaces Using Two-Layer Films of Electrochemically Polymerized Vinylpyridine and Vinylbipyridine Complexes of Ruthenium and Iron on Electrodes", *Journal of the American Chemical Society*, vol. 103, No. 1, 1981, pp. 1-5.
(Continued)

*Primary Examiner* — Patricia Mallari
*Assistant Examiner* — Karen Toth
(74) *Attorney, Agent, or Firm* — One LLP

(57) ABSTRACT

An analyte monitor includes a sensor, a sensor control unit, and a display unit. The sensor control unit typically has a housing adapted for placement on skin and is adapted to receive a portion of an electrochemical sensor. The sensor control unit also includes two or more conductive contacts disposed on the housing and configured for coupling to two or more contact pads on the sensor. A transmitter is disposed in the housing and coupled to the plurality of conductive contacts for transmitting data obtained using the sensor. The display unit has a receiver for receiving data transmitted by the transmitter of the sensor control unit and a display coupled to the receiver for displaying an indication of a level of an analyte, such as blood glucose. An inserter having a retractable introducer is provided for subcutaneously implanting the sensor in a predictable and reliable fashion.

34 Claims, 27 Drawing Sheets

Related U.S. Application Data continuation of application No. 11/899,917, filed on Sep. 6, 2007, now Pat. No. 8,029,442, which is a continuation of application No. 10/703,214, filed on Nov. 5, 2003, now Pat. No. 7,381,184.

(60) Provisional application No. 60/424,099, filed on Nov. 5, 2002.

(51) Int. Cl.
*A61B 5/145* (2006.01)
*A61B 17/34* (2006.01)
*A61N 1/05* (2006.01)
*A61N 1/08* (2006.01)

(52) U.S. Cl.
CPC ...... *A61B 5/14542* (2013.01); *A61B 5/14546* (2013.01); *A61B 5/6833* (2013.01); *A61B 5/6849* (2013.01); *A61B 17/3468* (2013.01); *A61M 2205/3507* (2013.01); *A61M 2230/201* (2013.01); *A61N 1/05* (2013.01); *A61N 1/08* (2013.01)

(58) Field of Classification Search
CPC ........ A61B 5/14865; A61M 2230/201; A61M 25/0612
See application file for complete search history.

(56) References Cited

U.S. PATENT DOCUMENTS

| | | |
|---|---|---|
| 3,522,807 A | 8/1970 | Millenbach |
| 3,581,062 A | 5/1971 | Aston |
| 3,653,841 A | 4/1972 | Klein |
| 3,670,727 A | 6/1972 | Reiterman |
| 3,719,564 A | 3/1973 | Lilly, Jr. et al. |
| 3,776,832 A | 12/1973 | Oswin et al. |
| 3,837,339 A | 9/1974 | Aisenberg et al. |
| 3,926,760 A | 12/1975 | Allen et al. |
| 3,949,388 A | 4/1976 | Fuller |
| 3,972,320 A | 8/1976 | Kalman |
| 3,979,274 A | 9/1976 | Newman |
| 4,008,717 A | 2/1977 | Kowarski |
| 4,016,866 A | 4/1977 | Lawton |
| 4,036,749 A | 7/1977 | Anderson |
| 4,055,175 A | 10/1977 | Clemens et al. |
| 4,059,406 A | 11/1977 | Fleet |
| 4,076,596 A | 2/1978 | Connery et al. |
| 4,098,574 A | 7/1978 | Dappen |
| 4,100,048 A | 7/1978 | Pompei et al. |
| 4,120,292 A | 10/1978 | LeBlanc, Jr. et al. |
| 4,129,128 A | 12/1978 | McFarlane |
| 4,151,845 A | 5/1979 | Clemens |
| 4,168,205 A | 9/1979 | Danniger et al. |
| 4,172,770 A | 10/1979 | Semersky et al. |
| 4,178,916 A | 12/1979 | McNamara |
| 4,206,755 A | 6/1980 | Klein |
| 4,224,125 A | 9/1980 | Nakamura et al. |
| 4,240,438 A | 12/1980 | Updike et al. |
| 4,245,634 A | 1/1981 | Albisser et al. |
| 4,247,297 A | 1/1981 | Berti et al. |
| 4,294,258 A | 10/1981 | Bernard |
| 4,327,725 A | 5/1982 | Cortese et al. |
| 4,340,458 A | 7/1982 | Lerner et al. |
| 4,344,438 A | 8/1982 | Schultz |
| 4,349,728 A | 9/1982 | Phillips et al. |
| 4,352,960 A | 10/1982 | Dormer et al. |
| 4,356,074 A | 10/1982 | Johnson |
| 4,365,637 A | 12/1982 | Johnson |
| 4,366,033 A | 12/1982 | Richter et al. |
| 4,373,527 A | 2/1983 | Fischell |
| 4,375,399 A | 3/1983 | Havas et al. |
| 4,384,586 A | 5/1983 | Christiansen |
| 4,390,621 A | 6/1983 | Bauer |
| 4,401,122 A | 8/1983 | Clark, Jr. |
| 4,404,066 A | 9/1983 | Johnson |
| 4,418,148 A | 11/1983 | Oberhardt |
| 4,425,920 A | 1/1984 | Bourland et al. |
| 4,427,770 A | 1/1984 | Chen et al. |
| 4,431,004 A | 2/1984 | Bessman et al. |
| 4,436,094 A | 3/1984 | Cerami |
| 4,440,175 A | 4/1984 | Wilkins |
| 4,450,842 A | 5/1984 | Zick et al. |
| 4,458,686 A | 7/1984 | Clark, Jr. |
| 4,461,691 A | 7/1984 | Frank |
| 4,469,110 A | 9/1984 | Slama |
| 4,477,314 A | 10/1984 | Richter et al. |
| 4,478,976 A | 10/1984 | Goertz et al. |
| 4,484,987 A | 11/1984 | Gough |
| 4,494,950 A | 1/1985 | Fischell |
| 4,509,531 A | 4/1985 | Ward |
| 4,522,690 A | 6/1985 | Venkatsetty |
| 4,524,114 A | 6/1985 | Samuels et al. |
| 4,526,661 A | 7/1985 | Steckhan et al. |
| 4,527,240 A | 7/1985 | Kvitash |
| 4,534,356 A | 8/1985 | Papadakis |
| 4,538,616 A | 9/1985 | Rogoff |
| 4,543,955 A | 10/1985 | Schroeppel |
| 4,545,382 A | 10/1985 | Higgins et al. |
| 4,552,840 A | 11/1985 | Riffer |
| 4,560,534 A | 12/1985 | Kung et al. |
| 4,571,292 A | 2/1986 | Liu et al. |
| 4,573,994 A | 3/1986 | Fischell et al. |
| 4,581,336 A | 4/1986 | Malloy et al. |
| 4,595,011 A | 6/1986 | Phillips |
| 4,619,754 A | 10/1986 | Niki et al. |
| 4,619,793 A | 10/1986 | Lee |
| 4,627,445 A | 12/1986 | Garcia et al. |
| 4,627,842 A | 12/1986 | Katz |
| 4,627,908 A | 12/1986 | Miller |
| 4,633,878 A | 1/1987 | Bombardien |
| 4,637,403 A | 1/1987 | Garcia et al. |
| 4,650,547 A | 3/1987 | Gough |
| 4,654,197 A | 3/1987 | Lilja et al. |
| 4,655,880 A | 4/1987 | Liu |
| 4,655,885 A | 4/1987 | Hill et al. |
| 4,671,288 A | 6/1987 | Gough |
| 4,679,562 A | 7/1987 | Luksha |
| 4,680,268 A | 7/1987 | Clark, Jr. |
| 4,682,602 A | 7/1987 | Prohaska |
| 4,684,537 A | 8/1987 | Graetzel et al. |
| 4,685,463 A | 8/1987 | Williams |
| 4,685,466 A | 8/1987 | Rau |
| 4,698,057 A | 10/1987 | Joishy |
| 4,703,756 A | 11/1987 | Gough et al. |
| 4,711,245 A | 12/1987 | Higgins et al. |
| 4,711,247 A | 12/1987 | Fishman |
| 4,717,673 A | 1/1988 | Wrighton et al. |
| 4,721,601 A | 1/1988 | Wrighton et al. |
| 4,721,677 A | 1/1988 | Clark, Jr. |
| 4,726,378 A | 2/1988 | Kaplan |
| 4,726,716 A | 2/1988 | McGuire |
| 4,729,672 A | 3/1988 | Takagi |
| 4,731,726 A | 3/1988 | Allen, III |
| 4,749,985 A | 6/1988 | Corsberg |
| 4,755,173 A | 7/1988 | Konopka |
| 4,757,022 A | 7/1988 | Shults et al. |
| 4,758,323 A | 7/1988 | Davis et al. |
| 4,759,371 A | 7/1988 | Franetzki |
| 4,759,828 A | 7/1988 | Young et al. |
| 4,764,416 A | 8/1988 | Ueyama et al. |
| 4,776,944 A | 10/1988 | Janata et al. |
| 4,777,953 A | 10/1988 | Ash et al. |
| 4,779,618 A | 10/1988 | Mund et al. |
| 4,781,683 A | 11/1988 | Wozniak et al. |
| 4,781,798 A | 11/1988 | Gough |
| 4,784,736 A | 11/1988 | Lonsdale et al. |
| 4,795,707 A | 1/1989 | Niiyama et al. |
| 4,796,634 A | 1/1989 | Huntsman et al. |
| 4,805,624 A | 2/1989 | Yao et al. |
| 4,813,424 A | 3/1989 | Wilkins |
| 4,815,469 A | 3/1989 | Cohen et al. |
| 4,820,399 A | 4/1989 | Senda et al. |

(56) References Cited

U.S. PATENT DOCUMENTS

| | | |
|---|---|---|
| 4,822,337 A | 4/1989 | Newhouse et al. |
| 4,830,959 A | 5/1989 | McNeil et al. |
| 4,832,797 A | 5/1989 | Vadgama et al. |
| RE32,947 E | 6/1989 | Dormer et al. |
| 4,840,893 A | 6/1989 | Hill et al. |
| 4,848,351 A | 7/1989 | Finch |
| 4,854,322 A | 8/1989 | Ash et al. |
| 4,871,351 A | 10/1989 | Feingold |
| 4,871,440 A | 10/1989 | Nagata et al. |
| 4,874,500 A | 10/1989 | Madou et al. |
| 4,890,620 A | 1/1990 | Gough |
| 4,894,137 A | 1/1990 | Takizawa et al. |
| 4,895,147 A | 1/1990 | Bodicky et al. |
| 4,897,162 A | 1/1990 | Lewandowski et al. |
| 4,897,173 A | 1/1990 | Nankai et al. |
| 4,909,908 A | 3/1990 | Ross et al. |
| 4,911,794 A | 3/1990 | Parce et al. |
| 4,917,800 A | 4/1990 | Lonsdale et al. |
| 4,919,141 A | 4/1990 | Zier et al. |
| 4,919,767 A | 4/1990 | Vadgama et al. |
| 4,921,199 A | 5/1990 | Villaveces |
| 4,923,586 A | 5/1990 | Katayama et al. |
| 4,925,268 A | 5/1990 | Iyer et al. |
| 4,927,516 A | 5/1990 | Yamaguchi et al. |
| 4,934,369 A | 6/1990 | Maxwell |
| 4,935,105 A | 6/1990 | Churchouse |
| 4,935,345 A | 6/1990 | Guibeau et al. |
| 4,938,860 A | 7/1990 | Wogoman |
| 4,944,299 A | 7/1990 | Silvian |
| 4,950,378 A | 8/1990 | Nagara |
| 4,953,552 A | 9/1990 | DeMarzo |
| 4,954,129 A | 9/1990 | Giuliani et al. |
| 4,969,468 A | 11/1990 | Byers et al. |
| 4,970,145 A | 11/1990 | Bennetto et al. |
| 4,974,929 A | 12/1990 | Curry |
| 4,986,271 A | 1/1991 | Wilkins |
| 4,988,341 A | 1/1991 | Columbus et al. |
| 4,994,167 A | 2/1991 | Shults et al. |
| 4,995,402 A | 2/1991 | Smith et al. |
| 5,000,180 A | 3/1991 | Kuypers et al. |
| 5,001,054 A | 3/1991 | Wagner |
| 5,013,161 A | 5/1991 | Zaragoza et al. |
| 5,019,974 A | 5/1991 | Beckers |
| 5,035,860 A | 7/1991 | Kleingeld et al. |
| 5,036,860 A | 8/1991 | Leigh et al. |
| 5,047,044 A | 9/1991 | Smith et al. |
| 5,050,612 A | 9/1991 | Matsumura |
| 5,055,171 A | 10/1991 | Peck |
| 5,058,592 A | 10/1991 | Whisler |
| 5,070,535 A | 12/1991 | Hochmair et al. |
| 5,082,550 A | 1/1992 | Rishpon et al. |
| 5,082,786 A | 1/1992 | Nakamoto |
| 5,089,112 A | 2/1992 | Skotheim et al. |
| 5,095,904 A | 3/1992 | Seligman et al. |
| 5,101,814 A | 4/1992 | Palti |
| 5,106,365 A | 4/1992 | Hernandez |
| 5,108,564 A | 4/1992 | Szuminsky et al. |
| 5,108,889 A | 4/1992 | Smith et al. |
| 5,109,850 A | 5/1992 | Blanco et al. |
| 5,120,420 A | 6/1992 | Nankai et al. |
| 5,122,925 A | 6/1992 | Inpyn |
| 5,126,034 A | 6/1992 | Carter et al. |
| 5,133,856 A | 7/1992 | Yamaguchi et al. |
| 5,135,003 A | 8/1992 | Souma |
| 5,140,985 A | 8/1992 | Schroeder et al. |
| 5,141,868 A | 8/1992 | Shanks et al. |
| 5,161,532 A | 11/1992 | Joseph |
| 5,165,407 A | 11/1992 | Wilson et al. |
| 5,174,291 A | 12/1992 | Schoonen et al. |
| 5,190,041 A | 3/1993 | Palti |
| 5,192,416 A | 3/1993 | Wang et al. |
| 5,198,367 A | 3/1993 | Aizawa et al. |
| 5,202,261 A | 4/1993 | Musho et al. |
| 5,205,920 A | 4/1993 | Oyama et al. |
| 5,208,154 A | 5/1993 | Weaver et al. |
| 5,209,229 A | 5/1993 | Gilli |
| 5,217,595 A | 6/1993 | Smith et al. |
| 5,229,282 A | 7/1993 | Yoshioka et al. |
| 5,234,835 A | 8/1993 | Nestor et al. |
| 5,238,729 A | 8/1993 | Debe |
| 5,246,867 A | 9/1993 | Lakowicz et al. |
| 5,250,439 A | 10/1993 | Musho et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,264,106 A | 11/1993 | McAleer et al. |
| 5,271,815 A | 12/1993 | Wong |
| 5,279,294 A | 1/1994 | Anderson |
| 5,284,156 A | 2/1994 | Schramm et al. |
| 5,285,792 A | 2/1994 | Sjoquist et al. |
| 5,286,362 A | 2/1994 | Hoenes et al. |
| 5,286,364 A | 2/1994 | Yacynych et al. |
| 5,288,636 A | 2/1994 | Pollmann et al. |
| 5,293,546 A | 3/1994 | Tadros et al. |
| 5,293,877 A | 3/1994 | O'Hara et al. |
| 5,299,571 A | 4/1994 | Mastrototaro |
| 5,320,098 A | 6/1994 | Davidson |
| 5,320,725 A | 6/1994 | Gregg et al. |
| 5,322,063 A | 6/1994 | Allen et al. |
| 5,337,747 A | 8/1994 | Neftei |
| 5,340,722 A | 8/1994 | Wolfbeis et al. |
| 5,342,789 A | 8/1994 | Chick et al. |
| 5,352,348 A | 10/1994 | Young et al. |
| 5,356,786 A | 10/1994 | Heller et al. |
| 5,360,404 A | 11/1994 | Novacek et al. |
| 5,368,028 A | 11/1994 | Palti |
| 5,372,133 A | 12/1994 | Hogen Esch |
| 5,372,427 A | 12/1994 | Padovani et al. |
| 5,376,251 A | 12/1994 | Kaneko et al. |
| 5,378,628 A | 1/1995 | Gratzel et al. |
| 5,379,238 A | 1/1995 | Stark |
| 5,387,327 A | 2/1995 | Khan |
| 5,390,671 A | 2/1995 | Lord et al. |
| 5,391,250 A | 2/1995 | Cheney, II et al. |
| 5,395,504 A | 3/1995 | Saurer et al. |
| 5,400,782 A | 3/1995 | Beaubiah |
| 5,408,999 A | 4/1995 | Singh et al. |
| 5,411,647 A | 5/1995 | Johnson et al. |
| 5,425,361 A | 6/1995 | Fenzlein et al. |
| 5,431,160 A | 7/1995 | Wilkins |
| 5,431,921 A | 7/1995 | Thombre |
| 5,437,999 A | 8/1995 | Dieboid et al. |
| 5,462,645 A | 10/1995 | Albery et al. |
| 5,469,846 A | 11/1995 | Khan |
| 5,472,317 A | 12/1995 | Field et al. |
| 5,489,414 A | 2/1996 | Schreiber et al. |
| 5,491,474 A | 2/1996 | Suni et al. |
| 5,494,562 A | 2/1996 | Maley et al. |
| 5,496,453 A | 3/1996 | Uenoyama et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,545,191 A | 8/1996 | Mann et al. |
| 5,549,568 A | 8/1996 | Sheilds |
| 5,551,427 A | 9/1996 | Altman |
| 5,560,357 A | 10/1996 | Faupei et al. |
| 5,562,713 A | 10/1996 | Silvian |
| 5,565,085 A | 10/1996 | Ikeda et al. |
| 5,567,302 A | 10/1996 | Song et al. |
| 5,568,806 A * | 10/1996 | Cheney, II ......... A61B 5/14532 600/373 |
| 5,569,186 A | 10/1996 | Lord et al. |
| 5,575,563 A | 11/1996 | Chiu et al. |
| 5,582,184 A | 12/1996 | Erickson et al. |
| 5,582,697 A | 12/1996 | Ikeda et al. |
| 5,582,698 A | 12/1996 | Flaherty et al. |
| 5,584,813 A | 12/1996 | Livingston et al. |
| 5,586,553 A | 12/1996 | Halli et al. |
| 5,589,326 A | 12/1996 | Deng et al. |
| 5,593,852 A | 1/1997 | Heller et al. |

(56) References Cited

U.S. PATENT DOCUMENTS

| | | |
|---|---|---|
| 5,596,150 A | 1/1997 | Arndt et al. |
| 5,601,435 A | 2/1997 | Quy |
| 5,609,575 A | 3/1997 | Larson et al. |
| 5,617,851 A | 4/1997 | Lipkovker |
| 5,628,310 A | 5/1997 | Rao et al. |
| 5,628,890 A | 5/1997 | Carter et al. |
| 5,632,557 A | 5/1997 | Simons |
| 5,640,954 A | 6/1997 | Pfeiffer et al. |
| 5,651,869 A | 7/1997 | Yoshioka et al. |
| 5,653,239 A | 8/1997 | Pompei et al. |
| 5,660,163 A | 8/1997 | Schulman et al. |
| 5,665,071 A | 9/1997 | Wyrick |
| 5,665,222 A | 9/1997 | Heller et al. |
| 5,670,031 A | 9/1997 | Hintsche et al. |
| 5,680,858 A | 10/1997 | Hansen et al. |
| 5,682,233 A | 10/1997 | Brinda |
| 5,695,623 A | 12/1997 | Michel et al. |
| 5,708,247 A | 1/1998 | McAleer et al. |
| 5,711,001 A | 1/1998 | Bussan et al. |
| 5,711,297 A | 1/1998 | Iliff et al. |
| 5,711,861 A | 1/1998 | Ward et al. |
| 5,711,862 A | 1/1998 | Sakoda et al. |
| 5,733,044 A | 3/1998 | Rose et al. |
| 5,735,285 A | 4/1998 | Albert et al. |
| 5,741,211 A | 4/1998 | Renirie et al. |
| 5,749,656 A | 5/1998 | Boehm et al. |
| 5,766,131 A | 6/1998 | Kondo et al. |
| 5,771,001 A | 6/1998 | Cobb |
| 5,772,586 A | 6/1998 | Heinonen et al. |
| 5,779,665 A | 7/1998 | Mastrototaro et al. |
| 5,791,344 A | 8/1998 | Schulman et al. |
| 5,800,420 A | 9/1998 | Gross et al. |
| 5,807,375 A | 9/1998 | Gross et al. |
| 5,814,020 A | 9/1998 | Gross |
| 5,820,551 A | 10/1998 | Hill et al. |
| 5,820,622 A | 10/1998 | Gross et al. |
| 5,822,715 A | 10/1998 | Worthington et al. |
| 5,827,184 A | 10/1998 | Netherly et al. |
| 5,840,020 A | 11/1998 | Heinonen et al. |
| 5,842,983 A | 12/1998 | Abel et al. |
| 5,851,197 A | 12/1998 | Marano et al. |
| 5,858,001 A | 1/1999 | Tsals et al. |
| 5,865,804 A | 2/1999 | Bachynsky |
| 5,885,211 A | 3/1999 | Eppstein et al. |
| 5,899,855 A | 5/1999 | Brown |
| 5,924,979 A | 7/1999 | Sedlow et al. |
| 5,925,021 A | 7/1999 | Castellano et al. |
| 5,931,868 A | 8/1999 | Gross et al. |
| 5,948,006 A | 9/1999 | Mann |
| 5,951,521 A | 9/1999 | Mastrototaro et al. |
| 5,954,643 A | 9/1999 | Van Antwerp |
| 5,954,685 A | 9/1999 | Tierny |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,987,353 A | 11/1999 | Khatchatrian et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,017,335 A | 1/2000 | Burnham |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,049,727 A | 4/2000 | Crothall |
| 6,056,718 A | 5/2000 | Funderburk et al. |
| 6,068,399 A | 5/2000 | Tseng |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A * | 7/2000 | Funderburk .......... A61M 5/158 604/131 |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |
| 6,159,147 A | 12/2000 | Lichter et al. |
| 6,162,611 A | 12/2000 | Heller et al. |
| 6,175,752 B1 | 1/2001 | Say et al. |
| 6,186,982 B1 | 2/2001 | Gross et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,254,536 B1 | 7/2001 | DeVito |
| 6,254,586 B1 | 7/2001 | Mann et al. |
| 6,275,717 B1 | 8/2001 | Gross et al. |
| 6,283,761 B1 | 9/2001 | Joao |
| 6,283,982 B1 | 9/2001 | Levaughn et al. |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,331,244 B1 | 12/2001 | Lewis et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,377,828 B1 | 4/2002 | Chaiken et al. |
| 6,379,301 B1 | 4/2002 | Worthington et al. |
| 6,409,740 B1 | 6/2002 | Kuhr et al. |
| 6,413,393 B1 | 7/2002 | Van Antwerp et al. |
| 6,418,332 B1 | 7/2002 | Mastrototaro et al. |
| 6,424,847 B1 | 7/2002 | Mastrototaro et al. |
| 6,427,088 B1 | 7/2002 | Bowman, IV et al. |
| 6,437,679 B1 | 8/2002 | Roques |
| 6,440,068 B1 | 8/2002 | Brown et al. |
| 6,445,374 B2 | 9/2002 | Albert et al. |
| 6,478,736 B1 | 11/2002 | Mault |
| 6,482,176 B1 | 11/2002 | Wich |
| 6,484,045 B1 | 11/2002 | Holker et al. |
| 6,484,046 B1 | 11/2002 | Say et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,551,494 B1 | 4/2003 | Heller et al. |
| 6,554,795 B2 | 4/2003 | Lam et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,566 B2 | 6/2003 | Effenhauser |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |

(56) References Cited

U.S. PATENT DOCUMENTS

| | | |
|---|---|---|
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,666,849 B1 | 12/2003 | Marshall et al. |
| 6,668,196 B1 | 12/2003 | Villegas et al. |
| 6,676,290 B1 | 1/2004 | Lu |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,830,551 B1 | 12/2004 | Uchigaki et al. |
| 6,837,858 B2 | 1/2005 | Cunningham et al. |
| 6,837,885 B2 | 1/2005 | Koblish et al. |
| 6,837,988 B2 | 1/2005 | Leong et al. |
| 6,849,052 B2 | 2/2005 | Ughigaki et al. |
| 6,854,882 B2 | 2/2005 | Chen |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,959,211 B2 | 10/2005 | Rule et al. |
| 6,968,294 B2 | 11/2005 | Gutta et al. |
| 6,971,274 B2 | 12/2005 | Olin |
| 6,971,999 B2 | 12/2005 | Py et al. |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,024,245 B2 | 4/2006 | Lebel et al. |
| 7,025,743 B2 | 4/2006 | Mann et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,097,637 B2 | 8/2006 | Triplett et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,297,151 B2 | 11/2007 | Boecker et al. |
| 7,299,082 B2 | 11/2007 | Feldman et al. |
| 7,310,544 B2 | 12/2007 | Brister et al. |
| 7,318,816 B2 | 1/2008 | Bobroff et al. |
| 7,324,012 B2 | 1/2008 | Mann et al. |
| 7,329,239 B2 | 2/2008 | Safabash et al. |
| 7,335,294 B2 | 2/2008 | Heller et al. |
| 7,340,287 B2 | 3/2008 | Mason et al. |
| 7,340,309 B2 | 3/2008 | Miazga et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,381,184 B2 | 6/2008 | Funderburk et al. |
| 7,402,153 B2 | 7/2008 | Steil et al. |
| 7,416,541 B2 | 8/2008 | Yuzhakov et al. |
| 7,424,318 B2 | 9/2008 | Brister et al. |
| 7,455,663 B2 | 11/2008 | Bikovsky |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,604,592 B2 | 10/2009 | Freeman et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,660,615 B2 * | 2/2010 | VanAntwerp ...... A61B 5/14532 439/834 |
| 7,666,149 B2 | 2/2010 | Simons et al. |
| 7,682,338 B2 | 3/2010 | Griffin |
| 7,697,967 B2 | 4/2010 | Stafford |
| 7,711,402 B2 | 5/2010 | Shults et al. |
| 7,713,574 B2 | 5/2010 | Brister et al. |
| 7,715,893 B2 | 5/2010 | Kamath et al. |
| 7,727,147 B1 | 6/2010 | Osorio et al. |
| 7,731,657 B2 | 6/2010 | Stafford |
| 7,736,344 B2 | 6/2010 | Moberg et al. |
| 7,763,042 B2 | 7/2010 | Iio et al. |
| 7,822,454 B1 | 10/2010 | Alden et al. |
| 2001/0056262 A1 | 12/2001 | Cabiri et al. |
| 2002/0013538 A1 | 1/2002 | Teller |
| 2002/0019022 A1 | 2/2002 | Dunn et al. |
| 2002/0019606 A1 | 2/2002 | Lebel et al. |
| 2002/0022855 A1 | 2/2002 | Bobroff et al. |
| 2002/0023852 A1 | 2/2002 | McIvor et al. |
| 2002/0042090 A1 | 4/2002 | Heller et al. |
| 2002/0055711 A1 | 5/2002 | Lavi et al. |
| 2002/0057993 A1 | 5/2002 | Maisey et al. |
| 2002/0066764 A1 | 6/2002 | Perry et al. |
| 2002/0076966 A1 | 6/2002 | Carron et al. |
| 2002/0082487 A1 | 6/2002 | Kollias et al. |
| 2002/0103499 A1 | 8/2002 | Perez et al. |
| 2002/0106709 A1 | 8/2002 | Potts et al. |
| 2002/0119711 A1 | 8/2002 | VanAntwerp et al. |
| 2002/0128594 A1 | 9/2002 | Das et al. |
| 2002/0130042 A1 | 9/2002 | Moerman et al. |
| 2002/0154050 A1 | 10/2002 | Krupp et al. |
| 2002/0161288 A1 | 10/2002 | Shin et al. |
| 2002/0165462 A1 | 11/2002 | Westbrook et al. |
| 2002/0169369 A1 | 11/2002 | Ward et al. |
| 2002/0198444 A1 | 12/2002 | Ughigaki et al. |
| 2003/0023317 A1 | 1/2003 | Brauker et al. |
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0060753 A1 | 3/2003 | Starkweather et al. |
| 2003/0065308 A1 | 4/2003 | Lebel et al. |
| 2003/0069510 A1 | 4/2003 | Semler |

(56) References Cited

U.S. PATENT DOCUMENTS

| | | |
|---|---|---|
| 2003/0078481 A1 | 4/2003 | McIvor et al. |
| 2003/0078560 A1 | 4/2003 | Miller et al. |
| 2003/0083686 A1 | 5/2003 | Freeman et al. |
| 2003/0097092 A1 | 5/2003 | Flaherty |
| 2003/0100040 A1 | 5/2003 | Bonnecaze et al. |
| 2003/0109775 A1 | 6/2003 | O'Neil et al. |
| 2003/0134347 A1 | 7/2003 | Heller et al. |
| 2003/0135333 A1 | 7/2003 | Aceti et al. |
| 2003/0144581 A1 | 7/2003 | Conn et al. |
| 2003/0144608 A1 | 7/2003 | Kojima et al. |
| 2003/0155656 A1 | 8/2003 | Chiu et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0199910 A1 | 10/2003 | Boecker et al. |
| 2003/0212379 A1 | 11/2003 | Bylund et al. |
| 2003/0217966 A1 | 11/2003 | Tapsak et al. |
| 2003/0225361 A1 | 12/2003 | Sabra |
| 2004/0002682 A1 | 1/2004 | Kovelman et al. |
| 2004/0010207 A1 | 1/2004 | Flaherty et al. |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0064133 A1 | 4/2004 | Miller et al. |
| 2004/0096959 A1 | 5/2004 | Steine et al. |
| 2004/0106858 A1 | 6/2004 | Say et al. |
| 2004/0106859 A1 | 6/2004 | Say et al. |
| 2004/0116847 A1 | 6/2004 | Wall |
| 2004/0116865 A1 | 6/2004 | Bengtsson |
| 2004/0122353 A1 | 6/2004 | Shahmirian et al. |
| 2004/0122489 A1 | 6/2004 | Mazar et al. |
| 2004/0116866 A1 | 7/2004 | Gorman et al. |
| 2004/0133164 A1 | 7/2004 | Funderburk et al. |
| 2004/0135684 A1 | 7/2004 | Steinthal et al. |
| 2004/0138544 A1 | 7/2004 | Ward et al. |
| 2004/0138588 A1 | 7/2004 | Saikley et al. |
| 2004/0138688 A1 | 7/2004 | Giraud |
| 2004/0147996 A1 | 7/2004 | Miazga et al. |
| 2004/0152622 A1 | 8/2004 | Keith et al. |
| 2004/0158207 A1 | 8/2004 | Hunn et al. |
| 2004/0167801 A1 | 8/2004 | Say et al. |
| 2004/0171910 A1 | 9/2004 | Moore-Steele |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |
| 2004/0210122 A1 | 10/2004 | Sleburg |
| 2004/0223985 A1 | 11/2004 | Dunfiled et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0254433 A1 | 12/2004 | Bandis et al. |
| 2004/0254434 A1 | 12/2004 | Goodnow et al. |
| 2004/0267300 A1 | 12/2004 | Mace |
| 2005/0003470 A1 | 1/2005 | Nelson et al. |
| 2005/0004494 A1 | 1/2005 | Perez et al. |
| 2005/0006122 A1 | 1/2005 | Burnette |
| 2005/0010269 A1 | 1/2005 | Lebel et al. |
| 2005/0027177 A1 | 2/2005 | Shin et al. |
| 2005/0027180 A1 | 2/2005 | Goode, Jr. et al. |
| 2005/0031689 A1 | 2/2005 | Shults et al. |
| 2005/0043598 A1 | 2/2005 | Goode, Jr. et al. |
| 2005/0070819 A1 | 3/2005 | Poux et al. |
| 2005/0085872 A1 | 4/2005 | Yanagihara et al. |
| 2005/0090607 A1 | 4/2005 | Tapsak et al. |
| 2005/0090850 A1 | 4/2005 | Thoes et al. |
| 2005/0106713 A1 | 5/2005 | Phan et al. |
| 2005/0112169 A1 | 5/2005 | Brauker et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0143635 A1 | 6/2005 | Kamath et al. |
| 2005/0154410 A1 | 7/2005 | Conway et al. |
| 2005/0165404 A1 | 7/2005 | Miller |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0199494 A1 | 9/2005 | Say et al. |
| 2005/0203360 A1 | 9/2005 | Brauker et al. |
| 2005/0222518 A1 | 10/2005 | Dib |
| 2005/0222599 A1 | 10/2005 | Czernecki et al. |
| 2005/0236277 A9 | 10/2005 | Imran et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245844 A1 | 11/2005 | Mace et al. |
| 2005/0277164 A1 | 12/2005 | Drucker et al. |
| 2005/0283114 A1 | 12/2005 | Bresina et al. |
| 2005/0287620 A1 | 12/2005 | Heller et al. |
| 2006/0001538 A1 | 1/2006 | Kraft et al. |
| 2006/0004303 A1 | 1/2006 | Weidenhaupt et al. |
| 2006/0009727 A1 | 1/2006 | O'Mahony et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0047220 A1 | 3/2006 | Sakata et al. |
| 2006/0081469 A1 | 4/2006 | Lee |
| 2006/0129173 A1 | 6/2006 | Wilkinson |
| 2006/0155210 A1 | 7/2006 | Beckman et al. |
| 2006/0155317 A1 | 7/2006 | List et al. |
| 2006/0161664 A1 | 7/2006 | Motoyama |
| 2006/0166629 A1 | 7/2006 | Reggiardo |
| 2006/0173444 A1 | 8/2006 | Choy et al. |
| 2006/0189863 A1 | 8/2006 | Peyser et al. |
| 2006/0189939 A1 | 8/2006 | Gonnelli et al. |
| 2006/0195029 A1 | 8/2006 | Shults et al. |
| 2006/0200181 A1 | 9/2006 | Fukuzawa et al. |
| 2006/0200970 A1 | 9/2006 | Brister et al. |
| 2006/0222566 A1 | 10/2006 | Brauker et al. |
| 2006/0224171 A1 | 10/2006 | Sakata et al. |
| 2006/0226985 A1 | 10/2006 | Goodnow et al. |
| 2006/0247508 A1 | 11/2006 | Fennell |
| 2006/0253086 A1 | 11/2006 | Moberg et al. |
| 2006/0258929 A1 | 11/2006 | Goode, Jr. et al. |
| 2006/0264888 A1 | 11/2006 | Moberg et al. |
| 2006/0276724 A1 | 12/2006 | Freeman et al. |
| 2006/0282042 A1 | 12/2006 | Walters et al. |
| 2006/0287591 A1 | 12/2006 | Ocvirk et al. |
| 2007/0016381 A1 | 1/2007 | Kamath et al. |
| 2007/0027381 A1 | 2/2007 | Stafford |
| 2007/0038044 A1 | 2/2007 | Dobbles et al. |
| 2007/0060814 A1 | 3/2007 | Stafford |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |

(56) References Cited

U.S. PATENT DOCUMENTS

| | | |
|---|---|---|
| 2007/0088377 A1 | 4/2007 | Levaughn et al. |
| 2007/0106135 A1 | 5/2007 | Sloan et al. |
| 2007/0110124 A1 | 5/2007 | Shiraki et al. |
| 2007/0123819 A1 | 5/2007 | Mernoe et al. |
| 2007/0149875 A1 | 6/2007 | Ouyang et al. |
| 2007/0156094 A1 | 7/2007 | Safabash et al. |
| 2007/0163880 A1 | 7/2007 | Woo et al. |
| 2007/0173706 A1 | 7/2007 | Neinast et al. |
| 2007/0173741 A1 | 7/2007 | Deshmukh et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0213611 A1 | 9/2007 | Simpson et al. |
| 2007/0235331 A1 | 10/2007 | Simpson et al. |
| 2007/0244368 A1 | 10/2007 | Bayloff et al. |
| 2007/0244398 A1 | 10/2007 | Lo et al. |
| 2007/0249922 A1 | 10/2007 | Peyser et al. |
| 2007/0255302 A1 | 11/2007 | Koeppel et al. |
| 2008/0004512 A1 | 1/2008 | Funderburk et al. |
| 2008/0004573 A1 | 1/2008 | Kaufmann et al. |
| 2008/0009692 A1 | 1/2008 | Stafford |
| 2008/0009805 A1 | 1/2008 | Ethelfeld |
| 2008/0017522 A1 | 1/2008 | Heller et al. |
| 2008/0021666 A1 | 1/2008 | Goode, Jr. et al. |
| 2008/0027474 A1 | 1/2008 | Curry et al. |
| 2008/0029391 A1 | 2/2008 | Mao et al. |
| 2008/0033254 A1 | 2/2008 | Kamath et al. |
| 2008/0033268 A1 | 2/2008 | Stafford |
| 2008/0033318 A1 | 2/2008 | Mace et al. |
| 2008/0039702 A1 | 2/2008 | Hayter et al. |
| 2008/0045824 A1 | 2/2008 | Tapsak et al. |
| 2008/0064937 A1 | 3/2008 | McGarraugh et al. |
| 2008/0064941 A1 | 3/2008 | Funderburk et al. |
| 2008/0065646 A1 | 3/2008 | Zhang et al. |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097246 A1 | 4/2008 | Stafford |
| 2008/0108942 A1 | 5/2008 | Brister et al. |
| 2008/0112848 A1 | 5/2008 | Huffstodt et al. |
| 2008/0114280 A1 | 5/2008 | Stafford |
| 2008/0119707 A1 | 5/2008 | Stafford |
| 2008/0133702 A1 | 6/2008 | Sharma et al. |
| 2008/0154205 A1 | 6/2008 | Wojcik |
| 2008/0167578 A1 | 7/2008 | Bryer et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0214481 A1 | 9/2008 | Challoner et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0269673 A1 | 10/2008 | Butoi et al. |
| 2008/0275313 A1 | 11/2008 | Brister et al. |
| 2008/0283396 A1 | 11/2008 | Wang et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0294096 A1 | 11/2008 | Uber et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0005659 A1 | 1/2009 | Kollias et al. |
| 2009/0012377 A1 | 1/2009 | Jennewine et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0036915 A1 | 2/2009 | Karbowniczek et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0054866 A1 | 2/2009 | Teisen-Simony et al. |
| 2009/0062633 A1 | 3/2009 | Brauker et al. |
| 2009/0062635 A1 | 3/2009 | Brauker et al. |
| 2009/0069750 A1 | 3/2009 | Schraga |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0088614 A1 | 4/2009 | Taub |
| 2009/0088787 A1 | 4/2009 | Koike et al. |
| 2009/0099436 A1 | 4/2009 | Brister et al. |
| 2009/0102678 A1 | 4/2009 | Mazza et al. |
| 2009/0105569 A1 | 4/2009 | Stafford |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0124979 A1 | 5/2009 | Raymond et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0171182 A1 | 7/2009 | Stafford |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198215 A1 | 8/2009 | Chong et al. |
| 2009/0203981 A1 | 8/2009 | Brauker et al. |
| 2009/0204341 A1 | 8/2009 | Brauker et al. |
| 2009/0212766 A1 | 8/2009 | Olson et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0259118 A1 | 10/2009 | Feldman et al. |
| 2009/0259201 A1 | 10/2009 | Hwang et al. |
| 2009/0259202 A1 | 10/2009 | Leeflang et al. |

(56) References Cited

U.S. PATENT DOCUMENTS

| | | |
|---|---|---|
| 2009/0270765 A1 | 10/2009 | Ghesquire et al. |
| 2009/0287073 A1 | 11/2009 | Boock et al. |
| 2009/0287074 A1 | 11/2009 | Shults et al. |
| 2009/0292184 A1 | 11/2009 | Funderburk et al. |
| 2009/0292185 A1 | 11/2009 | Funderburk et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299167 A1 | 12/2009 | Seymour |
| 2009/0299276 A1 | 12/2009 | Brauker et al. |
| 2010/0004597 A1 | 1/2010 | Gryn et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049014 A1 | 2/2010 | Funderburk et al. |
| 2010/0049024 A1 | 2/2010 | Saint et al. |
| 2010/0063373 A1 | 3/2010 | Kamath et al. |
| 2010/0069728 A1 | 3/2010 | Funderburk et al. |
| 2010/0076283 A1 | 3/2010 | Simpson et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0100113 A1 | 4/2010 | Iio et al. |
| 2010/0106088 A1 | 4/2010 | Yodfat et al. |
| 2010/0113897 A1 | 5/2010 | Brenneman et al. |
| 2010/0119693 A1 | 5/2010 | Tapsak et al. |
| 2010/0121169 A1 | 5/2010 | Petisce et al. |
| 2010/0168677 A1 | 7/2010 | Gabriel et al. |
| 2010/0174157 A1 | 7/2010 | Brister et al. |
| 2010/0174158 A1 | 7/2010 | Kamath et al. |
| 2010/0174163 A1 | 7/2010 | Brister et al. |
| 2010/0174164 A1 | 7/2010 | Brister et al. |
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185069 A1 | 7/2010 | Brister et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185075 A1 | 7/2010 | Brister et al. |
| 2010/0191082 A1 | 7/2010 | Brister et al. |
| 2010/0198033 A1 | 8/2010 | Krulevitch et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0204653 A1 | 8/2010 | Gryn et al. |
| 2010/0212583 A1 | 8/2010 | Brister et al. |
| 2010/0214104 A1 | 8/2010 | Goode et al. |
| 2010/0217105 A1 | 8/2010 | Yodfat et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0240975 A1 | 9/2010 | Goode et al. |
| 2010/0240976 A1 | 9/2010 | Goode et al. |
| 2010/0261987 A1 | 10/2010 | Kamath et al. |
| 2010/0262201 A1 | 10/2010 | He et al. |
| 2010/0274107 A1 | 10/2010 | Boock et al. |
| 2010/0280341 A1 | 11/2010 | Boock et al. |
| 2010/0286496 A1 | 11/2010 | Simpson et al. |
| 2010/0298684 A1 | 11/2010 | Leach et al. |
| 2010/0324392 A1 | 12/2010 | Yee et al. |
| 2010/0324403 A1 | 12/2010 | Brister et al. |
| 2010/0331642 A1 | 12/2010 | Bruce et al. |
| 2010/0331644 A1 | 12/2010 | Neale et al. |
| 2010/0331647 A1 | 12/2010 | Shah et al. |
| 2010/0331648 A1 | 12/2010 | Kamath et al. |
| 2010/0331653 A1 | 12/2010 | Stafford |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0009727 A1 | 1/2011 | Mensinger et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0040256 A1 | 2/2011 | Bobroff et al. |
| 2011/0040263 A1 | 2/2011 | Hordum et al. |
| 2011/0046456 A1 | 2/2011 | Hordum et al. |
| 2011/0046467 A1 | 2/2011 | Simpson et al. |
| 2011/0054275 A1 | 3/2011 | Stafford |
| 2011/0060196 A1 | 3/2011 | Stafford |
| 2011/0073475 A1 | 3/2011 | Kastanos et al. |
| 2011/0077490 A1 | 3/2011 | Simpson et al. |
| 2011/0118579 A1 | 5/2011 | Goode et al. |
| 2011/0118580 A1 | 5/2011 | Goode et al. |
| 2011/0124992 A1 | 5/2011 | Brauker et al. |
| 2011/0124997 A1 | 5/2011 | Goode et al. |
| 2011/0125410 A1 | 5/2011 | Goode et al. |
| 2011/0130970 A1 | 6/2011 | Goode et al. |
| 2011/0130971 A1 | 6/2011 | Goode et al. |
| 2011/0130998 A1 | 6/2011 | Goode et al. |
| 2011/0137257 A1 | 6/2011 | Gyrn et al. |
| 2011/0144465 A1 | 6/2011 | Shults et al. |
| 2011/0178378 A1 | 7/2011 | Brister et al. |
| 2011/0178461 A1 | 7/2011 | Chong et al. |
| 2011/0184258 A1 | 7/2011 | Stafford |
| 2011/0190614 A1 | 8/2011 | Brister et al. |
| 2011/0201910 A1 | 8/2011 | Rasdal et al. |
| 2011/0201911 A1 | 8/2011 | Johnson et al. |
| 2011/0218414 A1 | 9/2011 | Kamath et al. |
| 2011/0231107 A1 | 9/2011 | Brauker et al. |
| 2011/0231140 A1 | 9/2011 | Goode et al. |
| 2011/0231141 A1 | 9/2011 | Goode et al. |
| 2011/0231142 A1 | 9/2011 | Goode et al. |
| 2011/0253533 A1 | 10/2011 | Shults et al. |
| 2011/0257521 A1 | 10/2011 | Fraden |
| 2011/0257895 A1 | 10/2011 | Brauker et al. |
| 2011/0263958 A1 | 10/2011 | Brauker et al. |
| 2011/0270062 A1 | 11/2011 | Goode et al. |
| 2011/0270158 A1 | 11/2011 | Brauker et al. |
| 2011/0275919 A1 | 11/2011 | Petisce et al. |
| 2011/0290645 A1 | 12/2011 | Brister et al. |
| 2011/0313543 A1 | 12/2011 | Brauker et al. |
| 2011/0319739 A1 | 12/2011 | Kamath et al. |
| 2011/0320130 A1 | 12/2011 | Valdes et al. |
| 2012/0035445 A1 | 2/2012 | Boock et al. |
| 2012/0040101 A1 | 2/2012 | Tapsak et al. |

(56) References Cited

U.S. PATENT DOCUMENTS

| | | |
|---|---|---|
| 2012/0046534 A1 | 2/2012 | Simpson et al. |
| 2012/0078071 A1 | 3/2012 | Bohm et al. |
| 2012/0108934 A1 | 5/2012 | Valdes et al. |
| 2012/0108983 A1 | 5/2012 | Banet et al. |
| 2012/0123385 A1 | 5/2012 | Edwards et al. |
| 2012/0143135 A1 | 6/2012 | Cole et al. |
| 2012/0296327 A1 | 11/2012 | Hutchins et al. |
| 2013/0047981 A1 | 2/2013 | Bacon |

FOREIGN PATENT DOCUMENTS

| | | |
|---|---|---|
| DE | 3934299 | 10/1990 |
| EP | 0010375 A1 | 4/1980 |
| EP | 0026995 A1 | 4/1981 |
| EP | 0048090 A2 | 3/1982 |
| EP | 0078636 A1 | 5/1983 |
| EP | 0080304 B1 | 6/1983 |
| EP | 0096288 A1 | 12/1983 |
| EP | 0098592 | 1/1984 |
| EP | 0125139 A2 | 11/1984 |
| EP | 0127958 | 12/1984 |
| EP | 0136362 A1 | 4/1985 |
| EP | 0170375 A2 | 2/1986 |
| EP | 0177743 A2 | 4/1986 |
| EP | 0184909 A2 | 6/1986 |
| EP | 0206218 A2 | 12/1986 |
| EP | 0230472 A1 | 8/1987 |
| EP | 0241309 A3 | 10/1987 |
| EP | 0245073 A2 | 11/1987 |
| EP | 0255291 | 2/1988 |
| EP | 0278647 | 8/1988 |
| EP | 0320109 | 6/1989 |
| EP | 0353328 | 2/1990 |
| EP | 0359831 | 3/1990 |
| EP | 0368209 | 5/1990 |
| EP | 0390390 | 10/1990 |
| EP | 0396788 | 11/1990 |
| EP | 0400918 | 12/1990 |
| EP | 0453283 | 10/1991 |
| EP | 0470290 | 2/1992 |
| EP | 0286118 | 1/1995 |
| EP | 1048264 | 11/2000 |
| EP | 1177802 | 2/2002 |
| EP | 0987982 | 1/2007 |
| EP | 2060284 | 5/2009 |
| EP | 2201969 | 6/2010 |
| EP | 2327362 | 6/2011 |
| EP | 2335587 | 6/2011 |
| GB | 1394171 | 5/1975 |
| GB | 1599241 | 9/1981 |
| GB | 2073891 | 10/1981 |
| GB | 2154003 | 8/1985 |
| GB | 2204408 | 11/1988 |
| GB | 2254436 | 10/1992 |
| JP | 54-041191 | 4/1979 |
| JP | 55-010581 | 1/1980 |
| JP | 55-010583 | 1/1980 |
| JP | 55-010584 | 1/1980 |
| JP | 55-012406 | 1/1980 |
| JP | 56-163447 | 12/1981 |
| JP | 57-070448 | 4/1982 |
| JP | 60-173457 | 9/1985 |
| JP | 60-173458 | 9/1985 |
| JP | 60-173459 | 9/1985 |
| JP | 61-090050 | 5/1986 |
| JP | 62-085855 | 4/1987 |
| JP | 62-114747 | 5/1987 |
| JP | 63-058149 | 3/1988 |
| JP | 63-128252 | 5/1988 |
| JP | 63-139246 | 6/1988 |
| JP | 63-294799 | 12/1988 |
| JP | 63-317757 | 12/1988 |
| JP | 63-317758 | 12/1988 |
| JP | 1-114746 | 5/1989 |
| JP | 1-114747 | 5/1989 |
| JP | 1-124060 | 5/1989 |
| JP | 1-134244 | 5/1989 |
| JP | 1-156658 | 6/1989 |
| JP | 2-062958 | 3/1990 |
| JP | 2-120655 | 5/1990 |
| JP | 2-287145 | 11/1990 |
| JP | 2-310457 | 12/1990 |
| JP | 3-026956 | 2/1991 |
| JP | 3-028752 | 2/1991 |
| JP | 3-202764 | 9/1991 |
| JP | 5-072171 | 3/1993 |
| JP | 5-196595 | 8/1993 |
| JP | 6-190050 | 7/1994 |
| JP | 7-055757 | 3/1995 |
| JP | 7-072585 | 3/1995 |
| JP | 8-285814 | 11/1996 |
| JP | 8-285815 | 11/1996 |
| JP | 9-021778 | 1/1997 |
| JP | 9-101280 | 4/1997 |
| JP | 9-285459 | 11/1997 |
| JP | 10-170471 | 6/1998 |
| JP | 11-506629 | 6/1999 |
| JP | 2004-520103 | 7/2004 |
| JP | 2004-520898 | 7/2004 |
| SU | 1281988 A1 | 1/1987 |
| WO | WO-1985/005119 | 11/1985 |
| WO | WO-1989/008713 | 9/1989 |
| WO | WO-1990/005300 | 5/1990 |
| WO | WO-1990/005910 | 5/1990 |
| WO | WO-1991/001680 | 2/1991 |
| WO | WO-1991/004704 | 4/1991 |
| WO | WO-1991/015993 | 10/1991 |
| WO | WO-1992/013271 | 8/1992 |
| WO | WO-1994/020602 | 9/1994 |
| WO | WO-1994/027140 | 11/1994 |
| WO | WO-1996/039977 | 5/1996 |
| WO | WO-1996/025089 | 8/1996 |
| WO | WO-1996/030431 | 10/1996 |
| WO | WO-1996/035370 | 11/1996 |
| WO | WO-1997/002847 | 1/1997 |
| WO | WO-1997/019344 | 5/1997 |
| WO | WO-1997/042882 | 11/1997 |
| WO | WO-1997/042883 | 11/1997 |
| WO | WO-1997/042886 | 11/1997 |
| WO | WO-1997/042888 | 11/1997 |
| WO | WO-1997/043962 | 11/1997 |
| WO | WO-1998/035053 | 8/1998 |
| WO | WO-1998/056293 | 12/1998 |
| WO | WO-1999/033504 | 7/1999 |
| WO | WO-1999/056613 | 11/1999 |
| WO | WO-2000/049940 | 8/2000 |
| WO | WO-2000/059370 | 10/2000 |
| WO | WO-2000/078992 | 12/2000 |
| WO | WO-2001/052935 | 7/2001 |
| WO | WO-2001/054753 | 8/2001 |
| WO | WO-2002/016905 | 2/2002 |
| WO | WO-2002/050534 | 6/2002 |
| WO | WO-2002/058537 | 8/2002 |
| WO | WO-2003/028784 | 4/2003 |
| WO | WO-2003/076893 | 9/2003 |
| WO | WO-2003/082091 | 10/2003 |
| WO | WO-2004/028337 | 4/2004 |
| WO | WO-2004/060436 | 7/2004 |
| WO | WO-2004/061420 | 7/2004 |
| WO | WO-2004/098684 | 11/2004 |
| WO | WO-2004/112602 | 12/2004 |
| WO | WO-2005/084534 | 9/2005 |
| WO | WO-2005/089103 | 9/2005 |
| WO | WO-2006/024671 | 3/2006 |
| WO | WO-2006/042811 | 4/2006 |
| WO | WO-2006/108809 | 10/2006 |
| WO | WO-2007/089738 | 8/2007 |
| WO | WO-2007/140783 | 12/2007 |
| WO | WO-2008/065646 | 6/2008 |
| WO | WO-2008/133702 | 11/2008 |
| WO | WO-2009/062675 | 5/2009 |
| WO | WO-2009/068661 | 6/2009 |

(56) References Cited

FOREIGN PATENT DOCUMENTS

| WO | WO-2010/112521 | 10/2010 |
|----|----------------|---------|
| WO | WO-2011/002815 | 1/2011  |

OTHER PUBLICATIONS

Albery, W. J., et al., "Amperometric Enzyme Electrodes Part II: Conducting Salts as Electrode Materials for the Oxidation of Glucose Oxidase", *Journal of ElectroAnalytical Chemistry*, vol. 194, 1985, pp. 223-235.
Albery, W. J., et al., "Amperometric Enzyme Electrodes", *Philosophical Transactions of The Royal Society of London*, vol. 316, 1987, pp. 107-119.
Alcock, S. J., et al., "Continuous Analyte Monitoring to Aid Clinical Practice", *IEEE Engineering in Medicine and Biology Magazine*, 1994, pp. 319-325.
Anderson, L. B., et al., "Thin-Layer Electrochemistry: Steady-State Methods of Studying Rate Processes", *Journal of ElectroAnalytical Chemistry*, vol. 10, 1965, pp. 295-305.
Armour, J. C., et al., "Application of Chronic Intravascular Blood Glucose Sensor in Dogs", *Diabetes*, vol. 39, 1990, pp. 1519-1526.
Aussedat, B., et al., "A User-Friendly Method for Calibrating a Subcutaneous Glucose Sensor-Based Hypoglycemic Alarm", *Biosensors & Bioelectronics*, vol. 12, No. 11, 1997, pp. 1061-1071.
Bartlett, P. N., et al., "Covalent Binding of Electron Relays to Glucose Oxidase", *Journal of the Chemical Society, Chemical Communications*, 1987, pp. 1603-1604.
Bartlett, P. N., et al., "Modification of Glucose Oxidase by Tetrathiafulvalene", *Journal of the Chemical Society, Chemical Communications*, 1990, pp. 1135-1136.
Bennion, N., et al., "Alternate Site Glucose Testing: A Crossover Design", *Diabetes Technology & Therapeutics*, vol. 4, No. 1, 2002, pp. 25-33.
Bindra, D. S., et al., "Design and in Vitro Studies of a Needle-Type Glucose Sensor for Subcutaneous Monitoring", *Analytical Chemistry*, vol. 63, No. 17, 1991, pp. 1692-1696.
Bobbioni-Harsch, E., et al., "Lifespan of Subcutaneous Glucose Sensors and Their Performances During Dynamic Glycaemia Changes in Rats", *Journal of Biomedical Engineering*, vol. 15, 1993, pp. 457-463.
Brandt, J., et al., "Covalent Attachment of Proteins to Polysaccharide Carriers by Means of Benzoquinone", *Biochimica et Biophysica Acta*, vol. 386, 1975, pp. 196-202.
Brownlee, M., et al., "A Glucose-Controlled Insulin-Delivery System: Semisynthetic Insulin Bound to Lectin", *Science*, vol. 206, 1979, 1190-1191.
Cass, A. E., et al., "Ferricinum Ion as an Electron Acceptor for Oxido-Reductases", *Journal of ElectroAnalytical Chemistry*, vol. 190, 1985, pp. 117-127.
Cass, A. E., et al., "Ferrocene-Medicated Enzyme Electrode for Amperometric Determination of Glucose", *Analytical Chemistry*, vol. 56, No. 4, 1984, 667-671.
Castner, J. F., et al., "Mass Transport and Reaction Kinetic Parameters Determined Electrochemically for Immobilized Glucose Oxidase", *Biochemistry*, vol. 23 No. 10, 1984, 2203-2210.
Claremont, D. J., et al., "Biosensors for Continuous In Vivo Glucose Monitoring", *Proceedings of the Annual International Conference of the IEEE Engineering in Medicine and Biology Society*, vol. 10, 1988.
Clark Jr., L. C., et al., "Differential Anodic Enzyme Polarography for the Measurement of Glucose", *Oxygen Transport to Tissue: Instrumentation, Methods, and Physiology*, 1973, pp. 127-133.
Clark Jr., L. C., et al., "Electrode Systems for Continuous Monitoring in Cardiovascular Surgery", *Annals New York Academy of Sciences*, 1962, pp. 29-45.
Clark Jr., L. C., et al., "Long-term Stability of Electroenzymatic Glucose Sensors Implanted in Mice", *American Society of Artificial Internal Organs Transactions*, vol. XXXIV, 1988, pp. 259-265.

Clarke, W. L., et al., "Evaluating Clinical Accuracy of Systems for Self-Monitoring of Blood Glucose", *Diabetes Care*, vol. 10, No. 5, 1987, pp. 622-628.
Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.
Csoregi, E., et al., "Design, Characterization, and One-Point in Vivo Calibration of a Subcutaneously Implanted Glucose Electrode", *Analytical Chemistry*, vol. 66 No. 19, 1994, pp. 3131-3138.
Csoregi, E., et al., "On-Line Glucose Monitoring by Using Microdialysis Sampling and Amperometric Detection Based on 'Wired' Glucose Oxidase in Carbon Paste", *Mikrochimica Acta*, vol. 121, 1995, pp. 31-40.
Davis, G., "Electrochemical Techniques for the Development of Amperometric Biosensors", *Biosensors*, vol. 1, 1985, pp. 161-178.
Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", *The Journal of Physical Chemistry*, vol. 91, No. 6, 1987, pp. 1285-1289.
Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", *Journal of the American Chemical Society*, vol. 110, No. 8, 1988, pp. 2615-2620.
Degani, Y., et al., "Electrical Communication Between Redox Centers of Glucose Oxidase and Electrodes via Electrostatically and Covalently Bound Redox Polymers", *Journal of the American Chemical Society*, vol. 111, 1989, pp. 2357-2358.
Denisevich, P., et al., "Unidirectional Current Flow and Charge State Trapping at Redox Polymer Interfaces on Bilayer Electrodes: Principles, Experimental Demonstration, and Theory", *Journal of the American Chemical Society*, vol. 103, 1981, pp. 4727-4737.
Dicks, J. M., et al., "Ferrocene Modified Polypyrrole with Immobilised Glucose Oxidase and its Application in Amperometric Glucose Microbiosensors", *Annales de Biologie Clinique*, vol. 47, 1989, pp. 607-619.
Ellis, C. D., et al., "Selectivity and Directed Charge Transfer through an Electroactive Metallopolymer Film", *Journal of the American Chemical Society*, vol. 103, No. 25, 1981, pp. 7480-7483.
Engstrom, R. C., "Electrochemical Pretreatment of Glassy Carbon Electrodes", *Analytical Chemistry*, vol. 54, No. 13, 1982, pp. 2310-2314.
Engstrom, R. C., et al., "Characterization of Electrochemically Pretreated Glassy Carbon Electrodes", *Analytical Chemistry*, vol. 56, No. 2, 1984, pp. 136-141.
Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.
Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.
Feldman, B., et al., "Electron Transfer Kinetics at Redox Polymer/Solution Interfaces Using Microelectrodes and Twin Electrode Thin Layer Cells", *Journal of ElectroAnalytical Chemistry*, vol. 194, 1985, pp. 63-81.
Fischer, H., et al., "Intramolecular Electron Transfer Medicated by 4,4'-Bypyridine and Related Bridging Groups", *Journal of the American Chemical Society*, vol. 98, No. 18, 1976, pp. 5512-5517.
Foulds, N. C., et al., "Enzyme Entrapment in Electrically Conducting Polymers: Immobilisation of Glucose Oxidase in Polypyrrole and its Application in Amperometric Glucose Sensors", *Journal of the Chemical Society, Faraday Transactions 1*, vol. 82, 1986, pp. 1259-1264.
Foulds, N. C., et al., "Immobilization of Glucose Oxidase in Ferrocene-Modified Pyrrole Polymers", *Analytical Chemistry*, vol. 60, No. 22, 1988, pp. 2473-2478.
Freedman, D., et al. *Statistics: Second Edition*, 1991, pp. 74.

(56) References Cited

OTHER PUBLICATIONS

Frew, J. E., et al., "Electron-Transfer Biosensors", *Philosophical Transactions of The Royal Society of London*, vol. 316, 1987, pp. 95-106.
Gorton, L., et al., "Selective Detection in Flow Analysis Based on the Combination of Immobilized Enzymes and Chemically Modified Electrodes", *Analytica Chimica Acta*, vol. 250, 1991, pp. 203-248.
Gregg, B. A., et al., "Cross-Linked Redox Gels Containing Glucose Oxidase for Amperometric Bionsensor Applications", *Analytical Chemistry*, vol. 62, No. 3, 1990, pp. 258-263.
Gregg, B. A., et al., "Redox Polymer Films Containing Enzymes. 1. A Redox-Conducting Epoxy Cement: Synthesis, Characterization, and Electrocatalytic Oxidation of Hydroquinone", *Journal of Physical Chemistry*, vol. 95, No. 15, 1991, 5970-5975.
Gunasingham, et al., "Electrochemically Modulated Optrode for Glucose", *Biosensors & Bioelectronics*, vol. 7, 1992, pp. 353-359.
Hale, P. D., et al., "A New Class of Amperometric Biosensor Incorporating a Polymeric Electron-Transfer Mediator", *Journal of the American Chemical Society*, vol. 111, No. 9, 1989, pp. 3482-3484.
Harrison, D. J., et al., "Characterization of Perfluorosulfonic Acid Polymer Coated Enzyme Electrodes and a Miniatureized Integrated Potentiostat for Glucose Analysis in Whole Blood", *Analytical Chemistry*, vol. 60, No. 19, 1988, pp. 2002-2007.
Hawkridge, F. M., et al., "Indirect Coulometric Titration of Biological Electron Transport Components", *Analytical Chemistry*, vol. 45, No. 7, 1973, pp. 1021-1027.
Heller, A., "Electrical Connection Enzyme Redox Centers to Electrodes", *Journal of Physical Chemistry*, vol. 96, No. 9, 1990, pp. 3579-3587.
Heller, A., "Electrical Wiring of Redox Enzymes", *Accounts of Chemical Research* vol. 23, No. 5, 1990, 128-134.
Heller, A., et al., "Amperometric Biosensors Based on Three-Dimensional Hydrogel-Forming Epoxy Networks", *Sensors and Actuators B*, vol. 13-14, 1993, pp. 180-183.
Hoel, P., *Elementary Statistics: Fourth Edition*, 1976, pp. 113-114.
Ianniello, R. M., et al., "Differential Pulse Voltammetric Study of Direct Electron Transfer in Glucose Oxidase Chemically Modified Graphite Electrodes", *Analytical Chemistry*, vol. 54, No. 7, 1982, pp. 1098-1101.
Ianniello, R. M., et al., "Immobilized Enzyme Chemically Modified Electrode as an Amperometric Sensor", *Analytical Chemistry*, vol. 53, No. 13, 1981, pp. 2090-2095.
Ikeda, T., et al., "Artificial Pancreas—Investigation of the Stability of Glucose Sensors Using a Telemetry System" (English language translation of abstract), Jpn. J. Artif. Organs, vol. 19, No. 2, 1990, 889-892.
Ikeda, T., et al., "Glucose Oxidase-Immobilized Benzoquinone-Carbon Paste Electrode as a Glucose Sensor", *Agricultural and Biological Chemistry*, vol. 49, No. 2, 1985, pp. 541-543.
Ikeda, T., et al., "Kinetics of Outer-Sphere Electron Transfers Between Metal Complexes in Solutions and Polymeric Films on Modified Electrodes", *Journal of the American Chemical Society*, vol. 103, No. 25, 1981, pp. 7422-7425.
Isermann, R., "Supervision, Fault-Detection and Fault-Diagnosis Methods—An Introduction", *Control Engineering Practice*, vol. 5, No. 5, 1997, pp. 639-652.
Isermann, R., et al., "Trends in the Application of Model-Based Fault Detection and Diagnosis of Technical Processes", *Control Engineering Practice*, vol. 5, No. 5, 1997, pp. 709-719.
Johnson, J. M., et al., "Potential-Dependent Enzymatic Activity in an Enzyme Thin-Layer Cell", *Analytical Chemistry*, vol. 54, No. 8, 1982, pp. 1377-1383.
Johnson, K. W., "Reproducible Electrodeposition of Biomolecules for the Fabrication of Miniature Electroenzymatic Biosensors", *Sensors and Actuators B*, vol. 5, 1991, pp. 85-89.
Johnson, K. W., et al., "In vivo Evaluation of an Electroenzymatic Glucose Sensor Implanted in Subcutaneous Tissue", *Biosensors & Bioelectronics*, vol. 7, 1992, pp. 709-714.
Johnson, P. C., "Peripheral Circulation", John Wiley & Sons, 1978, pp. 198.
Jonsson, G., et al., "An Amperometric Glucose Sensor Made by Modification of a Graphite Electrode Surface With Immobilized Glucose Oxidase and Adsorbed Mediator", *Biosensors*, vol. 1, 1985, pp. 355-368.
Josowicz, M., et al., "Electrochemical Pretreatment of Thin Film Platinum Electrodes", *Journal of the Electrochemical Society*, vol. 135 No. 1, 1988, pp. 112-115.
Jungheim, K., et al., "How Rapid Does Glucose Concentration Change in Daily Life of Patients with Type 1 Diabetes?", 2002, pp. 250.
Jungheim, K., et al., "Risky Delay of Hypoglycemia Detection by Glucose Monitoring at the Arm", *Diabetes Care*, vol. 24, No. 7, 2001, pp. 1303-1304.
Katakis, I., et al., "Electrostatic Control of the Electron Transfer Enabling Binding of Recombinant Glucose Oxidase and Redox Polyelectrolytes", *Journal of the American Chemical Society*, vol. 116, No. 8, 1994, pp. 3617-3618.
Katakis, I., et al., "L-α-Glycerophosphate and L-Lactate Electrodes Based on the Electrochemical 'Wiring' of Oxidases", *Analytical Chemistry*, vol. 64, No. 9, 1992, pp. 1008-1013.
Kenausis, G., et al., "'Wiring' of Glucose Oxidase and Lactate Oxidase Within a Hydrogel Made with Poly(vinyl pyridine) complexed with $[Os(4,4'-dimethoxy-2,2'-bipyridine)_2Cl]^{+/2+}$", *Journal of the Chemical Society, Faraday Transactions*, vol. 92, No. 20, 1996, pp. 4131-4136.
Koudelka, M., et al., "In-Vivo Behaviour of Hypodermically Implanted Microfabricated Glucose Sensors", *Biosensors & Bioelectronics*, vol. 6, 1991, pp. 31-36.
Kulys, J., et al., "Mediatorless Peroxidase Electrode and Preparation of Bienzyme Sensors", *Bioelectrochemistry and Bioenergetics*, vol. 24, 1990, pp. 305-311.
Lager, W., et al., "Implantable Electrocatalytic Glucose Sensor", *Holmone Metabolic Research*, vol. 26, 1994, pp. 526-530.
Lindner, E., et al., "Flexible (Kapton-Based) Microsensor Arrays of High Stability for Cardiovascular Applications", *Journal of the Chemical Society, Faraday Transactions*, vol. 89, No. 2, 1993, pp. 361-367.
Maidan, R., et al., "Elimination of Electrooxidizable Interferant-Produced Currents in Amperometric Biosensors", *Analytical Chemistry*, vol. 64, No. 23, 1992, pp. 2889-2896.
Mastrototaro, J. J., et al., "An Electroenzymatic Glucose Sensor Fabricated on a Flexible Substrate", *Sensors and Actuators B*, vol. 5, 1991, pp. 139-144.
McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.
McNeil, C. J., et al., "Thermostable Reduced Nicotinamide Adenine Dinucleotide Oxidase: Application to Amperometric Enzyme Assay", *Analytical Chemistry*, vol. 61, No. 1, 1989, pp. 25-29.
Minimed Technologies, "Tape Tips and Other Infusion Site Information", 1995.
Miyawaki, O., et al., "Electrochemical and Glucose Oxidase Coenzyme Activity of Flavin Adenine Dinucleotide Covalently Attached to Glassy Carbon at the Adenine Amino Group", *Biochimica et Biophysica Acta*, vol. 838, 1985, pp. 60-68.
Moatti-Sirat, D., et al., "Evaluating In Vitro and In Vivo the Interference of Ascorbate and Acetaminophen on Glucose Detection by a Needle-Type Glucose Sensor", *Biosensors & Bioelectronics*, vol. 7, 1992, pp. 345-352.
Moatti-Sirat, D., et al., "Reduction of Acetaminophen Interference in Glucose Sensors by a Composite Nafion Membrane: Demonstration in Rats and Man", *Diabetologia*, vol. 37, 1994, pp. 610-616.
Moatti-Sirat, D., et al., "Towards Continuous Glucose Monitoring: In Vivo Evaluation of a Miniaturized Glucose Sensor Implanted for Several Days in Rat Subcutaneous Tissue", *Diabetologia*, vol. 35, 1992, pp. 224-330.
Nagy, G., et al., "A New Type of Enzyme Electrode: The Ascorbic Acid Eliminator Electrode", *Life Sciences*, vol. 31, No. 23, 1982, pp. 2611-2616.

(56) References Cited

OTHER PUBLICATIONS

Nakamura, S., et al., "Effect of Periodate Oxidation on the Structure and Properties of Glucose Oxidase", *Biochimica et Biophysica Acta.*, vol. 445, 1976, pp. 294-308.

Narasimham, K., et al., "p-Benzoquinone Activation of Metal Oxide Electrodes for Attachment of Enzymes", *Enzyme and Microbial Technology*, vol. 7, 1985, pp. 283-286.

OHara, T. J., "Osmium Bipyridyl Redox Polymers Used in Enzyme Electrodes", *Platinum Metals Review*, vol. 39, No. 2, 1995, pp. 54-62.

OHara, T. J., et al., "'Wired' Enzyme Electrodes for Amperometric Determination of Glucose or Lactate in the Presence of Interfering Substances", *Analytical Chemistry*, vol. 66, No. 15, 1994, pp. 2451-2457.

OHara, T. J., et al., "Glucose Electrodes Based on Cross-Linked $[Os(bpy)_2Cl]^{+/2+}$ Complexed Poly(1-Vinylimidazole) Films", *Analytical Chemistry*, vol. 65, No. 23, 1993, pp. 3512-3517.

Olievier, C. N., et al., "In Vivo Measurement of Carbon Dioxide Tension with a Miniature Electrodes", *Pflugers Archiv: European Journal of Physiology*, vol. 373, 1978, pp. 269-272.

Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", *Journal of ElectroAnalytical Chemistry*, vol. 260, 1989, pp. 487-494.

Palleschi, G., et al., "A Study of Interferences in Glucose Measurements in Blood by Hydrogen Peroxide Based Glucose Probes", *Analytical Biochemistry*, vol. 159, 1986, pp. 114-121.

Pankratov, I., et al., "Sol-Gel Derived Renewable-Surface Biosensors", *Journal of ElectroAnalytical Chemistry*, vol. 393, 1995, pp. 35-41.

Pathak, C., et al., "Rapid Photopolymerization of Immunoprotective Gels in Contact with Cells and Tissue", *Journal of the American Chemical Society*, vol. 114, No. 21, 1992, pp. 8311-8312.

Pickup, J., "Developing Glucose Sensors for In Vivo Use", *Tibtech*, vol. 11, 1993, pp. 285-291.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pickup, J., et al., "Potentially-Implantable, Amperometric Glucose Sensors with Mediated Electron Transfer: Improving the Operating Stability", *Biosensors*, vol. 4, 1989, pp. 109-119.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", *Diabetolgia*, vol. 36, 1993, pp. 658-663.

Poitout, V., et al., "Calibration in Dogs of a Subcutaneous Miniaturized Glucose Sensor Using a Glucose Meter for Blood Glucose Determination", *Biosensors & Bioelectronics*, vol. 7, 1992, pp. 587-592.

Poitout, V., et al., "In Vitro and In Vivo Evaluation in Dogs of a Miniaturized Glucose Sensor", *ASAIO Transactions*, vol. 37, No. 3, 1991, pp. M298-M300.

Pollak, A., et al., "Enzyme Immobilization by Condensation Copolymerization into Cross-Linked Polyacrylamide Gels", *Journal of the American Chemical Society*, vol. 102, No. 20, 1980, pp. 6324-6336.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Reach, G., et al., "Can Continuous Glucose Monitoring Be Used for the Treatment of Diabetes?", *Analytical Chemistry*, vol. 64, No. 6, 1992, pp. 381-386.

Rebrin, K., et al., "Automated Feedback Control of Subcutaneous Glucose Concentration in Diabetic Dogs", *Diabetologia*, vol. 32, 1989, pp. 573-576.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Samuels, G. J., et al., "An Electrode-Supported Oxidation Catalyst Based on Ruthenium (IV). pH 'Encapsulation' in a Polymer Film", *Journal of the American Chemical Society*, vol. 103, No. 2, 1981, pp. 307-312.

Sasso, S. V., et al., "Electropolymerized 1,2-Diaminobenzene as a Means to Prevent Interferences and Fouling and to Stabilize Immobilized Enzyme in Electrochemical Biosensors", *Analytical Chemistry*, vol. 62, No. 11, 1990, pp. 1111-1117.

Scheller, F., et al., "Enzyme Electrodes and Their Application", *Philosophical Transactions of The Royal Society of London B*, vol. 316, 1987, pp. 85-94.

Schmehl, R. H., et al., "The Effect of Redox Site Concentration on the Rate of Mediated Oxidation of Solution Substrates by a Redox Copolymer Film", *Journal of ElectroAnalytical Chemistry*, vol. 152, 1983, pp. 97-109.

Schmidt, F. J., et al., "Calibration of a Wearable Glucose Sensor", *The International Journal of Artificial Organs*, vol. 15, No. 1, 1992, pp. 55-61.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sittampalam, G., et al., "Surface-Modified Electrochemical Detector for Liquid Chromatography", *Analytical Chemistry*, vol. 55, No. 9, 1983, pp. 1608-1610.

Soegijoko, S., et al., "External Artificial Pancreas: A New Control Unit Using Microprocessor", *Hormone and Metabolic Research Supplement Series*, vol. 12, 1982, pp. 165-169.

Sprules, S. D., et al., "Evaluation of a New Disposable Screen-Printed Sensor Strip for the Measurement of NADH and Its Modi-

(56) References Cited

OTHER PUBLICATIONS fication to Produce a Lactate Biosensor Employing Microliter Volumes", *Electroanalysis*, vol. 8, No. 6, 1996, pp. 539-543.
Sternberg, F., et al., "Calibration Problems of Subcutaneous Glucosensors when Applied 'In-Situ' in Man", *Hormone and Metabolic Research*, vol. 26, 1994, pp. 523-526.
Sternberg, R., et al., "Covalent Enzyme Coupling on Cellulose Acetate Membranes for Glucose Sensor Development", *Analytical Chemistry*, vol. 60, No. 24, 1988, pp. 2781-2786.
Sternberg, R., et al., "Study and Development of Multilayer Needle-Type Enzyme-Based Glucose Microsensors", *Biosensors*, vol. 4, 1988, pp. 27-40.
Suekane, M., "Immobilization of Glucose Isomerase", *Zettschrift fur Allgemeine Mikrobiologie*, vol. 22, No. 8, 1982, pp. 565-576.
Tajima, S., et al., "Simultaneous Determination of Glucose and 1,5-Anydroglucitol", *Chemical Abstracts*, vol. 111, No. 25, 1989, pp. 394.
Tarasevich, M. R., "Bioelectrocatalysis", *Comprehensive Treatise of Electrochemistry*, vol. 10, 1985, pp. 231-295.
Tatsuma, T., et al., "Enzyme Monolayer- and Bilayer-Modified Tin Oxide Electrodes for the Determination of Hydrogen Peroxide and Glucose", *Analytical Chemistry*, vol. 61, No. 21, 1989, pp. 2352-2355.
Taylor, C., et al., "'Wiring' of Glucose Oxidase Within a Hydrogel Made with Polyvinyl Imidazole Complexed with [(Os-4,4'-dimethoxy-2,2'-bipyridine)Cl]$^{+/2+}$", *Journal of ElectroAnalytical Chemistry*, vol. 396, 1995, pp. 511-515.
Thompson, M., et al., "In Vivo Probes: Problems and Perspectives", *Clinical Biochemistry*, vol. 19, 1986, pp. 255-261.
Trojanowicz, M., et al., "Enzyme Entrapped Polypyrrole Modified Electrode for Flow-Injection Determination of Glucose", *Biosensors & Bioelectronics*, vol. 5, 1990, pp. 149-156.
Turner, A., et al., "Diabetes Mellitus: Biosensors for Research and Management", *Biosensors*, vol. 1, 1985, pp. 85-115.
Turner, R. F., et al., "A Biocompatible Enzyme Electrode for Continuous in vivo Glucose Monitoring in Whole Blood", *Sensors and Actuators B*, vol. 1, 1990, pp. 561-564.
Tuzhi, P., et al., "Constant Potential Pretreatment of Carbon Fiber Electrodes for In Vivo Electrochemistry", *Analytical Letters*, vol. 24, No. 6, 1991, pp. 935-945.
Umana, M., "Protein-Modified Electrochemically Active Biomaterial Surface", *U.S. Army Research Office, Analytical and Chemical Sciences Research Triangle Institute*, 1988, pp. 1-9.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Urban, G., et al., "Miniaturized Thin-Film Biosensors Using Covalently Immobilized Glucose Oxidase", *Biosensors & Bioelectronics*, vol. 6, 1991, pp. 555-562.
Velho, G., et al., "In Vitro and In Vivo Stability of Electrode Potentials in Needle-Type Glucose Sensors", *Diabetes*, vol. 38, No. 2, 1989, pp. 164-171.
Velho, G., et al., "Strategies for Calibrating a Subcutaneous Glucose Sensor", *Biomedica Biochimica Acta*, vol. 48, 1989, pp. 957-964.
Von Woedtke, T., et al., "In Situ Calibration of Implanted Electrochemical Glucose Sensors", *Biomedica Biochimica Acta*, vol. 48, 1989, pp. 943-952.
Vreeke, M. S., et al., "Hydrogen Peroxide Electrodes Based on Electrical Connection of Redox Centers of Various Peroxidases to Electrodes through a Three-Dimensional Electron-Relaying Polymer Network", *Diagnostic Biosensors Polymers*, Chapter 15, 1993, pp. 180-193.
Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", *Analytical Chemistry*, vol. 64, No. 24, 1992, pp. 3084-3090.

Wang, D. L., et al., "Miniaturized Flexible Amperometric Lactate Probe", *Analytical Chemistry*, vol. 65, No. 8, 1993, pp. 1069-1073.
Wang, J., et al., "Activation of Glassy Carbon Electrodes by Alternating Current Electrochemical Treatment", *Analytica Chimica Acta*, vol. 167, 1985, pp. 325-334.
Wang, J., et al., "Amperometric Biosensing of Organic Peroxides with Peroxidase-Modified Electrodes", *Analytica Chimica Acta*, vol. 254, 1991, pp. 81-88.
Wang, J., et al., "Screen-Printable Sol-Gel Enzyme-Containing Carbon Inks", *Analytical Chemistry*, vol. 68, No. 15, 1996, pp. 2705-2708.
Wang, J., et al., "Sol-Gel-Derived Metal-Dispersed Carbon Composite Amperometric Biosensors", *Electroanalysis*, vol. 9, No. 1, 1997, pp. 52-55.
Williams, D. L., et al., "Electrochemical-Enzymatic Analysis of Blood Glucose and Lactate", *Analytical Chemistry*, vol. 42, No. 1, 1970, pp. 118-121.
Wilson, G. S., et al., "Progress Toward the Development of an Implantable Sensor for Glucose", *Clinical Chemistry*, vol. 38, No. 9, 1992, pp. 1613-1617.
Yabuki, S., et al., "Electro-Conductive Enzyme Membrane", *Journal of the Chemical Society, Chemical Communications*, 1989, pp. 945-946.
Yang, L., et al., "Determination of Oxidase Enzyme Substrates Using Cross-Flow Thin-Layer Amperometry", *Electroanalysis*, vol. 8, No. 8-9, 1996, pp. 716-721.
Yao, S. J., et al., "The Interference of Ascorbate and Urea in Low-Potential Electrochemical Glucose Sensing", *Proceedings of the Twelfth Annual International Conference of the IEEE Engineering in Medicine and Biology Society*, vol. 12, Part 2, 1990, pp. 487-489.
Yao, T., "A Chemically-Modified Enzyme Membrane Electrode as an Amperometric Glucose Sensor", *Analytica Chimica Acta*, vol. 148, 1983, pp. 27-33.
Ye, L., et al., "High Current Density 'Wired' Quinoprotein Glucose Dehydrogenase Electrode", *Analytical Chemistry*, vol. 65, No. 3, 1993, pp. 238-241.
Yildiz, A., et al., "Evaluation of an Improved Thin-Layer Electrode", *Analytical Chemistry*, vol. 40, No. 7, 1968, pp. 1018-1024.
Zamzow, K., et al., "New Wearable Continuous Blood Glucose Monitor (BGM) and Artificial Pancreas (AP)", *Diabetes*, vol. 39, 1990, pp. 5A-20.
Zhang, Y., et al., "Application of Cell Culture Toxicity Tests to the Development of Implantable Biosensors", *Biosensors & Bioelectronics*, vol. 6, 1991, pp. 653-661.
Zhang, Y., et al., "Elimination of the Acetaminophen Interference in an Implantable Glucose Sensor", *Analytical Chemistry*, vol. 66, No. 7, 1994, pp. 1183-1188.
Zhu, J., et al., "Fabrication and Characterization of Glucose Sensors Based on a Microarray H2O2 electrode", *Biosensors & Bioelectronics*, vol. 9, 1994, pp. 295-300.
U.S. Appl. No. 10/703,214, Notice of Allowance dated Feb. 26, 2008.
U.S. Appl. No. 10/703,214, Office Action dated May 16, 2007.
U.S. Appl. No. 10/703,214, Office Action dated Oct. 31, 2006.
U.S. Appl. No. 11/899,870, Notice of Allowance dated May 15, 2009.
U.S. Appl. No. 11/899,870, Office Action dated Feb. 25, 2009.
U.S. Appl. No. 11/899,870, Office Action dated Jun. 18, 2008.
U.S. Appl. No. 11/899,917, Advisory Action dated Jul. 13, 2009.
U.S. Appl. No. 11/899,917, Notice of Allowance dated Jul. 12, 2011.
U.S. Appl. No. 11/899,917, Office Action dated Jun. 20, 2008.
U.S. Appl. No. 11/899,917, Office Action dated Mar. 18, 2010.
U.S. Appl. No. 11/899,917, Office Action dated Mar. 25, 2009.
U.S. Appl. No. 11/899,917, Office Action dated Sep. 1, 2010.
U.S. Appl. No. 12/538,067, Office Action dated Jun. 6, 2013.
U.S. Appl. No. 12/613,516, Office Action dated May 18, 2011.
U.S. Appl. No. 12/613,516, Office Action dated Sep. 15, 2010.
Reexamination U.S. Appl. No. 90/008,172, Request for Reexamination of U.S. Pat. No. 6,990,366, filed Aug. 16, 2006.
Reexamination U.S. Appl. No. 90/008,457, Notice of Intent to Issue Reexamination Certificate dated Mar. 13, 2008.

(56) References Cited

OTHER PUBLICATIONS

Reexamination U.S. Appl. No. 90/008,457, Order Granting Request for Reexamination mailed Feb. 23, 2007.
Reexamination U.S. Appl. No. 90/008,457, Request for Reexamination of U.S. Pat. No. 6,990,366 filed Jan. 23, 2007.
Reexamination U.S. Appl. No. 90/009,104 & U.S. Appl. No. 90/009,328, Notice of Intent to Issue Reexamination Certificate dated Nov. 20, 2009.
Reexamination U.S. Appl. No. 90/009,104 & U.S. Appl. No. 90/009,328, Office Action dated Aug. 4, 2009.
Reexamination U.S. Appl. No. 90/009,104 & U.S. Appl. No. 90/009,328, Office Action dated Sep. 30, 2009.
Reexamination U.S. Appl. No. 90/009,104, Office Action dated Oct. 16, 2008.
Reexamination U.S. Appl. No. 90/009,104, Order Granting Request for Reexamination dated Jun. 5, 2008.
Reexamination U.S. Appl. No. 90/009,104, Request for Reexamination of U.S. Pat. No. 6,990,366 filed Apr. 8, 2008.
Reexamination U.S. Appl. No. 90/009,328, Order Granting Request for Reexamination mailed Dec. 9, 2008.
Reexamination U.S. Appl. No. 90/009,328, Request for Reexamination of U.S. Pat. No. 6,990,366 filed Nov. 10, 2008.
Reexamination U.S. Appl. No. 90/010,791, Notice of Intent to Issue Reexamination Certificate dated May 17, 2011.
Reexamination U.S. Appl. No. 90/010,791, Office Action dated Dec. 17, 2010.
Reexamination U.S. Appl. No. 90/010,791, Office Action dated May 28, 2010.
Reexamination U.S. Appl. No. 90/010,791, Order Granting Request for Reexamination mailed Feb. 22, 2010.
Reexamination U.S. Appl. No. 90/010,791, Request for Reexamination of U.S. Pat. No. 6,990,366 filed Dec. 22, 2009.
Reexamination U.S. Appl. No. 90/011,730, Notice of Intent to Issue Reexam Certificate for U.S. Pat. No. 6,990,366 dated Apr. 5, 2012.
Reexamination U.S. Appl. No. 90/011,730, Office Action dated Jan. 11, 2012.
Reexamination U.S. Appl. No. 90/011,730, Order Granting Request for Reexamination of U.S. Pat. No. 6,990,366 mailed Aug. 24, 2011.
Reexamination U.S. Appl. No. 90/011,730, Request for Reexamination of U.S. Pat. No. 6,990,366 filed Jun. 3, 2011.
Reexamination U.S. Appl. No. 95/002,113, Order Denying Request for Reexamination of U.S. Pat. No. 6,990,366 mailed Nov. 13, 2012.
Reexamination U.S. Appl. No. 95/002,113, Petition for Review of the Order Denying Request Reexamination of U.S. Pat. No. 6,990,366 mailed Dec. 13, 2012.
Reexamination U.S. Appl. No. 95/002,113, Request for Reexamination of U.S. Pat. No. 6,990,366 filed Aug. 30, 2012.
Reexamination U.S. Appl. No. 95/002,162, Order Denying Request for Reexamination of U.S. Pat. No. 8,175,673 mailed Nov. 13, 2012.
Reexamination U.S. Appl. No. 95/002,162, Petition for Review of the Order Denying Request Reexamination of U.S. Pat. No. 8,175,673 mailed Dec. 13, 2012.
Reexamination U.S. Appl. No. 95/002,162, Request for Reexamination of U.S. Pat. No. 8,175,673 filed Sep. 7, 2012.

* cited by examiner

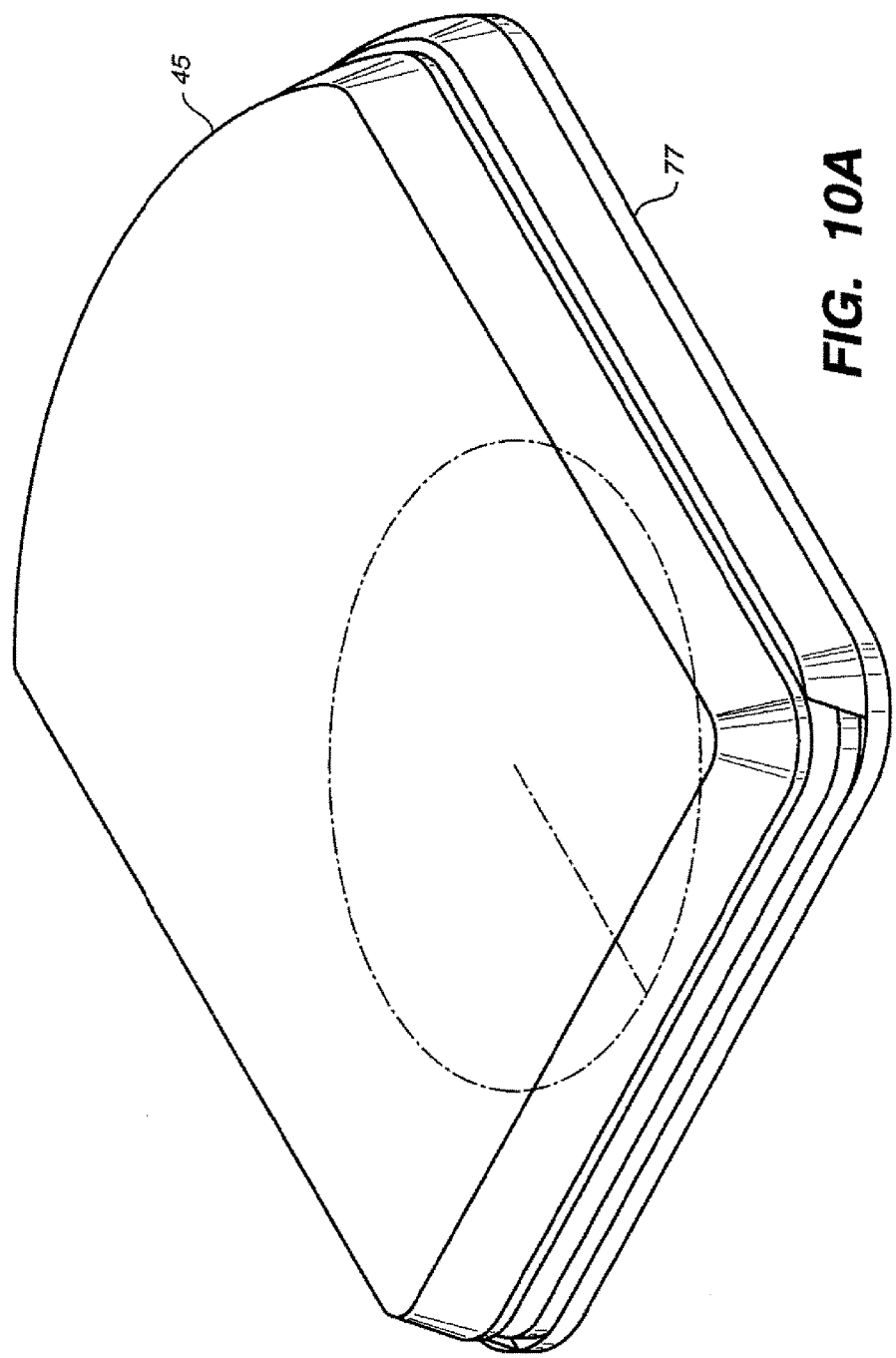

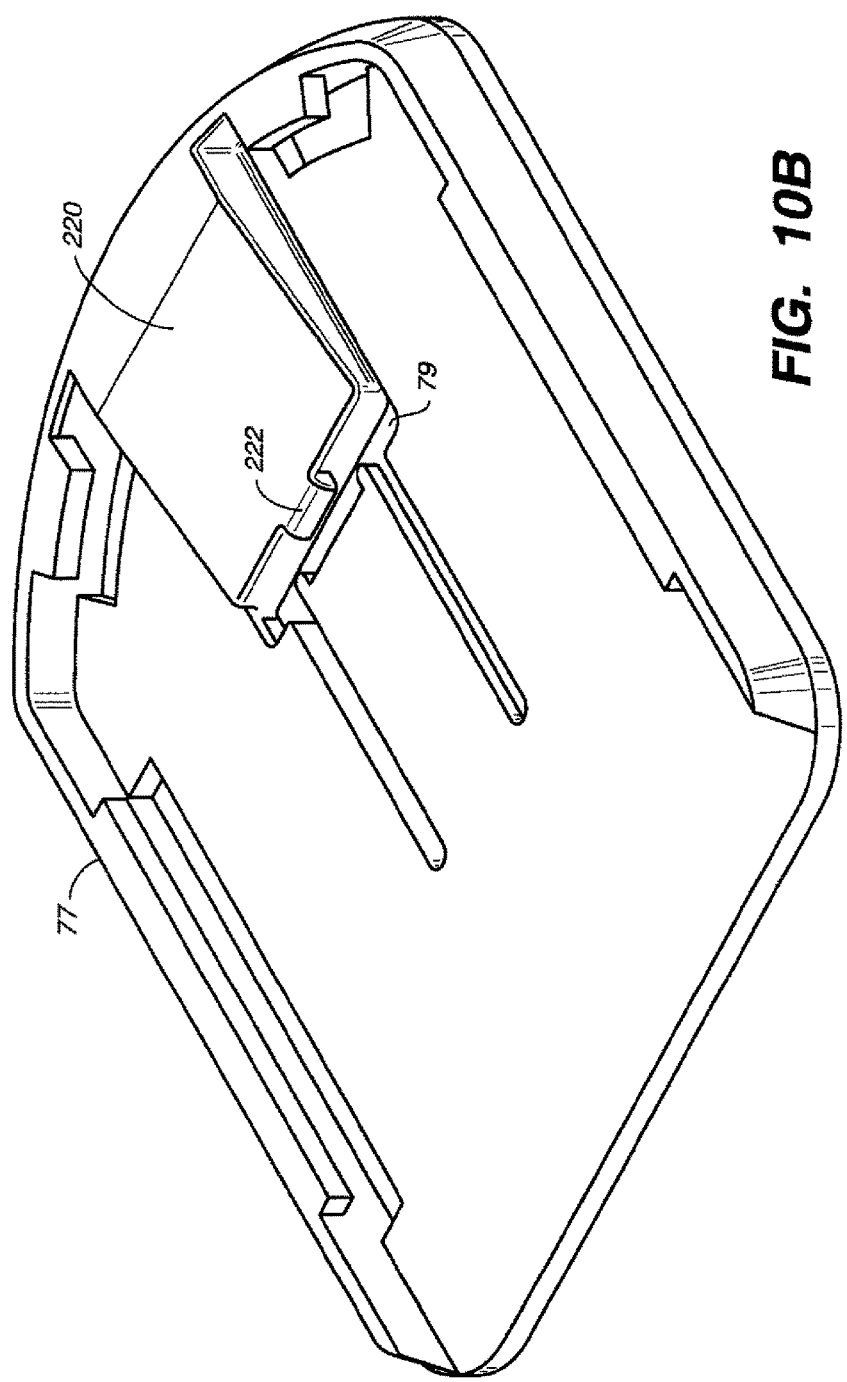

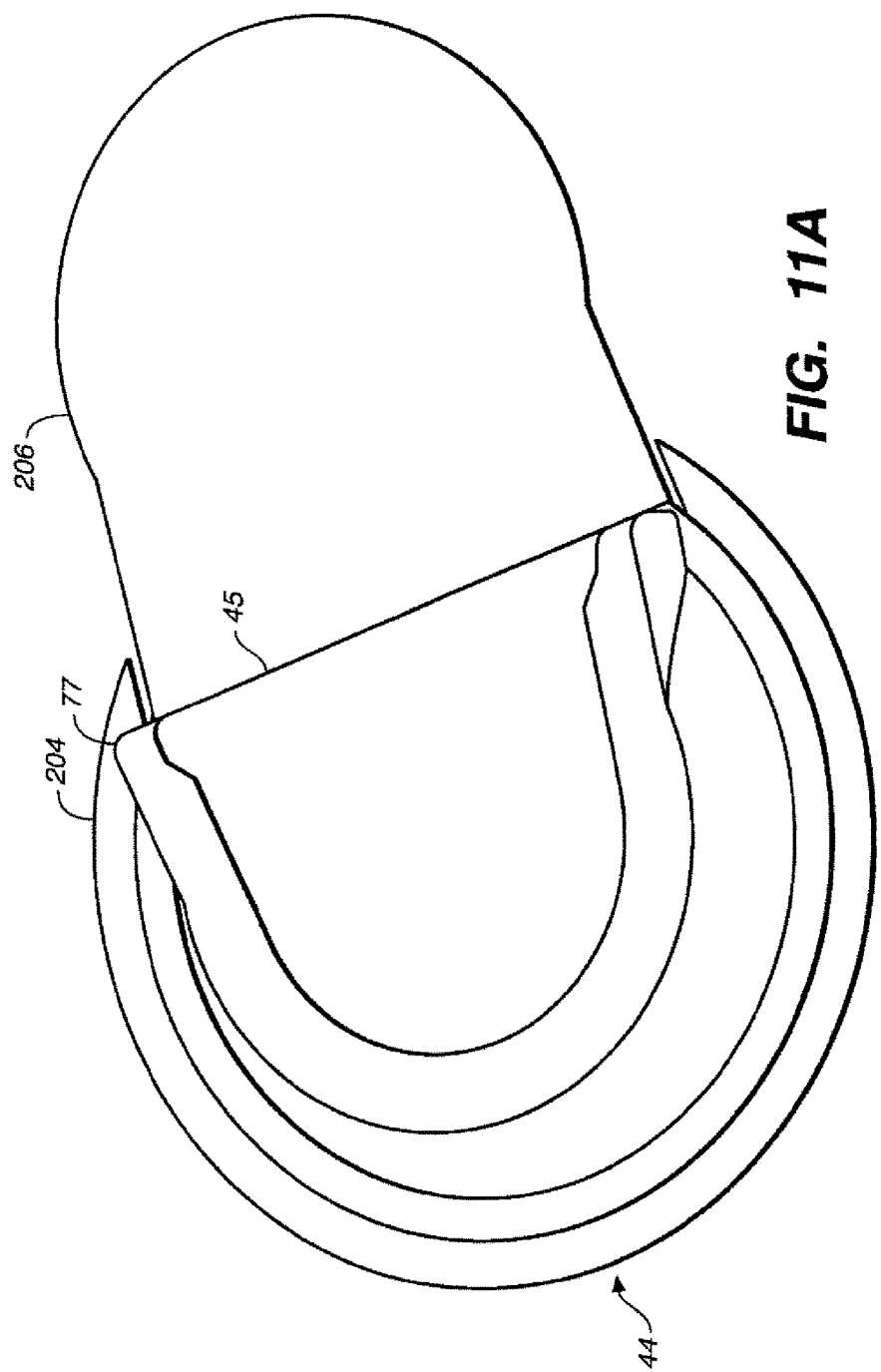

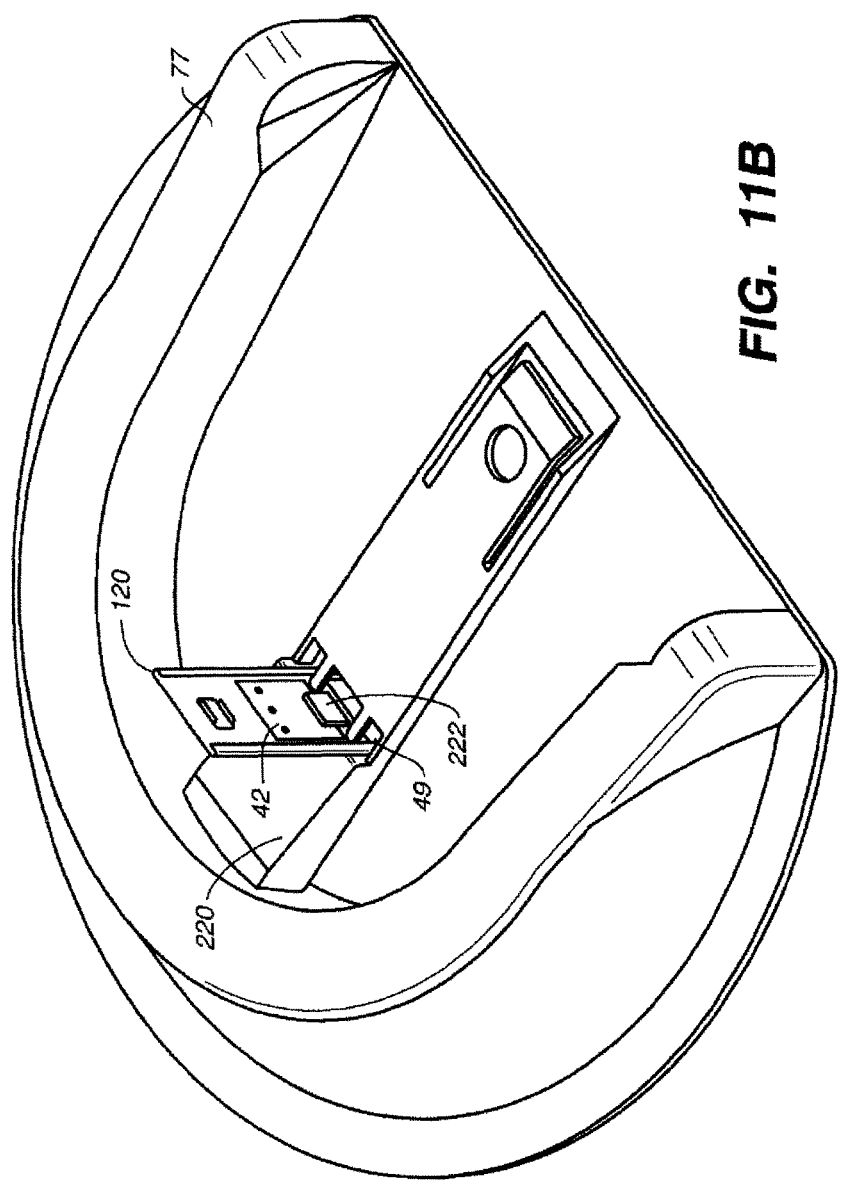

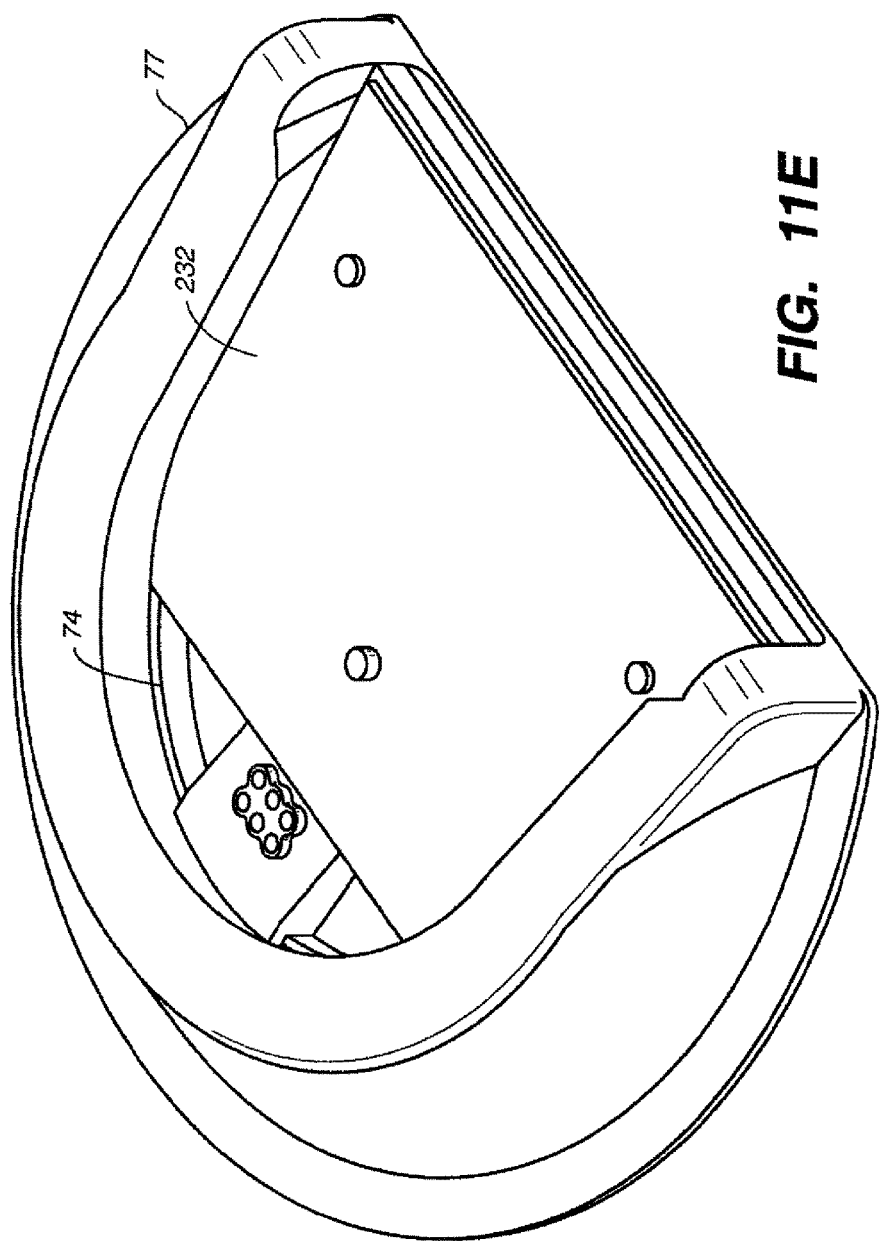

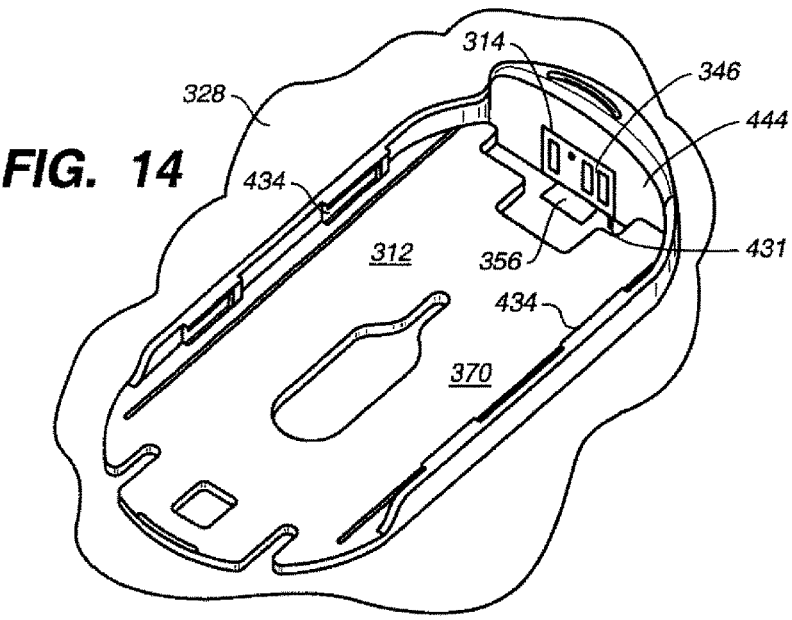
FIG. 14
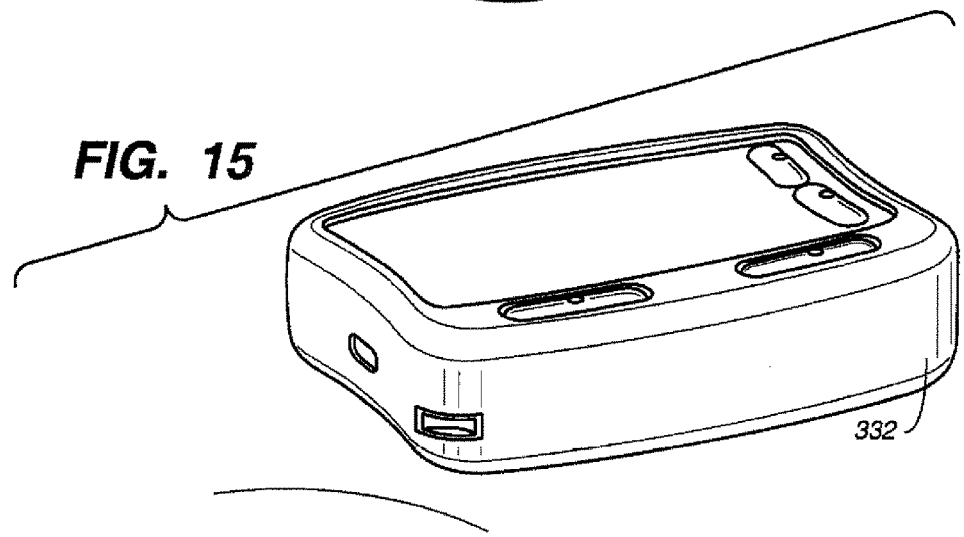
FIG. 15
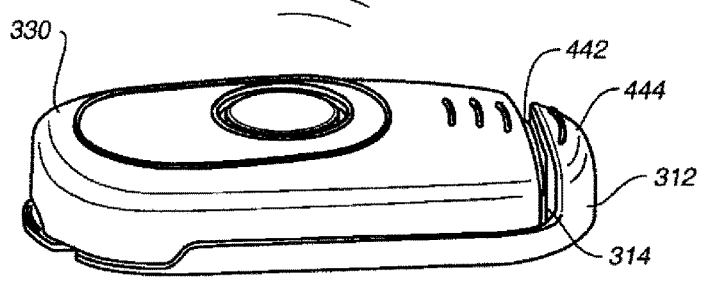

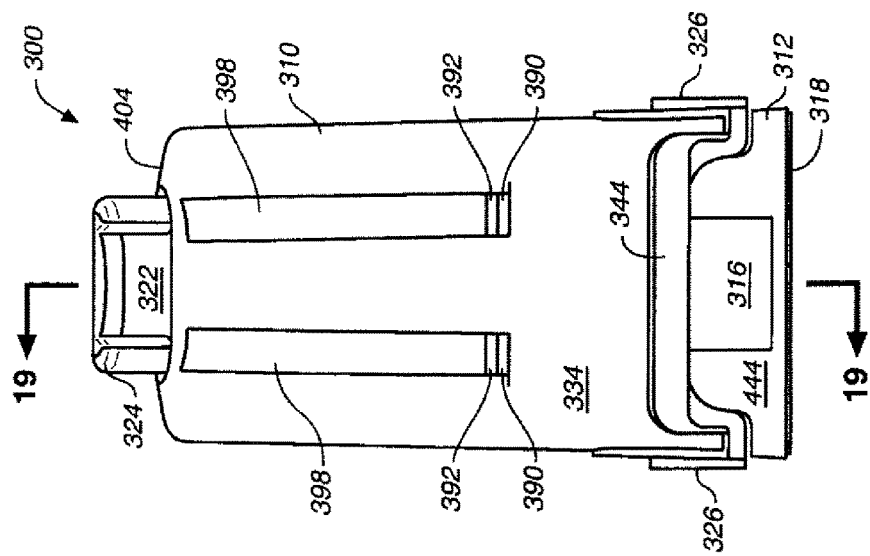
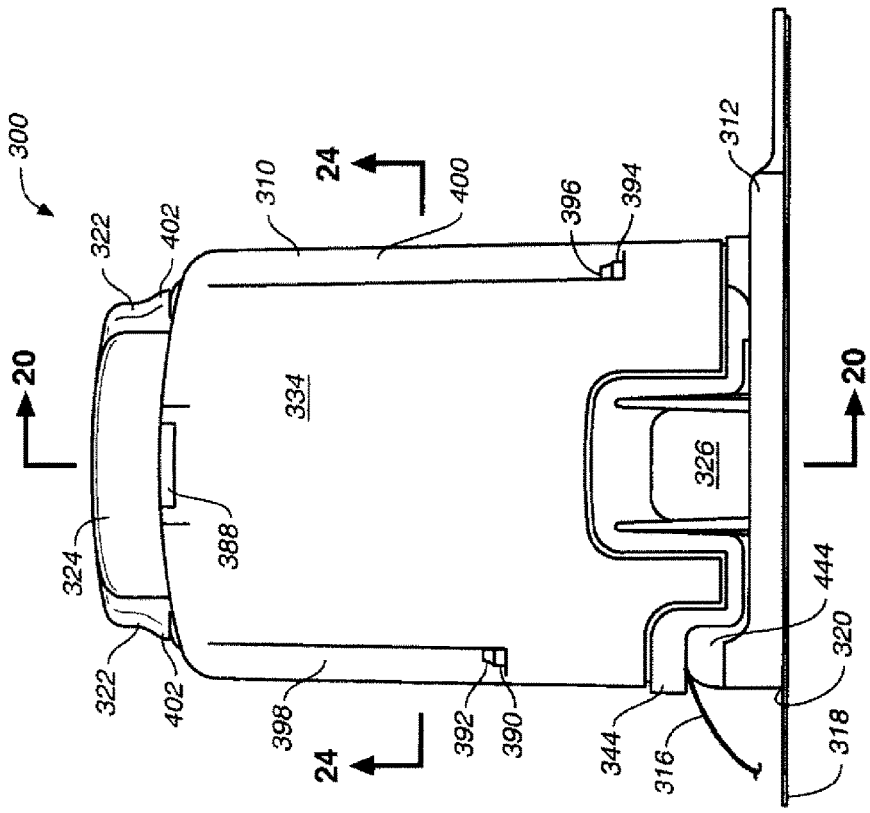
FIG. 18
FIG. 17

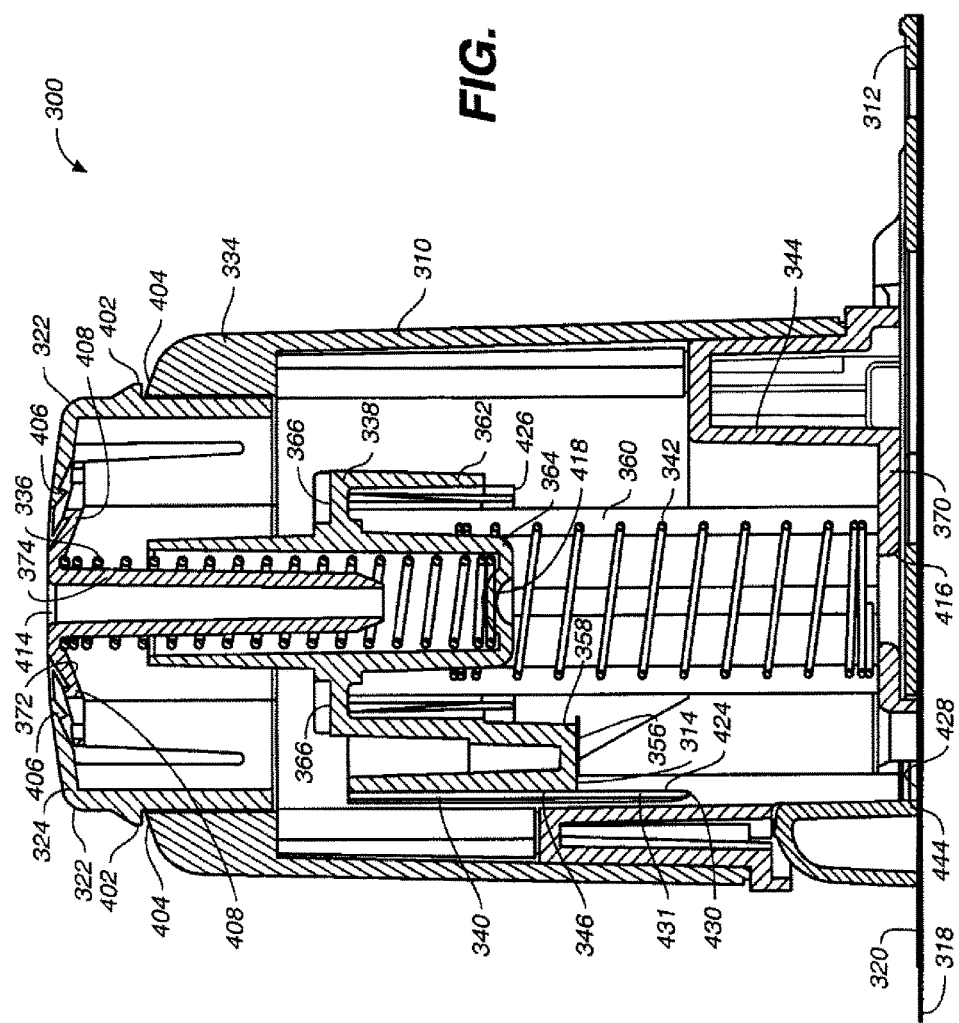

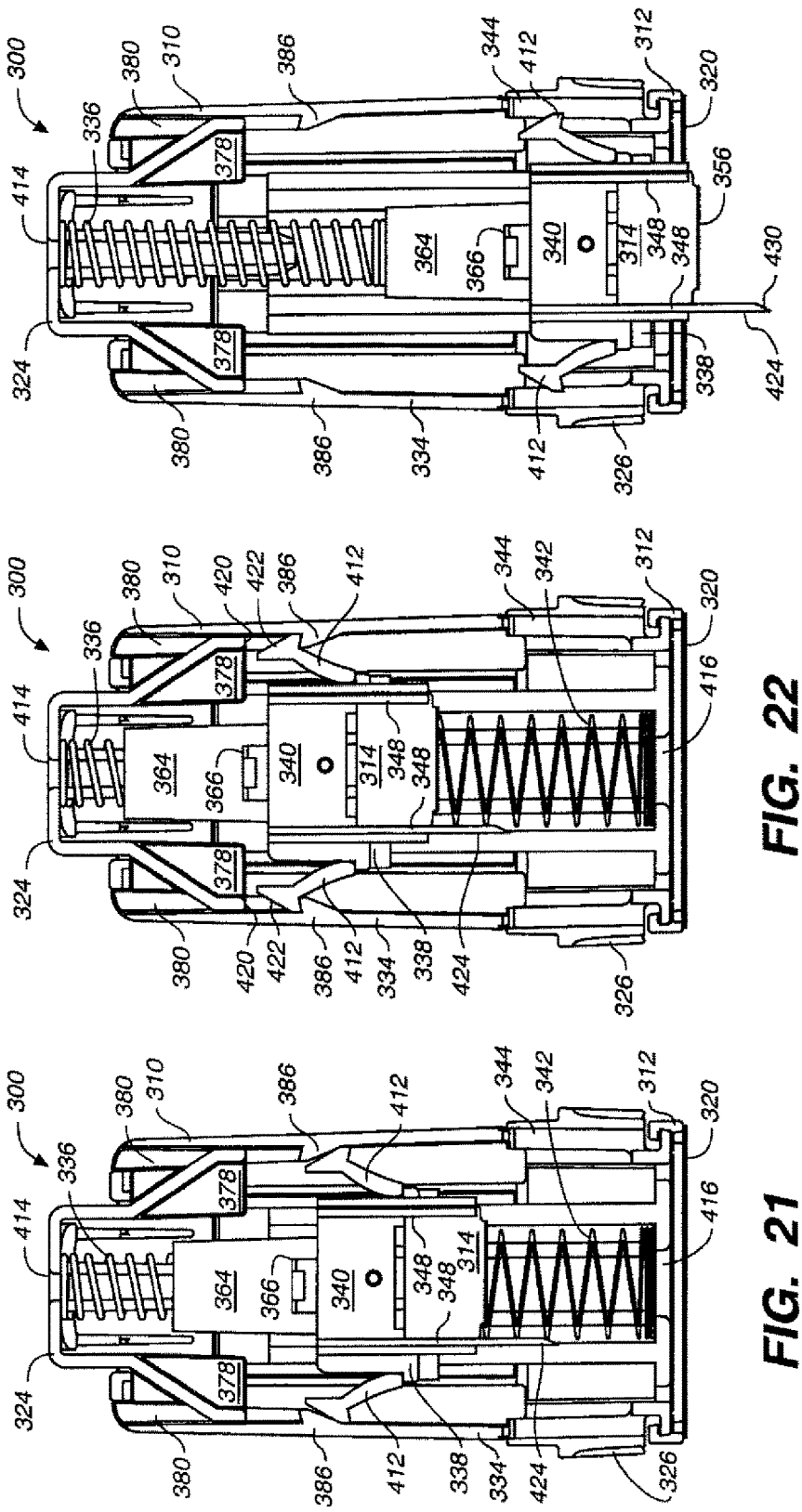

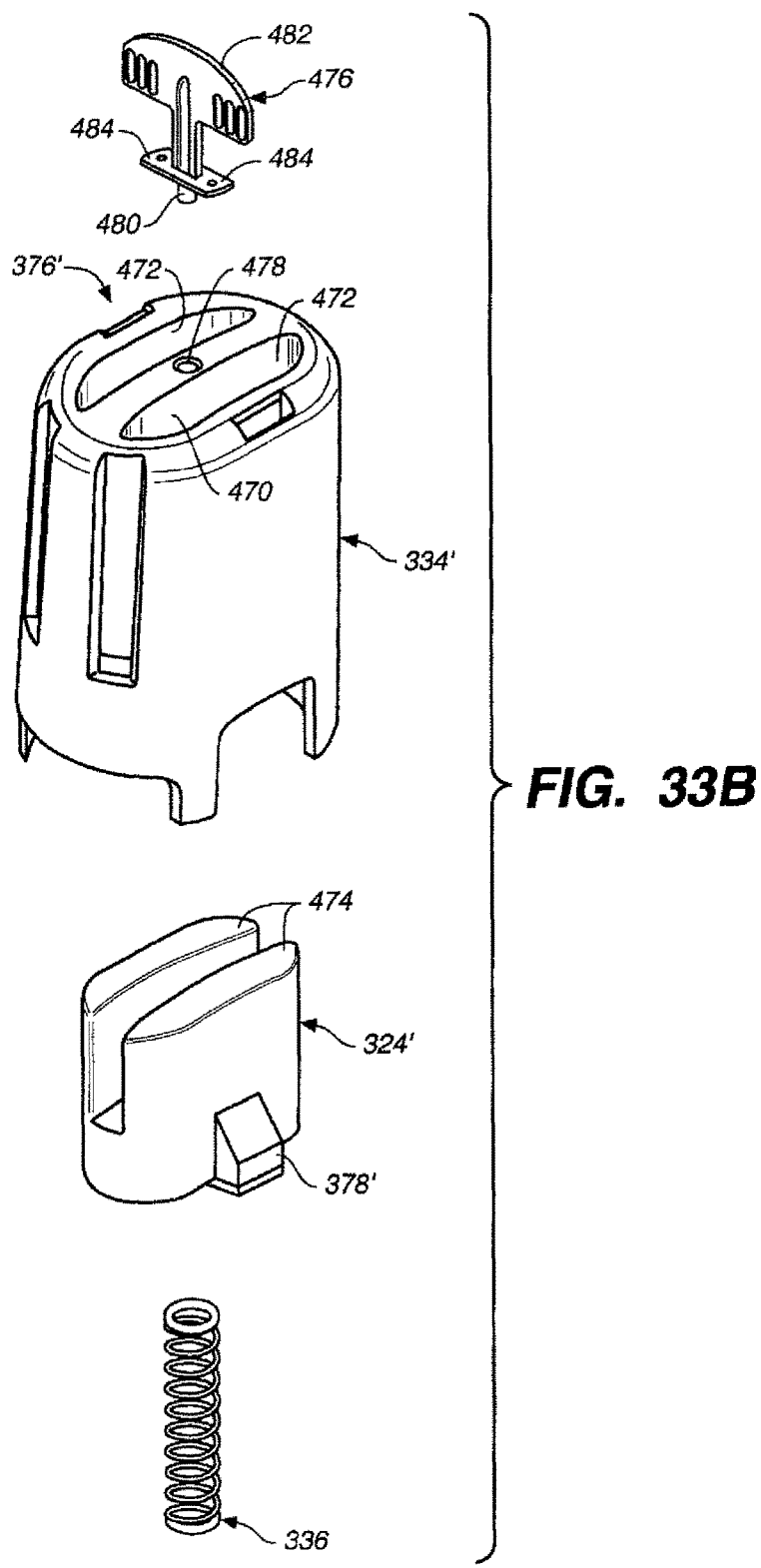

SENSOR INSERTER ASSEMBLY

RELATED APPLICATIONS

This application is a continuation of U.S. patent application Ser. No. 12/538,067 filed Aug. 7, 2009, which is a continuation application of U.S. patent application Ser. No. 11/899,917 filed Sep. 6, 2007, now U.S. Pat. No. 8,029,442, which is a continuation application of U.S. patent application Ser. No. 10/703,214 filed Nov. 5, 2003, now U.S. Pat. No. 7,381,184, which claims priority based on U.S. Provisional Application No. 60/424,099, entitled "Sensor Inserter Device and Methods of Use," filed on Nov. 5, 2002, the disclosures of each of which are incorporated herein in their entirety by this reference.

BACKGROUND

The monitoring of the level of glucose or other analytes, such as lactate or oxygen, in certain individuals is vitally important to their health. High or low levels of glucose or other analytes may have detrimental effects. The monitoring of glucose is particularly important to individuals with diabetes, as they must determine when insulin is needed to reduce glucose levels in their bodies or when additional glucose is needed to raise the level of glucose in their bodies.

A conventional technique used by many diabetics for personally monitoring their blood glucose level includes the periodic drawing of blood, the application of that blood to a test strip, and the determination of the blood glucose level using colorimetric, electrochemical, or photometric detection. This technique does not permit continuous or automatic monitoring of glucose levels in the body, but typically must be performed manually on a periodic basis. Unfortunately, the consistency with which the level of glucose is checked varies widely among individuals. Many diabetics find the periodic testing inconvenient and they sometimes forget to test their glucose level or do not have time for a proper test. In addition, some individuals wish to avoid the pain associated with the test. These situations may result in hyperglycemic or hypoglycemic episodes. An in vivo glucose sensor that continuously or automatically monitors the individual's glucose level would enable individuals to more easily monitor their glucose, or other analyte, levels.

A variety of devices have been developed for continuous or automatic monitoring of analytes, such as glucose, in the blood stream or interstitial fluid. A number of these devices use electrochemical sensors which are directly implanted into a blood vessel or in the subcutaneous tissue of a patient. However, these devices are often difficult to reproducibly and inexpensively manufacture in large numbers. In addition, these devices are typically large, bulky, and/or inflexible, and many cannot be used effectively outside of a controlled medical facility, such as a hospital or a doctor's office, unless the patient is restricted in his activities.

Some devices include a sensor guide which rests on or near the skin of the patient and may be attached to the patient to hold the sensor in place. These sensor guides are typically bulky and do not allow for freedom of movement. In addition, the sensor guides or the sensors include cables or wires for connecting the sensor to other equipment to direct the signals from the sensors to an analyzer. The size of the sensor guides and presence of cables and wires hinders the convenient use of these devices for everyday applications. The patient's comfort and the range of activities that can be performed while the sensor is implanted are important considerations in designing extended-use sensors for continuous or automatic in vivo monitoring of the level of an analyte, such as glucose. There is a need for a small, comfortable device which can continuously monitor the level of an analyte, such as glucose, while still permitting the patient to engage in normal activities. Continuous and/or automatic monitoring of the analyte can provide a warning to the patient when the level of the analyte is at or near a threshold level. For example, if glucose is the analyte, then the monitoring device might be configured to warn the patient of current or impending hyperglycemia or hypoglycemia. The patient can then take appropriate actions.

SUMMARY

The present invention is, in general, directed to devices and methods for the in vivo monitoring of an analyte, such as glucose or lactate, using a sensor to provide information to a patient about the level of the analyte. More particularly, the present invention relates to devices and methods for inserting a subcutaneously implantable electrochemical sensor in a patient for such monitoring.

Generally, the present invention relates to methods and devices for the continuous and/or automatic in vivo monitoring of the level of an analyte using a subcutaneously implantable sensor. Many of these devices are small and comfortable when used, thereby allowing a wide range of activities. One embodiment includes a sensor control unit having a housing adapted for placement on skin. The housing is also adapted to receive a portion of an electrochemical sensor. The sensor control unit includes two or more conductive contacts disposed on the housing and configured for coupling to two or more contact pads on the sensor. A transmitter is disposed in the housing and coupled to the plurality of conductive contacts for transmitting data obtained using the sensor. The sensor control unit may also include a variety of optional components, such as, for example, adhesive for adhering to the skin, a mounting unit, a receiver, a processing circuit, a power supply (e.g., a battery), an alarm system, a data storage unit, a watchdog circuit, and a measurement circuit. The sensor itself has at least one working electrode and at least one contact pad coupled to the working electrode or electrodes. The sensor may also include optional components, such as, for example, a counter electrode, a counter/reference electrode, a reference electrode, and a temperature probe. The analyte monitoring system also includes a display unit that has a receiver for receiving data from the sensor control unit and a display coupled to the receiver for displaying an indication of the level of an analyte. The display unit may optionally include a variety of components, such as, for example, a transmitter, an analyzer, a data storage unit, a watchdog circuit, an input device, a power supply, a clock, a lamp, a pager, a telephone interface, a computer interface, an alarm or alarm system, a radio, and a calibration unit. In addition, the analyte monitoring system or a component of the analyte monitoring system may optionally include a processor capable of determining a drug or treatment protocol and/or a drug delivery system.

According to one aspect of the invention, an insertion kit is disclosed for inserting an electrochemical sensor into a patient. The insertion kit includes an introducer. A portion of the introducer has a sharp, rigid, planar structure adapted to support the sensor during insertion of the electrochemical sensor. The insertion kit also includes an insertion gun having a port configured to accept the electrochemical sensor and the introducer. The insertion gun has a driving mechanism for driving the introducer and electrochemical sensor into the patient, and a retraction mechanism for removing the introducer while leaving the sensor within the patient.

According to another aspect of the invention, a method of using an electrochemical sensor is disclosed. A mounting unit is adhered to the skin of a patient. An insertion gun is aligned with a port on the mounting unit. The electrochemical sensor is disposed within the insertion gun and then the electrochemical sensor is inserted into the skin of the patient using the insertion gun. The insertion gun is removed and a housing of the sensor control unit is mounted on the mounting base. A plurality of conductive contacts disposed on the housing is coupled to a plurality of contact pads disposed on the electrochemical sensor to prepare the sensor for use.

The above summary of the present invention is not intended to describe each disclosed embodiment or every implementation of the present invention. The Figures and the detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 10A is a top view of one embodiment of an on-skin sensor control unit, according to the invention.

FIG. 10B is a top view of one embodiment of a mounting unit of the on-skin sensor control unit of FIG. 10A.

FIG. 11A is a top view of another embodiment of an on-skin sensor control unit after insertion of an introducer and a sensor, according to the invention.

FIG. 11B is a top view of one embodiment of a mounting unit of the on-skin sensor control unit of FIG. 11A.

FIG. 11E is a top view of the on-skin sensor control unit of FIG. 11A with a cover of the housing removed.

FIG. 14 is a perspective view of the adhesive mount and sensor attached to the patient's skin.

FIG. 15 is a perspective view of the transmitter attached to the adhesive mount.

FIG. 17 is a side elevation view of the preferred commercial embodiment of FIG. 13.

FIG. 18 is an end elevation view of the preferred commercial embodiment of FIG. 13.

FIG. 19 is a cross-sectional view taken along line 19-19 in FIG. 18.

FIG. 21 is a broken away view similar to FIG. 20, showing the shuttle in the neutral position.

FIG. 22 is a broken away view similar to FIG. 20, showing the shuttle in the cocked position.

FIG. 23 is a broken away view similar to FIG. 20, showing the shuttle in the insertion position.

FIG. 33B is an exploded view of some of the components shown assembled in FIG. 33A.

Figure 1:
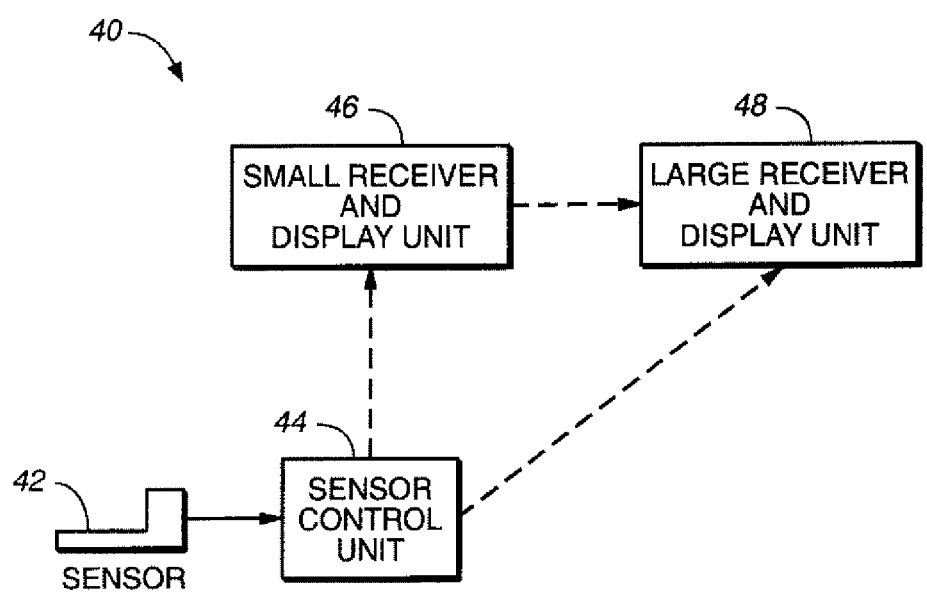
FIG. 1 is a block diagram of one embodiment of a subcutaneous analyte monitor using a subcutaneously implantable analyte sensor, according to the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is applicable to an analyte monitoring system using an implantable sensor for the in vivo determination of a concentration of an analyte, such as glucose or lactate, in a fluid. The sensor can be, for example, subcutaneously implanted in a patient for the continuous or periodic monitoring of an analyte in a patient's interstitial fluid. This can then be used to infer the glucose level in the patient's bloodstream. Other in vivo analyte sensors can be made, according to the invention, for insertion into a vein, artery, or other portion of the body containing fluid. The analyte monitoring system is typically configured for monitoring the level of the analyte over a time period which may range from days to weeks or longer.

The analyte monitoring systems of the present invention can be utilized under a variety of conditions. The particular configuration of a sensor and other units used in the analyte monitoring system may depend on the use for which the analyte monitoring system is intended and the conditions under which the analyte monitoring system will operate. One embodiment of the analyte monitoring system includes a sensor configured for implantation into a patient or user. For example, implantation of the sensor may be made in the arterial or venous systems for direct testing of analyte levels in blood. Alternatively, a sensor may be implanted in the interstitial tissue for determining the analyte level in interstitial fluid. This level may be correlated and/or converted to analyte levels in blood or other fluids. The site and depth of implantation may affect the particular shape, components, and configuration of the sensor. Subcutaneous implantation may be preferred, in some cases, to limit the depth of implantation of the sensor. Sensors may also be implanted in other regions of the body to determine analyte levels in other fluids. Examples of suitable sensor for use in the analyte monitoring systems of the invention are described in U.S. patent application Ser. No. 09/034,372 and Ser. No. 09/753, 746 (the complete parent application to this CIP), both incorporated herein by reference.

One embodiment of the analyte monitoring system 40 for use with an implantable sensor 42, and particularly for use with a subcutaneously implantable sensor, is illustrated in block diagram form in FIG. 1. The analyte monitoring system 40 includes, at minimum, a sensor 42, a portion of which is configured for implantation (e.g., subcutaneous, venous, or arterial implantation) into a patient, and a sensor control unit 44. The sensor 42 is coupled to the sensor control unit 44 which is typically attached to the skin of a patient. The sensor control unit 44 operates the sensor 42, including, for example, providing a voltage across the electrodes of the sensor 42 and collecting signals from the sensor 42. The sensor control unit 44 may evaluate the signals from the sensor 42 and/or transmit the signals to one or more optional receiver/display units 46, 48 for evaluation. The sensor control unit 44 and/or the receiver/display units 46, 48 may display or otherwise communicate the current level of the analyte. Furthermore, the sensor control unit 44 and/or the receiver/display units 46, 48 may indicate to the patient, via, for example, an audible, visual, or other sensory-stimulating alarm, when the level of the analyte is at or near a threshold level. In some embodiments, an electrical shock can be delivered to the patient as a warning through one of the electrodes or the optional temperature probe of the sensor. For example, if glucose is monitored then an alarm may be used to alert the patient to a hypoglycemic or hyperglycemic glucose level and/or to impending hypoglycemia or hyperglycemia.

Figure 2:
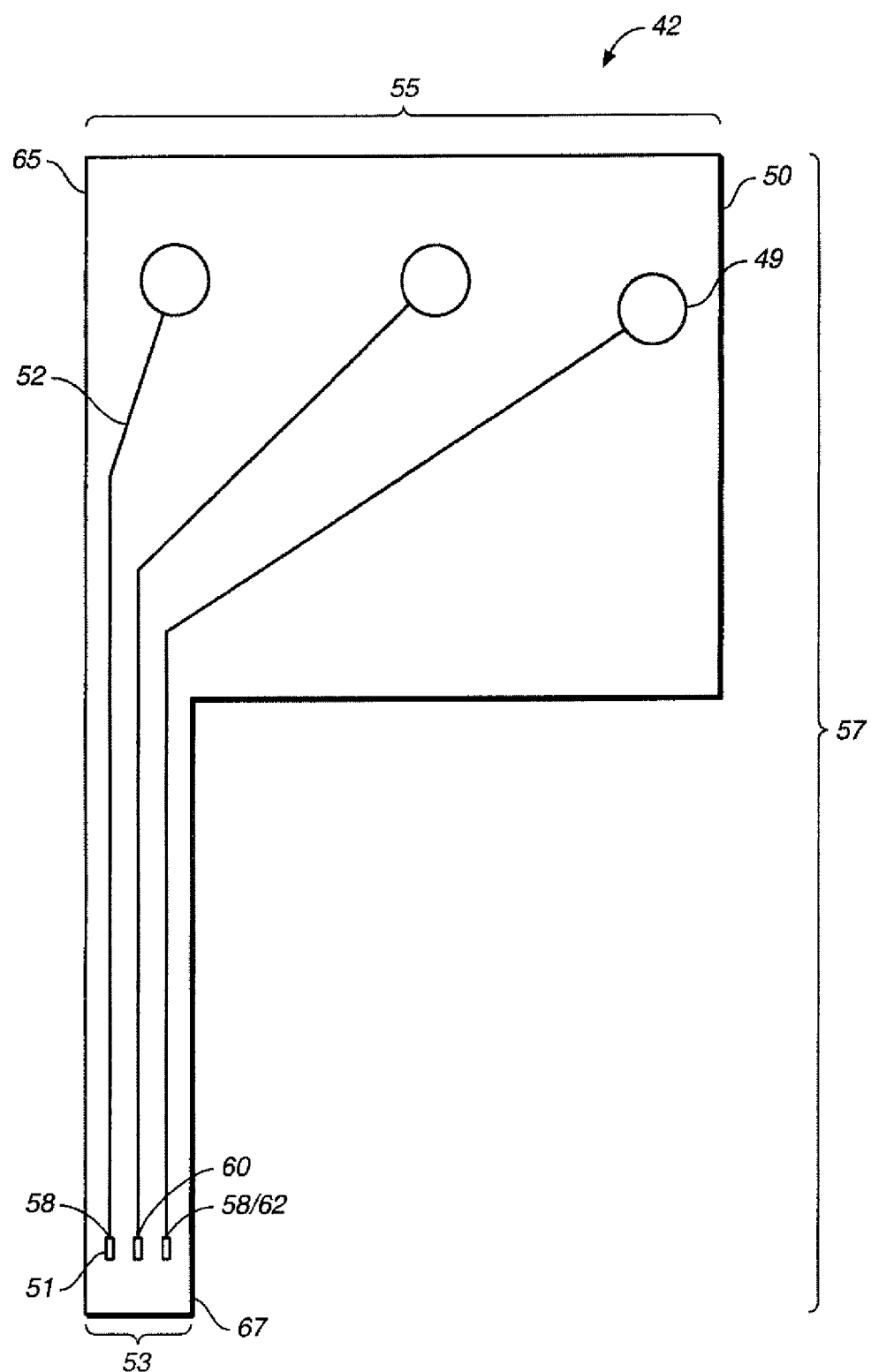
FIG. 2 is a top view of one embodiment of an analyte sensor, according to the invention.

A sensor 42 includes at least one working electrode 58 formed on a substrate 50, as shown in FIG. 2. The sensor 42 may also include at least one counter electrode 60 (or counter/reference electrode) and/or at least one reference electrode 62. The substrate 50 of the sensor may be formed using a variety of non-conducting materials, including, for example, polymeric or plastic materials and ceramic materials. Suitable materials for a particular sensor 42 may be determined, at least in part, based on the desired use of the sensor 42 and properties of the materials.

In some embodiments, the substrate is flexible. For example, if the sensor 42 is configured for implantation into a patient, then the sensor 42 may be made flexible (although rigid sensors may also be used for implantable sensors) to reduce pain to the patient and damage to the tissue caused by the implantation of and/or the wearing of the sensor 42. A flexible substrate 50 often increases the patient's comfort and allows a wider range of activities. Suitable materials for a flexible substrate 50 include, for example, non-conducting plastic or polymeric materials and other non-conducting, flexible, deformable materials. Examples of useful plastic or polymeric materials include thermoplastics such as polycarbonates, polyesters (e.g., Mylar™ and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensor 42 is made using a relatively rigid substrate 50 to, for example, provide structural support against bending or breaking Examples of rigid materials that may be used as the substrate 50 include poorly conducting ceramics, such as aluminum oxide and silicon dioxide. One advantage of an implantable sensor 42 having a rigid substrate is that the sensor 42 may have a sharp point and/or a sharp edge to aid in implantation of a sensor 42 without an additional introducer.

It will be appreciated that for many sensors 42 and sensor applications, both rigid and flexible sensors will operate adequately. The flexibility of the sensor 42 may also be controlled and varied along a continuum by changing, for example, the composition and/or thickness of the substrate 50.

In addition to considerations regarding flexibility, it is often desirable that implantable sensors 42 should have a substrate 50 which is non-toxic. Preferably, the substrate 50 is approved by one or more appropriate governmental agencies or private groups for in vivo use.

Although the substrate 50 in at least some embodiments has uniform dimensions along the entire length 57 of the sensor 42, in other embodiments, the substrate 50 has a distal end 67 and a proximal end 65 with different widths 53, 55, respectively, as illustrated in FIG. 2. In these embodiments, the distal end 67 of the substrate 50 may have a relatively narrow width 53. For sensors 42 which are implantable into the subcutaneous tissue or another portion of a patient's body, the narrow width 53 of the distal end 67 of the substrate 50 may facilitate the implantation of the sensor 42. Often, the narrower the width of the sensor 42, the less pain the patient will feel during implantation of the sensor and afterwards. The sensor 42 is designed to be a replaceable component in an implantable analyte monitor. Typically, the sensor 42 is capable of operation over a period of days. Preferably, the period of operation is at least three days. The sensor 42 can then be removed and replaced with a new sensor.

Figure 3:
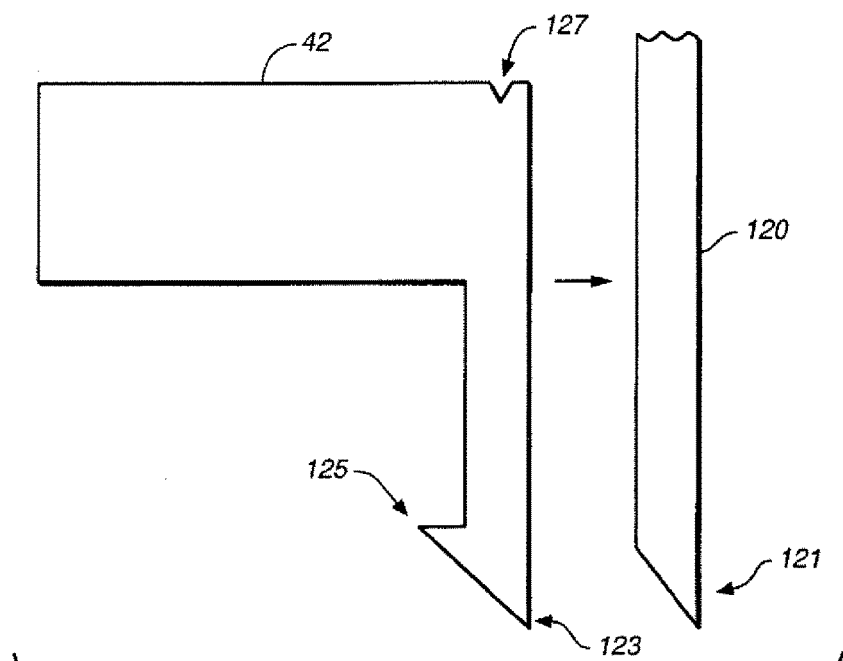
FIG. 3 is an expanded side view of one embodiment of a sensor and an introducer, according to the invention.

An introducer 120 can be used to subcutaneously insert the sensor 42 into the patient, as illustrated in FIG. 3. The introducer 120 is typically formed using structurally rigid materials, such as metal or rigid plastic. Preferred materials include stainless steel and ABS (acrylonitrile-butadiene-styrene) plastic. In some embodiments, the introducer 120 is pointed and/or sharp at the tip 121 to facilitate penetration of the skin of the patient. A sharp, thin introducer may reduce pain felt by the patient upon insertion of the sensor 42. In other embodiments, the tip 121 of the introducer 120 has other shapes, including a blunt or flat shape. These embodiments may be particularly useful when the introducer 120 does not penetrate the skin but rather serves as a structural support for the sensor 42 as the sensor 42 is pushed into the skin.

Figure 4A:
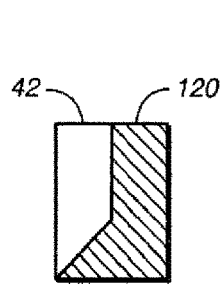
FIGS. 4A, 4B, 4C are cross-sectional views of three embodiments of the introducer of FIG. 3.
Figure 4B:
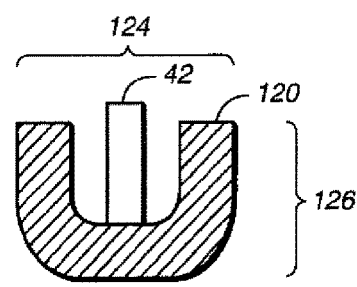
Figure 4C:
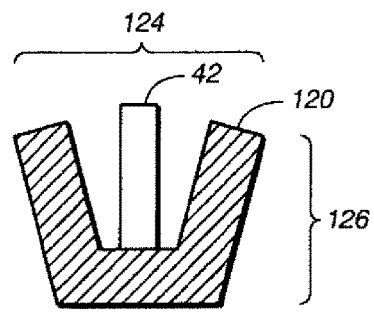

The introducer 120 may have a variety of cross-sectional shapes, as shown in FIGS. 4A, 4B, and 4C. The introducer 120 illustrated in FIG. 4A is a flat, planar, pointed strip of rigid material which may be attached or otherwise coupled to the sensor 42 to ease insertion of the sensor 42 into the skin of the patient, as well as to provide structural support to the sensor 42 during insertion. The introducers 120 of FIGS. 4B and 4C are U- or V-shaped implements that support the sensor 42 to limit the amount that the sensor 42 may bend or bow during insertion. The cross-sectional width 124 of the introducers 120 illustrated in FIGS. 4B and 4C is typically 1 mm or less, preferably 700 µm or less, more preferably 500 µm or less, and most preferably 300 µm or less. The cross-sectional height 126 of the introducer 120 illustrated in FIGS. 4B and 4C is typically about 1 mm or less, preferably about 700 µm or less, and more preferably about 500 µm or less.

The sensor 42 itself may include optional features to facilitate insertion. For example, the sensor 42 may be pointed at the tip 123 to ease insertion, as illustrated in FIG. 3. In addition, the sensor 42 may include a barb 125 which helps retain the sensor 42 in the subcutaneous tissue of the patient. The barb 125 may also assist in anchoring the sensor 42 within the subcutaneous tissue of the patient during operation of the sensor 42. However, the barb 125 is typically small enough that little damage is caused to the subcutaneous tissue when the sensor 42 is removed for replacement. The sensor 42 may also include a notch 127 that can be used in cooperation with a corresponding structure (not shown) in the introducer to apply pressure against the sensor 42 during insertion, but disengage as the introducer 120 is removed. One example of such a structure in the insertion device is a rod (not shown) between two opposing sides of an introducer 120 and at an appropriate height of the introducer 120.

In operation, the sensor 42 is placed within or next to the introducer 120 and then a force is provided against the introducer 120 and/or sensor 42 to carry the sensor 42 into the skin of the patient. In one embodiment, the force is applied to the sensor 42 to push the sensor into the skin, while the introducer 120 remains stationary and provides structural support to the sensor 42. Alternatively, the force is applied to the introducer 120 and optionally to the sensor 42 to push a portion of both the sensor 42 and the introducer 120 through the skin of the patient and into the subcutaneous tissue. The introducer 120 is optionally pulled out of the skin and subcutaneous tissue with the sensor 42 remaining in the subcutaneous tissue due to frictional forces between the sensor 42 and the patient's tissue. If the sensor 42 includes the optional barb 125, then this structure may also facilitate the retention of the sensor 42 within the interstitial tissue as the barb catches in the tissue.

Figure 9:
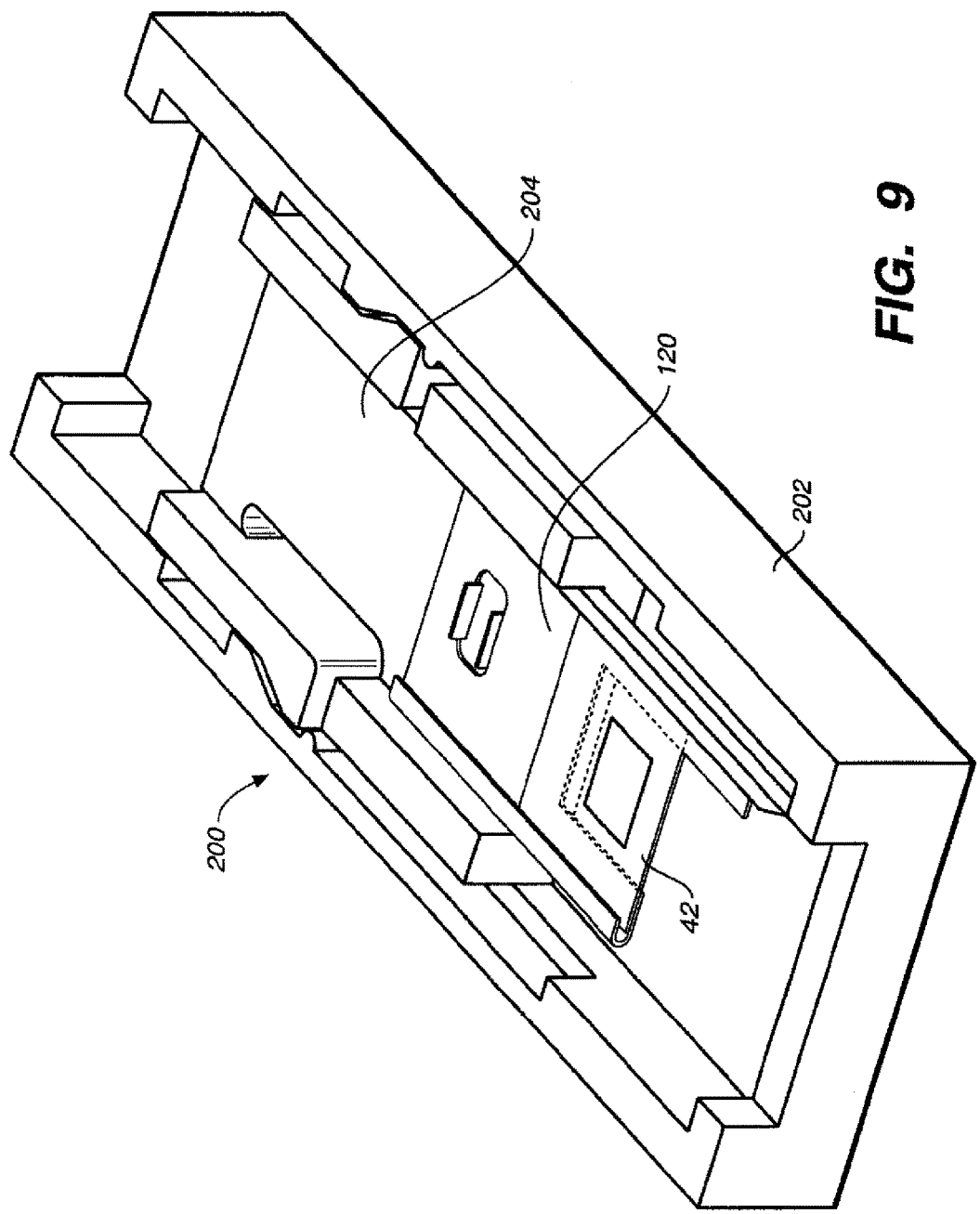
FIG. 9 is a perspective view of the internal structure of an insertion gun, according to the invention.

The force applied to the introducer 120 and/or the sensor 42 may be applied manually or mechanically. Preferably, the sensor 42 is reproducibly inserted through the skin of the patient. In one embodiment, an insertion gun is used to insert the sensor. One example of an insertion gun 200 for inserting a sensor 42 is shown in FIG. 9. The insertion gun 200 includes a housing 202 and a carrier 204. The introducer 120 is typically mounted on the carrier 204 and the sensor 42 is pre-loaded into the introducer 120. The carrier 204 drives the sensor 42 and, optionally, the introducer 120 into the skin of the patient using, for example, a cocked or wound spring, a burst of compressed gas, an electromagnet repelled by a second magnet, or the like, within the insertion gun 200. In some instances, for example, when using a spring, the carrier 204 and introducer 120 may be moved, cocked, or otherwise prepared to be directed towards the skin of the patient.

After the sensor 42 is inserted, the insertion gun 200 may contain a mechanism which pulls the introducer 120 out of the skin of the patient. Such a mechanism may use a spring, electromagnet, or the like to remove the introducer 120.

The insertion gun may be reusable. The introducer 120 is often disposable to avoid the possibility of contamination. Alternatively, the introducer 120 may be sterilized and reused. In addition, the introducer 120 and/or the sensor 42 may be coated with an anticlotting agent to prevent fouling of the sensor 42.

In one embodiment, the sensor 42 is injected between 2 to 12 mm into the interstitial tissue of the patient for subcutaneous implantation. Preferably, the sensor is injected 3 to 9 mm, and more preferably 5 to 7 mm, into the interstitial tissue. Other embodiments of the invention, may include sensors implanted in other portions of the patient, including, for example, in an artery, vein, or organ. The depth of implantation varies depending on the desired implantation target.

Although the sensor 42 may be inserted anywhere in the body, it is often desirable that the insertion site be positioned so that the on-skin sensor control unit 44 can be concealed. In addition, it is often desirable that the insertion site be at a place on the body with a low density of nerve endings to reduce the pain to the patient. Examples of preferred sites for insertion of the sensor 42 and positioning of the on-skin sensor control unit 44 include the abdomen, thigh, leg, upper arm, and shoulder.

An insertion angle is measured from the plane of the skin (i.e., inserting the sensor perpendicular to the skin would be a 90° insertion angle). Insertion angles usually range from 10 to 90°, typically from 15 to 60°, and often from 30 to 45°.

On-Skin Sensor Control Unit

Figure 5:
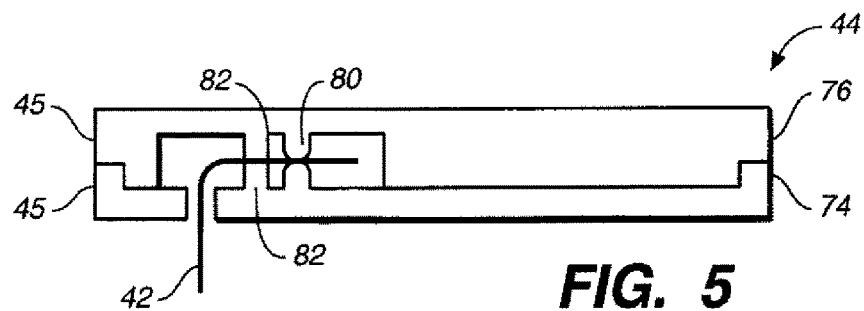
FIG. 5 is a cross-sectional view of one embodiment of an on-skin sensor control unit, according to the invention.
Figure 6:
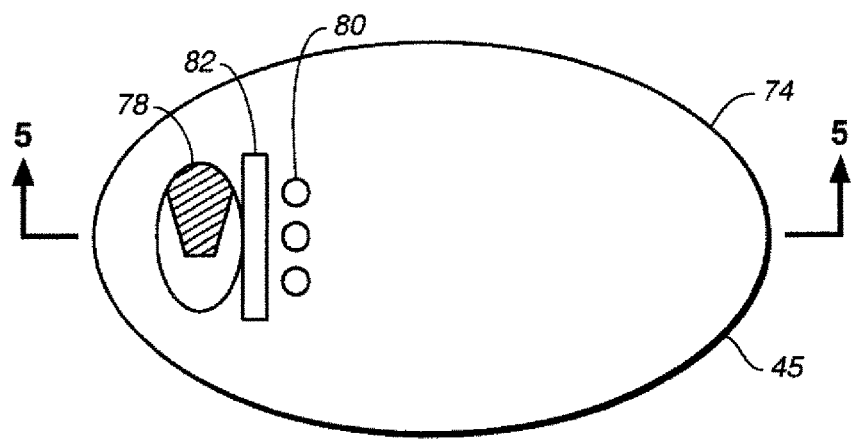
FIG. 6 is a top view of a base of the on-skin sensor control unit of FIG. 5.
Figure 7:
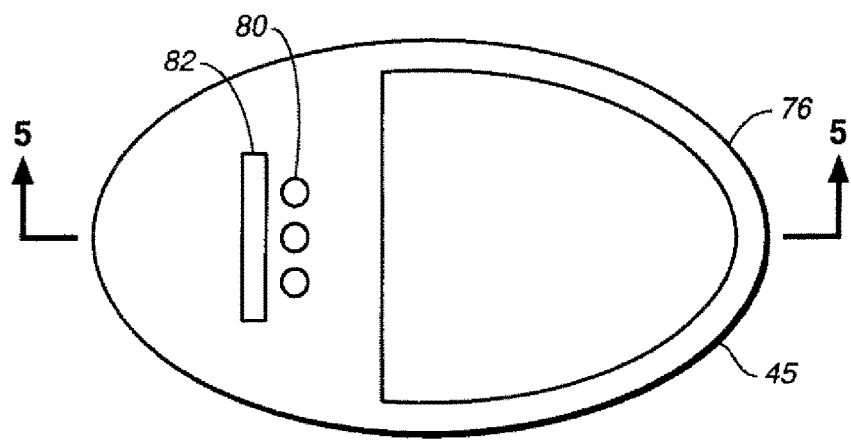
FIG. 7 is a bottom view of a cover of the on-skin sensor control unit of FIG. 5.

The on-skin sensor control unit 44 is configured to be placed on the skin of a patient. The on-skin sensor control unit 44 is optionally formed in a shape that is comfortable to the patient and which may permit concealment, for example, under a patient's clothing. The thigh, leg, upper arm, shoulder, or abdomen are convenient parts of the patient's body for placement of the on-skin sensor control unit 44 to maintain concealment. However, the on-skin sensor control unit 44 may be positioned on other portions of the patient's body. One embodiment of the on-skin sensor control unit 44 has a thin, oval shape to enhance concealment, as illustrated in FIGS. 5-7. However, other shapes and sizes may be used.

The particular profile, as well as the height, width, length, weight, and volume of the on-skin sensor control unit 44 may vary and depends, at least in part, on the components and associated functions included in the on-skin sensor control unit 44, as discussed below. For example, in some embodiments, the on-skin sensor control unit 44 has a height of 1.3 cm or less, and preferably 0.7 cm or less. In some embodiments, the on-skin sensor control unit 44 has a weight of 90 grams or less, preferably 45 grams or less, and more preferably 25 grams or less. In some embodiments, the on-skin sensor control unit 44 has a volume of about 15 cm$^3$ or less, preferably about 10 cm$^3$ or less, more preferably about 5 cm$^3$ or less, and most preferably about 2.5 cm$^3$ or less.

The on-skin sensor control unit 44 includes a housing 45, as illustrated in FIGS. 5-7. The housing 45 is typically formed as a single integral unit that rests on the skin of the patient. The housing 45 typically contains most or all of the electronic components, described below, of the on-skin sensor control unit 44. The on-skin sensor control unit 44 usually includes no additional cables or wires to other electronic components or other devices. If the housing includes two or more parts, then those parts typically fit together to form a single integral unit.

In some embodiments, conductive contacts 80 are provided on the exterior of the housing 45. In other embodiments, the conductive contacts 80 are provided on the interior of the housing 45, for example, within a hollow or recessed region.

In some embodiments, the housing 45 of the on-skin sensor control unit 44 is a single piece. The conductive contacts 80 may be formed on the exterior of the housing 45 or on the interior of the housing 45 provided there is a port 78 in the housing 45 through which the sensor 42 can be directed to access the conductive contacts 80.

In other embodiments, the housing 45 of the on-skin sensor control unit 44 is formed in at least two separate portions that fit together to form the housing 45, for example, a base 74 and a cover 76, as illustrated in FIGS. 5-7. The two or more portions of the housing 45 may be entirely separate from each other. Alternatively, at least some of the two or more portions of the housing 45 may be connected together, for example, by a hinge, to facilitate the coupling of the portions to form the housing 45 of the on-skin sensor control unit 44.

These two or more separate portions of the housing 45 of the on-skin sensor control unit 44 may have complementary, interlocking structures, such as, for example, interlocking ridges or a ridge on one component and a complementary groove on another component, so that the two or more separate components may be easily and/or firmly coupled together. This may be useful, particularly if the components are taken apart and fit together occasionally, for example, when a battery or sensor 42 is replaced. However, other fasteners may also be used to couple the two or more components together, including, for example, screws, nuts and bolts, nails, staples, rivets, or the like. In addition, adhesives, both permanent or temporary, may be used including, for example, contact adhesives, pressure sensitive adhesives, glues, epoxies, adhesive resins, and the like.

Typically, the housing 45 is at least water resistant to prevent the flow of fluids into contact with the components in the housing, including, for example, the conductive contacts 80. Preferably, the housing is waterproof. In one embodiment, two or more components of the housing 45, for example, the base 74 and the cover 76, fit together tightly to form a hermetic, waterproof, or water resistant seal so that fluids cannot flow into the interior of the on-skin sensor control unit 44. This may be useful to avoid corrosion currents and/or degradation of items within the on-skin sensor control unit 44, such as the conductive contacts, the battery, or the electronic components, particularly when the patient engages in such activities as showering, bathing, or swimming.

Water resistant, as used herein, means that there is no penetration of water through a water resistant seal or housing when immersed in water at a depth of one meter at sea level. Waterproof, as used herein, means that there is no penetration of water through the waterproof seal or housing when immersed in water at a depth of ten meters, and preferably fifty meters, at sea level. It is often desirable that the electronic circuitry, power supply (e.g., battery), and conductive contacts of the on-skin sensor control unit, as well as the contact pads of the sensor, are contained in a water resistant, and preferably a waterproof, environment.

Figure 8:
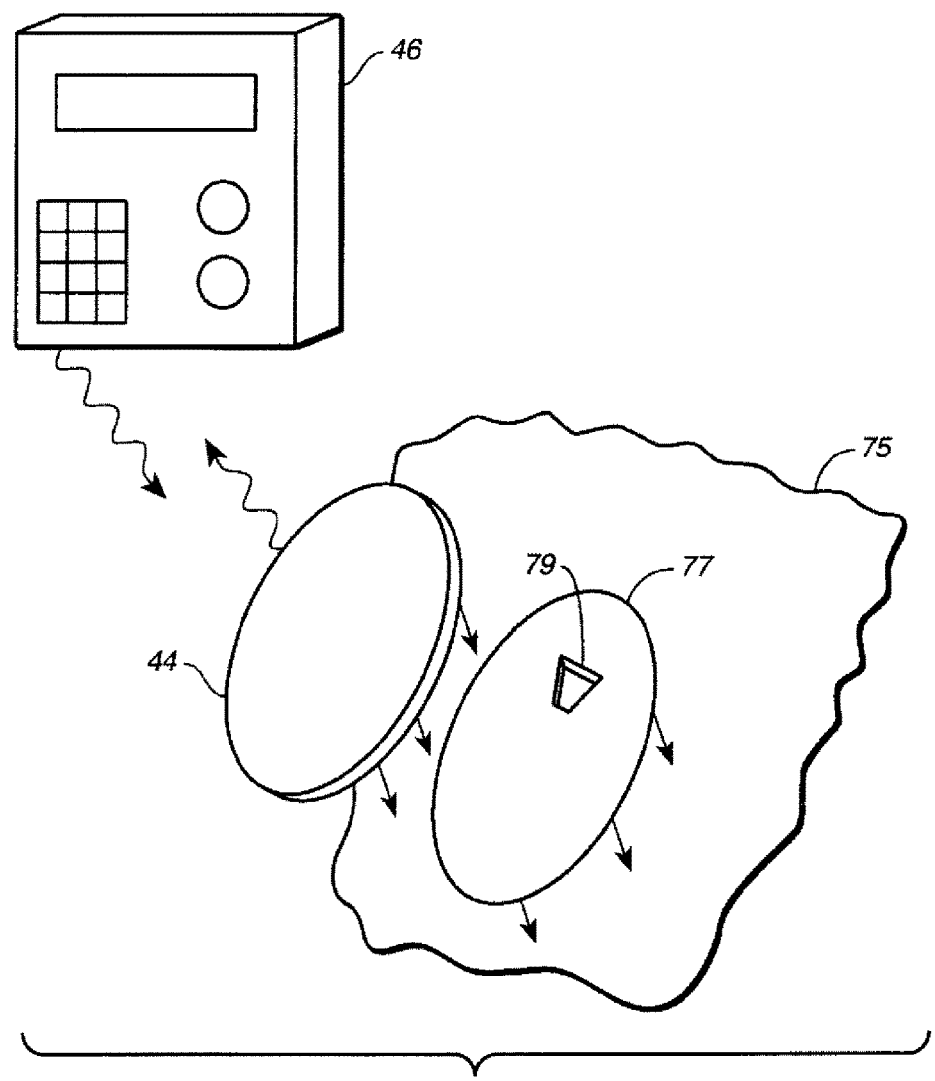
FIG. 8 is a perspective view of the on-skin sensor control unit of FIG. 5 on the skin of a patient.

The on-skin sensor control unit 44 is typically attached to the skin 75 of the patient, as illustrated in FIG. 8. The on-skin sensor control unit 44 may be attached by a variety of techniques including, for example, by adhering the on-skin sensor control unit 44 directly to the skin 75 of the patient with an adhesive provided on at least a portion of the housing 45 of the on-skin sensor control unit 44 which contacts the skin 75, by suturing the on-skin sensor control unit 44 to the skin 75 through suture openings (not shown) in the sensor control unit 44, or by strapping the on-skin sensor control unit 44 to the skin 75.

Another method of attaching the housing 45 of the on-skin sensor control unit 44 to the skin 75 includes using a mounting unit, 77. The mounting unit 77 is often a part of the on-skin sensor control unit 44. One example of a suitable mounting unit 77 is a double-sided adhesive strip, one side of which is adhered to a surface of the skin of the patient and the other side is adhered to the on-skin sensor control unit 44. In this embodiment, the mounting unit 77 may have an optional opening 79 which is large enough to allow insertion of the sensor 42 through the opening 79. Alternatively, the sensor may be inserted through a thin adhesive and into the skin.

A variety of adhesives may be used to adhere the on-skin sensor control unit 44 to the skin 75 of the patient, either directly or using the mounting unit 77, including, for example, pressure sensitive adhesives (PSA) or contact adhesives. Preferably, an adhesive is chosen which is not irritating to all or a majority of patients for at least the period of time that a particular sensor 42 is implanted in the patient. Alternatively, a second adhesive or other skin-protecting compound may be included with the mounting unit so that a patient, whose skin is irritated by the adhesive on the mounting unit 77, can cover his skin with the second adhesive or other skin-protecting compound and then place the mounting unit 77 over the second adhesive or other skin-protecting compound. This should substantially prevent the irritation of the skin of the patient because the adhesive on the mounting unit 77 is no longer in contact with the skin, but is instead in contact with the second adhesive or other skin-protecting compound.

Returning to FIG. 8, when the sensor 42 is changed, the on-skin sensor control unit 44 may be moved to a different position on the skin 75 of the patient, for example, to avoid excessive irritation. Alternatively, the on-skin sensor control unit 44 may remain at the same place on the skin of the patient until it is determined that the unit 44 should be moved.

Another embodiment of a mounting unit 77 used in an on-skin sensor control unit 44 is illustrated in FIGS. 10A and 10B. The mounting unit 77 and a housing 45 of an on-skin sensor control unit 44 are mounted together in, for example, an interlocking manner, as shown in FIG. 10A. The mounting unit 77 is formed, for example, using plastic or polymer materials, including, for example, polyvinyl chloride, polyethylene, polypropylene, polystyrene, ABS polymers, and copolymers thereof. The mounting unit 77 may be formed using a variety of techniques including, for example, injection molding, compression molding, casting, and other molding methods.

The mounting unit 77 typically includes an adhesive on a bottom surface of the mounting unit 77 to adhere to the skin of the patient or the mounting unit 77 is used in conjunction with, for example, double-sided adhesive tape or the like. The mounting unit 77 typically includes an opening 79 through which the sensor 42 is inserted, as shown in FIG. 10B. The mounting unit 77 may also include a support structure 220 for holding the sensor 42 in place and against the conductive contacts 80 on the on-skin sensor control unit 42. The mounting unit 77, also, optionally, includes a positioning structure 222, such as an extension of material from the mounting unit 77, that corresponds to a structure (not shown), such as an opening, on the sensor 42 to facilitate proper positioning of the sensor 42, for example, by aligning the two complementary structures.

Figure 11C:
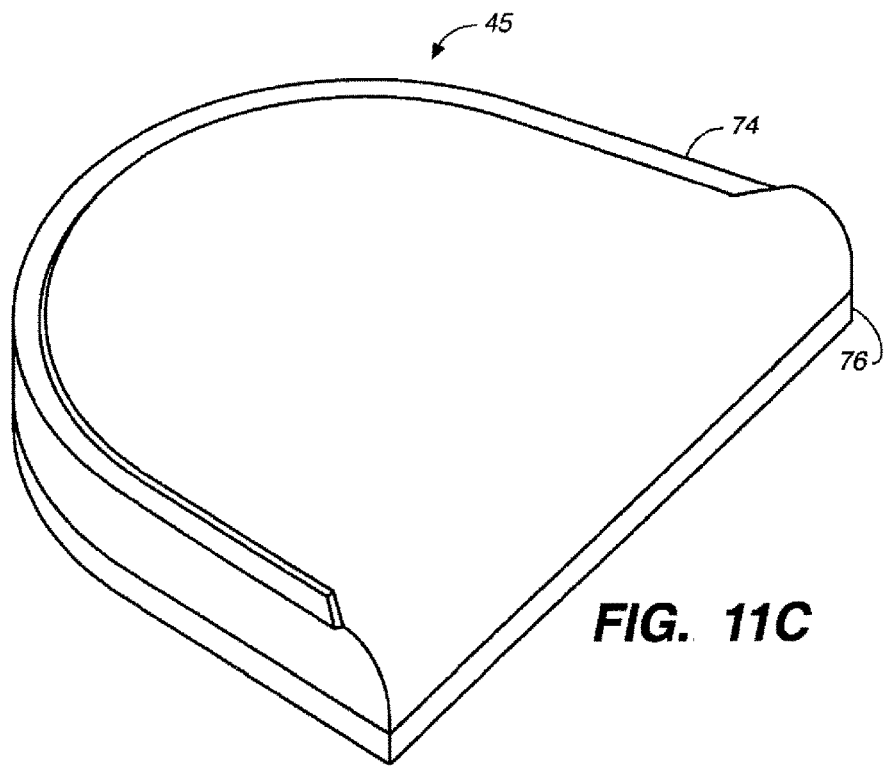
FIG. 11C is a top view of one embodiment of a housing for at least a portion of the electronics of the on-skin sensor control unit of FIG. 11A.
Figure 11D:
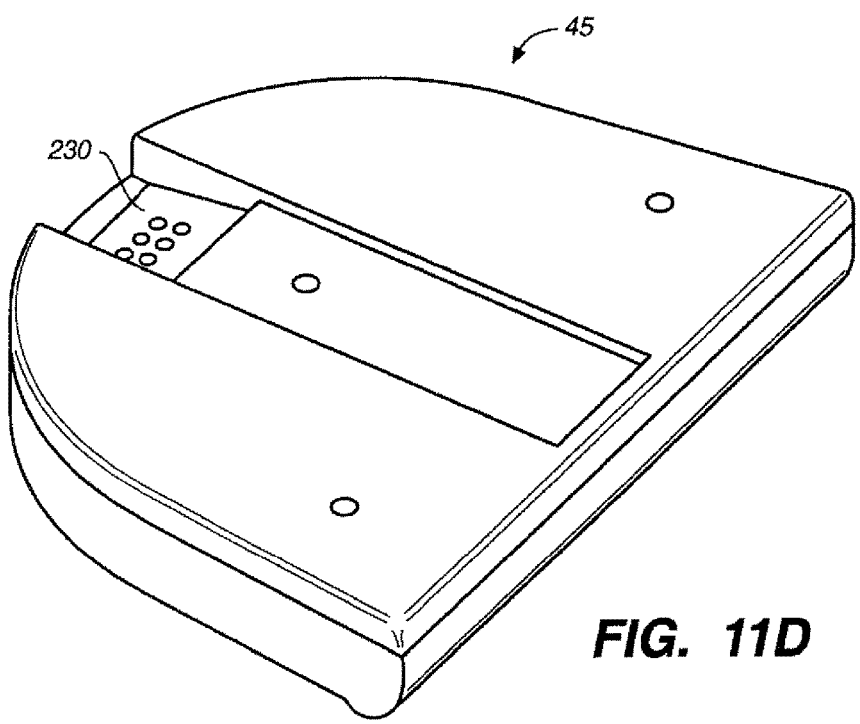
FIG. 11D is a bottom view of the housing of FIG. 11C.

In another embodiment, a coupled mounting unit 77 and housing 45 of an on-skin sensor control unit 44 is provided on an adhesive patch 204 with an optional cover 206 to protect and/or confine the housing 45 of the on-skin sensor control unit 44, as illustrated in FIG. 11A. The optional cover may contain an adhesive or other mechanism for attachment to the housing 45 and/or mounting unit 77. The mounting unit 77 typically includes an opening 49 through which a sensor 42 is disposed, as shown in FIG. 11B. The opening 49 may optionally be configured to allow insertion of the sensor 42 through the opening 49 using an introducer 120 or insertion gun 200 (see FIG. 9). The housing 45 of the on-skin sensor control unit 44 has a base 74 and a cover 76, as illustrated in FIG. 11C. A bottom view of the housing 45, as shown in FIG. 11D, illustrates ports 230 through which conductive contacts (not shown) extend to connect with contact pads on the sensor 42. A board 232 for attachment of circuit components may optionally be provided within the on-skin sensor control unit 44, as illustrated in FIG. 11E.

In some embodiments, the adhesive on the on-skin sensor control unit 44 and/or on any of the embodiments of the mounting unit 77 is water resistant or waterproof to permit activities such as showering and/or bathing while maintaining adherence of the on-skin sensor control unit 44 to the skin 75 of the patient and, at least in some embodiments, preventing water from penetrating into the sensor control unit 44. The use of a water resistant or waterproof adhesive combined with a water resistant or waterproof housing 45 protects the components in the sensor control unit 44 and the contact between the conductive contacts 80 and the sensor 42 from damage or corrosion. An example of a non-irritating adhesive that repels water is Tegaderm™ (3M™, St. Paul, Minn.).

In one embodiment, the on-skin sensor control unit 44 includes a sensor port 78 through which the sensor 42 enters the subcutaneous tissue of the patient, as shown in FIGS. 5 to 7. The sensor 42 may be inserted into the subcutaneous tissue of the patient through the sensor port 78. The on-skin sensor control unit 44 may then be placed on the skin of the patient with the sensor 42 being threaded through the sensor port 78. If the housing 45 of the sensor 42 has, for example, a base 74 and a cover 76, then the cover 76 may be removed to allow the patient to guide the sensor 42 into the proper position for contact with the conductive contacts 80.

Alternatively, if the conductive contacts 80 are within the housing 45 the patient may slide the sensor 42 into the housing 45 until contact is made between the contact pads 49 and the conductive contacts 80. The sensor control unit 44 may have a structure which obstructs the sliding of the sensor 42 further into the housing once the sensor 42 is properly positioned with the contact pads 49 in contact with the conductive contacts 80.

In other embodiments, the conductive contacts 80 are on the exterior of the housing 45 (see e.g., FIGS. 10A-10B and 11A-11E). In these embodiments, the patient guides the contact pads 49 of the sensor 42 into contact with the conductive contacts 80. In some cases, a guiding structure may be provided on the housing 45 which guides the sensor 42 into the proper position. An example of such a structure includes a set of guiding rails extending from the housing 45 and having the shape of the sensor 42.

In some embodiments, when the sensor 42 is inserted using an introducer 120 (see FIG. 3), the tip of the introducer 120 or optional insertion gun 200 (see FIG. 9) is positioned against the skin or the mounting unit 77 at the desired insertion point. In some embodiments, the introducer 120 is positioned on the skin without any guide. In other embodiments, the introducer 120 or insertion gun 200 is positioned using guides (not shown) in the mounting unit 77 or other portion of the on-skin sensor control unit 44. In some embodiments, the guides, opening 79 in the mounting unit 77 and/or sensor port 78 in the housing 45 of the on-skin sensor control unit 44 have a shape which is complementary to the shape of the tip of the introducer 120 and/or insertion gun 200 to limit the orientation of the introducer 120 and/or insertion gun 200 relative to the opening 79 and/or sensor port 78. The sensor can then be subcutaneously inserted into the patient by matching the complementary shape of the opening 79 or sensor port 78 with the introducer 120 and/or insertion gun 200.

In some embodiments, the shapes of a) the guides, opening 79, or sensor port 78, and (b) the introducer 120 or insertion gun 200 are configured such that the two shapes can only be matched in a single orientation. This aids in inserting the sensor 42 in the same orientation each time a new sensor is inserted into the patient. This uniformity in insertion orientation may be required in some embodiments to ensure that the contact pads 49 on the sensor 42 are correctly aligned with appropriate conductive contacts 80 on the on-skin sensor control unit 44. In addition, the use of the insertion gun, as described above, may ensure that the sensor 42 is inserted at a uniform, reproducible depth.

An exemplary on-skin sensor control unit 44 can be prepared and used in the following manner. A mounting unit 77 having adhesive on the bottom is applied to the skin. An insertion gun 200 (see FIG. 9) carrying the sensor 42 and the introducer 120 is positioned against the mounting unit 77. The insertion gun 200 and mounting unit 77 are optionally designed such that there is only one position in which the two properly mate. The insertion gun 200 is activated and a portion of the sensor 42 and optionally a portion of the introducer 120 are driven through the skin into, for example, the subcutaneous tissue. The insertion gun 200 withdraws the introducer 120, leaving the portion of the sensor 42 inserted through the skin. The housing 45 of the on-skin control unit 44 is then coupled to the mounting unit 77. Optionally, the housing 45 and the mounting unit 77 are formed such that there is only one position in which the two properly mate. The mating of the housing 45 and the mounting unit 77 establishes contact between the contact pads 49 (see e.g., FIG. 2) on the sensor 42 and the conductive contacts 80 on the on-skin sensor control unit 44. Optionally, this action activates the on-skin sensor control unit 44 to begin operation.

Figure 12:
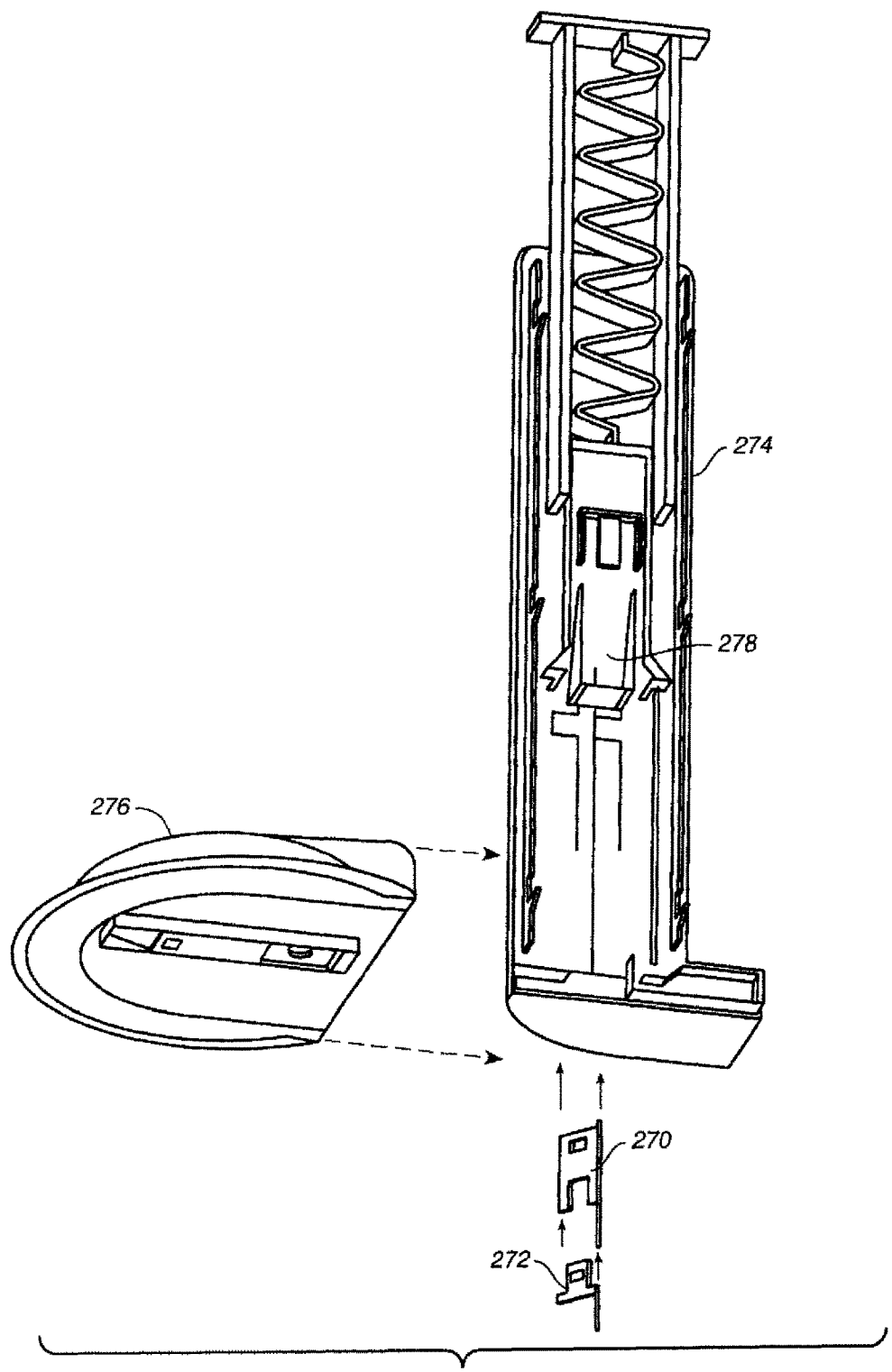
FIG. 12 depicts an introducer, sensor, insertion gun and mounting unit, which can be assembled and sold together in an insertion kit.

The introducer, sensor, insertion gun and mounting unit can be manufactured, marketed, or sold as a unit. For example, FIG. 12 depicts an introducer 270, sensor 272, insertion gun 274 and mounting unit 276, which can be assembled (as indicated by the arrows) and sold together in an insertion kit. In such an embodiment of an insertion kit, the insertion gun 274 can be packaged in a pre-loaded fashion, with an introducer 270 and sensor 272 mated or otherwise coupled, the mated sensor 272 and introducer 270 loaded upon the carrier 278 of the insertion gun, and with a mounting unit 276 already mated with the end of the insertion gun 274.

In one embodiment, the insertion gun 274 is packaged in a state where it is ready to thrust the sensor 272 (and perhaps introducer 270) into subcutaneous tissue. For example, the insertion gun 274 can be packaged in a "cocked" state, such that the thrusting force used to introduce the sensor 272 into the subcutaneous tissue is stored in the device as potential energy (in the case of the embodiment depicted in FIG. 12, the insertion gun 274 would be "cocked" by compressing its spring 280, thus storing potential energy within the coils of the spring). Preferably, an insertion gun 274 packaged in such a manner employs a "safety", a barrier to prevent the release of the stored potential energy. The barrier is removed in order to permit the potential energy to be released. Within the context of the embodiment presented in FIG. 12, an example of a safety is a pin (not pictured) that impedes the spring from expanding, once compressed. Thus, an insertion kit so embodied can be obtained at a place of purchase, removed from its package, and used after removal of the safety, without necessitating additional steps. Alternatively, the insertion gun 274 can be packaged in the above-described pre-loaded configuration, but without being "cocked". Thus, an insertion kit with an "uncocked" insertion gun 274 can be obtained at a place of purchase, removed from its package, cocked, and used. To facilitate the insertion kit being ready to use with minimal user-exercised steps, the insertion kit can be sterilized prior to packaging. Examples of acceptable sterilizing techniques include exposing the elements of the insertion kit to gamma radiation or an e-beam.

Figure 13:
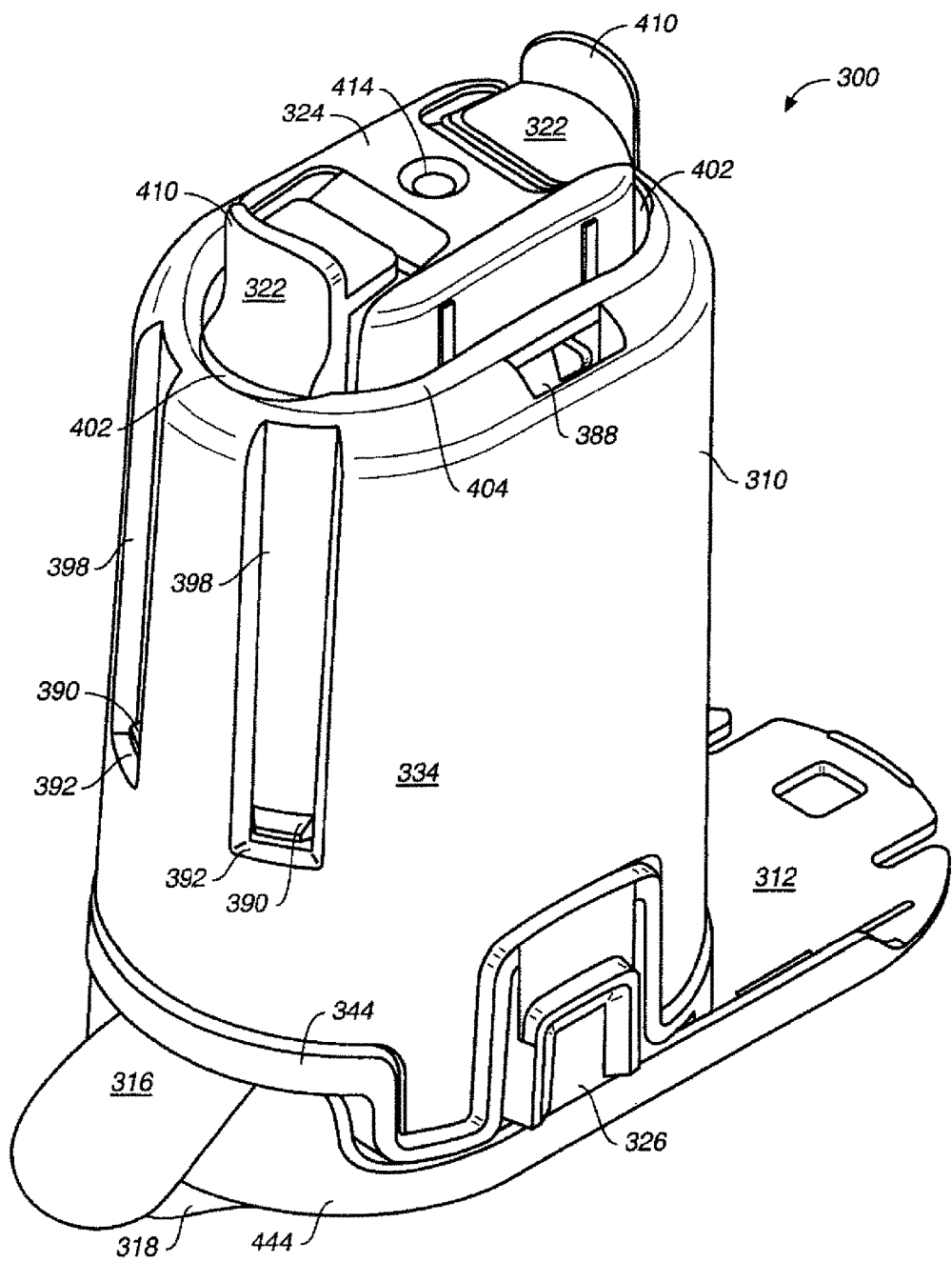
FIG. 13 is a perspective view showing a preferred commercial embodiment of a sensor inserter and adhesive mount constructed according to the invention.

Referring to FIGS. 13-33B, preferred commercial embodiments of a sensor inserter constructed according to the invention will now be described. FIG. 13 shows an overall perspective view of a sensor inserter kit 300 comprising a single-use sensor inserter 310 and a single-use adhesive mount 312 removably attached to the bottom thereof.

As an overview of the operation of inserter kit 300, the kit comes packaged generally as shown in FIG. 13 with a sensor 314 (best seen in FIGS. 16 and 25) preloaded within inserter 310 and with inserter 310 in a "cocked" state. After preparing an insertion site on the skin, typically in the abdominal region, the patient removes upper liner 316 and lower liner 318 from adhesive mount 312 to expose the bottom surface and a portion of the top surface of an adhesive tape 320 (best seen in FIG. 16) located beneath mount 312. Mount 312, with inserter 310 attached, is then applied to the patient's skin at the insertion site. Safety lock tabs 322 are squeezed together to allow actuator button 324 to be pressed causing inserter 310 to fire, thereby inserting sensor 314 into the patient's skin with a predetermined velocity and force. Once sensor 314 has been inserted into the skin, the patient removes inserter 310 from mount 312 by pressing release tabs 326 on opposite sides of inserter 310 and lifting inserter 310 away from mount 312.

Referring to FIG. 14, mount 312 is shown adhered to a patient's skin 328 with sensor 314 already inserted. Once inserter 310 is removed from mount 312, transmitter 330 can be slid into place. The circuitry of transmitter 330 makes electrical contact with the contact pads on sensor 314 after transmitter 330 is fully seated on mount 312. Once initialization and synchronization procedures are completed, electrochemical measurements from sensor 314 can be sent wirelessly from transmitter 330 to a portable receiver 332, as shown in FIG. 15. Sensor 314, mount 312 and transmitter 330 remain in place on the patient for a predetermined period, currently envisioned to be three days. These components are then removed so that sensor 314 and mount 312 can be properly discarded. The entire procedure above can then be repeated with a new inserter 310, sensor 314 and mount 312, reusing transmitter 330 and receiver 332.

Figure 16:
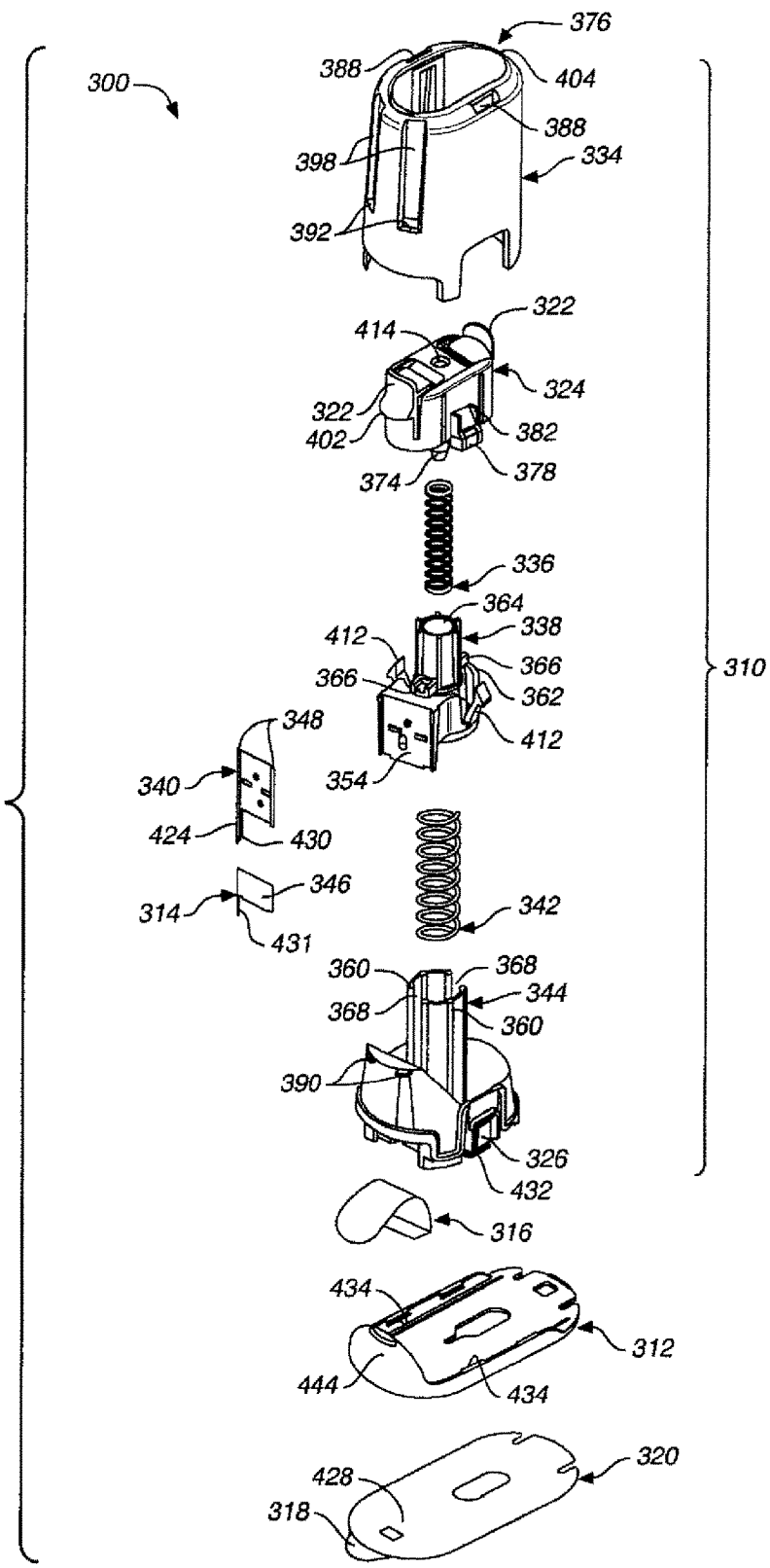
FIG. 16 is an exploded perspective view of the preferred commercial embodiment of FIG. 13.

Referring to FIG. 16, the preferred inserter kit 300 is assembled as shown from the following components: housing 334, actuator button 324, drive spring 336, shuttle 338, introducer sharp 340, sensor 314, retraction spring 342, inserter base 344, upper liner 316, adhesive mount 312, adhesive tape 320, and lower liner 318.

Sensor 314 has a main surface 346 slidably mounted between U-shaped rails 348 of introducer sharp 340 and releasably retained there by sensor dimple 350 which engages introducer dimple 352. Introducer sharp 340 is mounted to face 354 of shuttle 338, such as with adhesive, heat stake or ultrasonic weld. Sensor 314 also has a surface 356 that extends orthogonally from main surface 346 and just beneath a driving surface 358 of shuttle 338 when mounted thereon (details of these features are better shown in FIGS. 19 and 25-27.)

Figure 24:
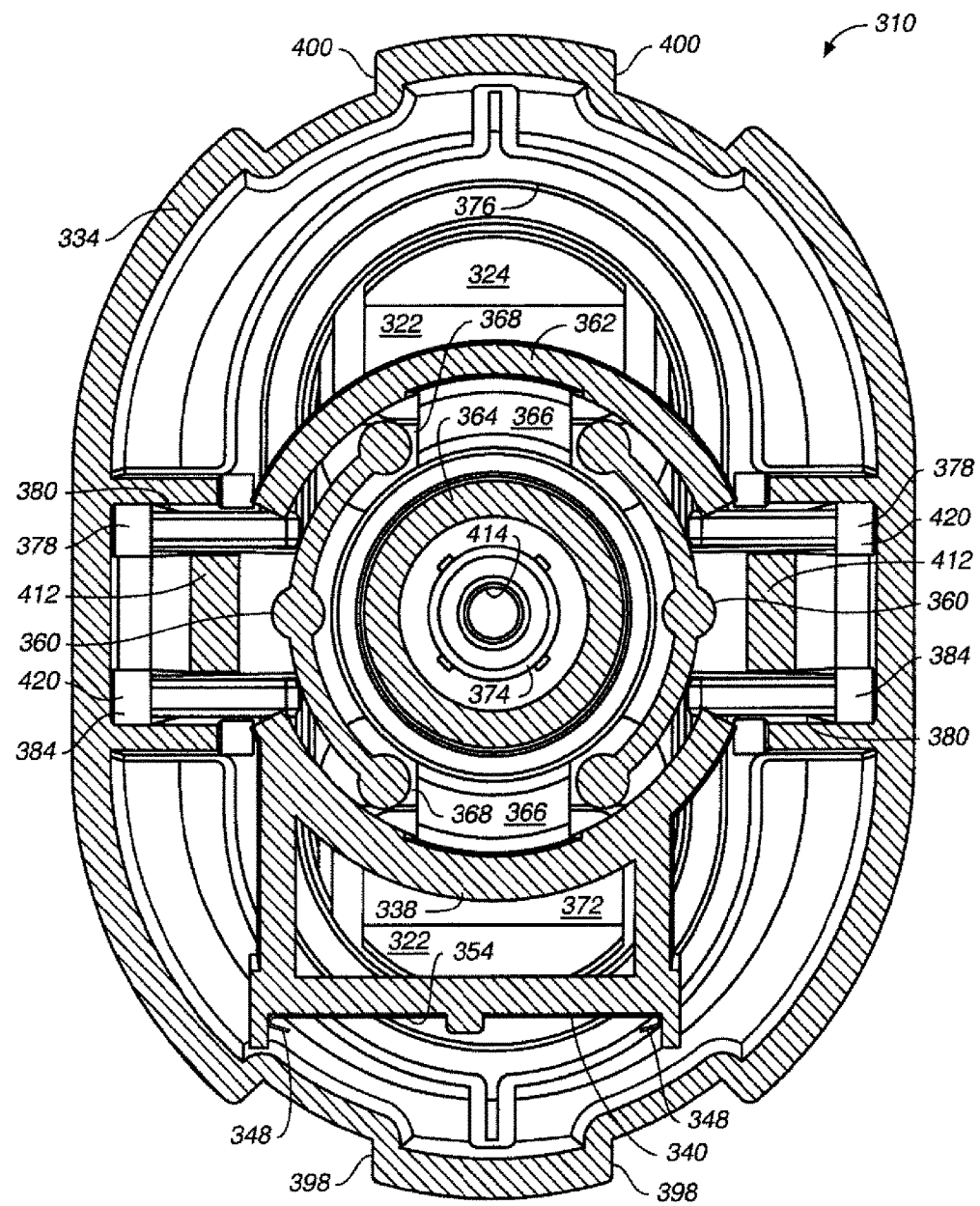
FIG. 24 is a cross-sectional view taken along line 24-24 in FIG. 17.
Figure 25:
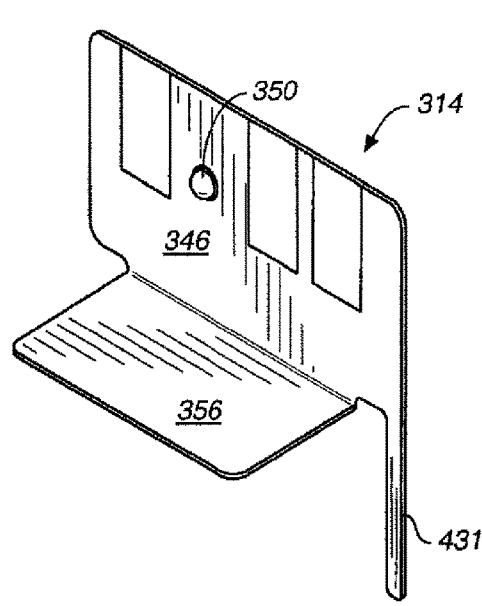
FIG. 25 is a perspective view of a transcutaneously implantable sensor.
Figure 26A:
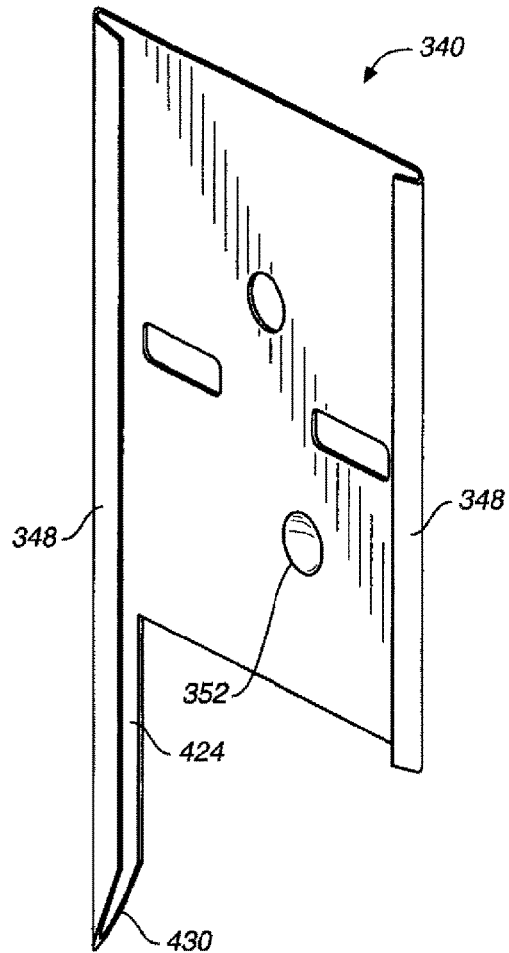
FIG. 26A is a perspective view of a sensor introducer.
Figure 26B:
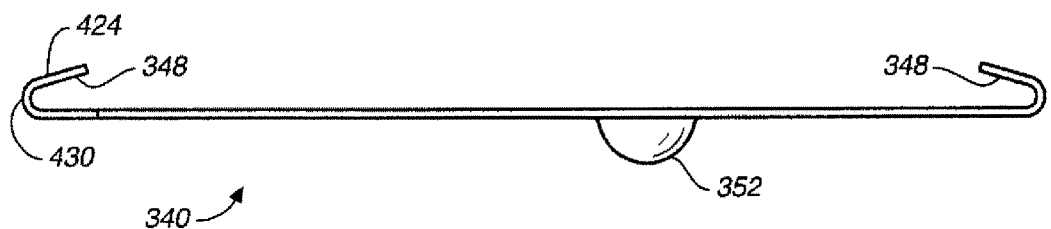
FIG. 26B is a bottom view of the introducer shown in FIG. 26A.
Figure 27:
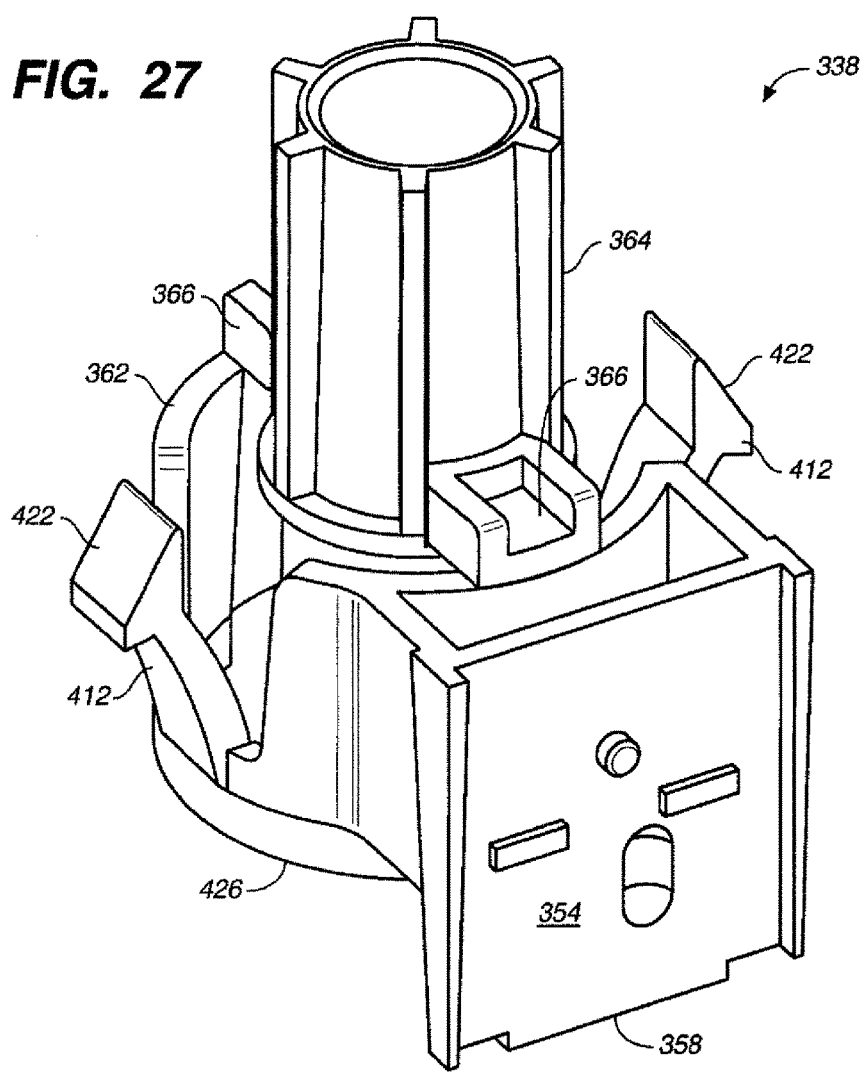
FIG. 27 is a perspective view of a shuttle member.

Shuttle 338 is slidably and non-rotatably constrained on base 344 by arcuate guides 360. As best seen in FIGS. 19, 24 and 27, shuttle 338 is generally formed by an outer ring 362 and an inner cup-shaped post 364 connected by two bridges 366. Bridges 366 slide between the two slots 368 formed between guides 360 and allow shuttle 338 to travel along guides 360 without rotating. Retraction spring 342 is captivated at its outer circumference by guides 360, at its bottom by the floor 370 of base 344, at its top by bridges 366, and at its inner circumference by the outer surface of shuttle post 364. Drive spring 336 is captivated at its bottom and outer circumference by the inside surface of shuttle post 364, at its top by the ceiling 372 inside actuator button 324, and at its inner circumference by stem 374 depending from ceiling 372. When drive spring 336 is compressed between actuator button 324 and shuttle 338 it urges shuttle 338 towards base 344. When retraction spring 342 is compressed between shuttle 338 and base 344, it urges shuttle 338 towards actuator button 324.

Figure 20:
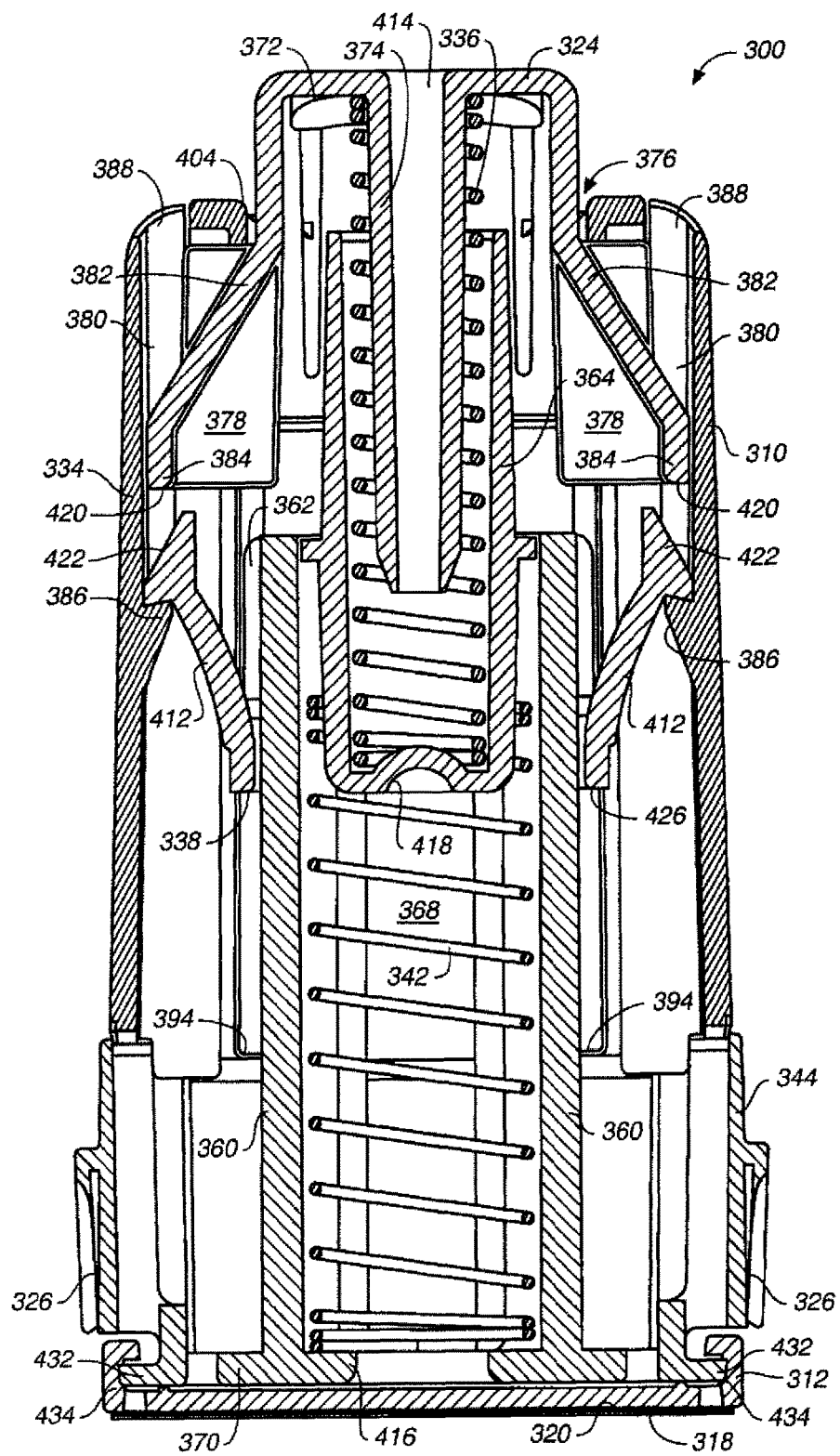
FIG. 20 is a cross-sectional view taken along line 20-20 in FIG. 17.

Actuator button 324 is slidably received within housing 334 from below and resides in opening 376 at the top of housing 334 with limited longitudinal movement. Arms 378 on each side of actuator button 324 travel in channels 380 along the inside walls of housing 334, as best seen in FIG. 20. Longitudinal movement of actuator button 324 is limited in one direction by the base of arms 378 contacting the edge of opening 376 at the top of housing 334, and in the other direction by the distal ends 384 of arms 378 contacting stops 386 in channels 380. Slots 388 are preferably provided in the top of housing 334 for ease of housing manufacture and so tools can be inserted to inwardly compress arms 378 beyond stops 386 to allow actuator button 324 to be removed from housing 334 if needed.

When sensor 314, introducer sharp 340, shuttle 338, retraction spring 342, drive spring 336 and actuator button 324 are assembled between base 344 and housing 334 as shown in FIG. 16 and described above, housing 334 is snapped into place on base 344. Base 344 is held onto housing 334 by upper base barbs 390 that engage upper openings 392 in housing 334, and lower base barbs 394 (best seen in FIG. 17) that engage lower openings 396 in housing 334. Slots 398 and 400 are provided for ease of manufacture of housing 334, and base 344 is preferably removable from housing 334 with tools if needed.

Referring to FIG. 19, actuator button 324 is preferably provided with safety lock tabs 322 hingedly formed on opposite ends. Tabs 322 can be urged from a relaxed outward position to a flexed inward position. When in the normal outward position, shoulders 402 on the outer surfaces of tabs 322 engage the rim 404 of opening 376 to prevent the actuator button 324 from being depressed, thereby avoiding accidental firing of inserter 310. Tabs 322 can be squeezed inward just enough to clear the rim 404 of opening 376 while pressing the actuator button 324 down to fire the inserter. Alternatively, tabs 322 can be squeezed further inward so that barbs 406 on the inside edges can engage catches 408 located on a center portion of actuator button 324, thereby defeating the safety lock to allow later firing by simply pressing down on the actuator button 324. Preferably, upwardly extending grips are provided on tabs 322 for better visual indication of safety lock status and actuation control.

Referring to FIG. 20, shuttle 338 is provided with laterally extending barbed fingers 412 which travel in channels 380 along the inside walls of housing 334. When shuttle 338 is inserted up into housing 334 far enough, barbed fingers 412 momentarily deflect inward and then snap outward again to catch on stops 386. In this "cocked" position as shown, drive spring 336 is compressed and urging shuttle 338 towards base 344, but barbed fingers 412 catching on stops 386 prevent such travel.

Referring to FIGS. 21-23, the sequence of loading, cocking, arming, firing, and automatic retraction of inserter 310 will be described. It is envisioned that in production, inserters 310 will be fabricated and fully assembled by one vender except for sensor 314, which will be supplied and installed by a second vendor in a sterile environment. Accordingly, inserter 310 will be manufactured and shipped to the sensor vendor in a neutral state, as shown in FIG. 21. A hole 414 provided through the center of actuator button 324 allows the sensor vendor to insert a pin (manually or by automated machinery, not shown) through hole 414 to drive shuttle 338 towards base 344 in a controlled fashion and hold it there against the force of retraction spring 342. This will cause introducer sharp 340 to be extended through base 344 (as shown in FIG. 23) so that sensor 314 can be loaded into introducer 340. When the pin is removed, shuttle 338, introducer 340 and sensor 314 will retract to the neutral position. The sensor vendor can then cock the loaded inserter 310 before shipment by pushing another pin (not shown) from the opposite direction through a central hole 416 in base 344 (with mount 312 removed) until the pin contacts dimple 418 formed in the bottom of shuttle 338. By pushing shuttle 338 towards actuator button 324 until barbed fingers 412 clear stops 386, the inserter 310 is cocked (as shown in FIG. 22.)

Referring to FIG. 22, inserter 310 is preferably received by the patient in the cocked position as shown. To use inserter 310, the patient applies mount 312 to the mounting site and disables the safety mechanism as previously described, and then pushes actuator button 324 against the force of drive spring 336. As actuator button 324 travels toward base 344, drive cam surfaces 420 on arms 378 contact ramped surfaces 422 of barbed fingers 412 and urge them inward. When fingers 412 are driven inward enough to clear stops 386, shuttle 338 is driven by drive spring 336 with a predetermined speed and force to an insertion position, as shown in FIG. 23.

Referring to FIG. 23, inserter 310 is shown in the insertion position with the tail 424 of introducer sharp 340 extending through base 344 and mount 312 into the skin of the patient. FIG. 23 shows shuttle 338 in a fully extended position with its lower surface 426 bottomed out on base 344. However, the lower orthogonal surface 356 of sensor 314 will contact an exposed sensor contact portion 428 (best seen in FIG. 16) on top of adhesive tape 320 supported from below by the patient's skin, and therefore will typically stop traveling before reaching the fully bottomed out position shown. Tail 424 of introducer sharp 340 provides rigidity and a skin piercing edge 430 for allowing the flexible tail 431 of sensor 314 to be implanted in the patient's skin. After providing this function, introducer sharp 340 is immediately removed from the patient and retracted into a safe position inside housing 334 as refraction spring 342 (which has been compressed by the travel of the shuttle) pushes shuttle 338 back towards actuator cap. Sensor 314 is pulled from introducer sharp 340 and held in place by the sensor contact portion 428 on top of adhesive tape 320 adhering to orthogonal surface 356 of sensor 314. The geometries of sensor dimple 350 and mating introducer dimple 352 are chosen to create a separation force between them that is less than the adhesion force of tape 320 on orthogonal surface 356, but great enough to retain sensor 314 in introducer sharp 340 during typical shipping and product handling shock loads. Driving surface 358 beneath shuttle 338 presses down on top of orthogonal surface 356 to ensure good contact with adhesive tape 320 before shuttle 338 retracts with introducer sharp 340. As discussed above with previous embodiments, barb(s) on sensor tail 431 can be employed to further anchor the sensor in its operating position.

Referring again to FIG. 21, retraction spring 342 will return shuttle 338 to the neutral position as shown after firing, but without sensor 314 which remains inserted in patient's skin (not still in introducer sharp 340 as shown). Drive spring 336 is preferably designed to be stiffer than retraction spring 342 so that shuttle 338 oscillations are quickly dampened out, and so introducer sharp 340 does not return to sensor 314 or the patient to cause injury. With sensor 314 now inserted in the patient's skin, inserter 310 can be removed from mount 312 by inwardly flexing release tabs 326 on opposite sides of inserter 310 to remove latch hooks 432 from mount channels 434 and then lifting inserter 310 away from mount 312. Introducer sharp 340 remains protected inside housing 334 during disposal of inserter 310. Transmitter 330 can now be slid into place on mount 312 as previously described.

Figure 28:
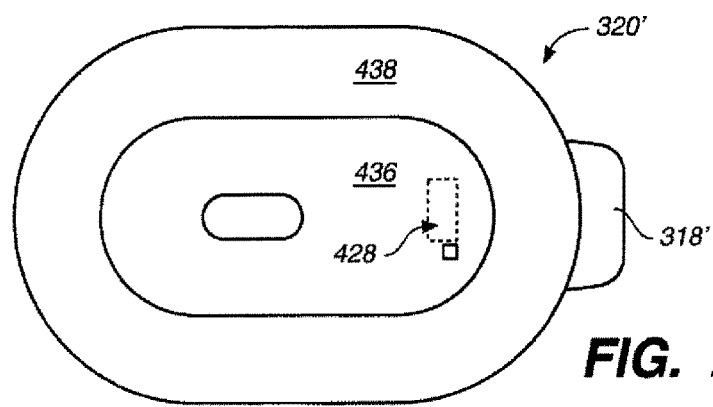
FIG. 28 is a top plan view of an oversized adhesive tape.

Referring to FIG. 28, an alternative embodiment of adhesive tape 320' is shown. This oversized tape 320' has the advantage of holding transmitter 330 in place even when fairly large forces are placed on it. In this embodiment adhesive tape 320' has a double-sided portion 436 (adhesive on both top and bottom sides) residing between mount 312 and the patient's skin, and a single-sided portion 438 outwardly extending from the double-sided portion 436, preferably in all directions, for adhering just to the patient's skin. In the previous embodiment, it is difficult to separate mount 312 from the skin merely with tension forces, but applying a force to just one side of mount 312 results in a high peeling force being applied to that edge of the adhesive tape 320 which causes tape 320 to peel off of the skin. In contrast, any force applied to transmitter 330 in this alternative embodiment results in a tension force rather than a peeling force being applied to tape 320', inhibiting inadvertent removal until an edge of tape 320' is intentionally peeled up. Preferably, single-sided portion 438 has a width roughly double the width of double-sided portion 436. In the preferred embodiment, theses widths are 2.14 and 1.14 inches, respectively. Preferably, the length that single-sided portion 438 extends beyond double-sided portion 436 is roughly equivalent to the combined height of transmitter 330 attached to mount 312, in this case about 0.5 inches.

In the preferred embodiment, sensor 314 is made from a 0.005 inch thick Mylar® substrate, such as Dupont Melinex ST-505, print treated both sides, heat stabilized and bi-axially oriented. Main surface 346 is 0.315 tall by 0.512 wide, and orthogonal surface 356 is 0.374 wide by 0.202 deep. Sensor tail 431 is 0.230 long by 0.023 wide. Semispherical sensor dimple 350 is 0.050 inches wide and 0.026 inches deep. Introducer sharp 340 is made from SUS 301 medical grade stainless steel, 0.004 inches thick, having a surface roughness less than or equal to 0.5 micrometers. The height of the main portion of introducer sharp 340 is 0.614 inches, and the inside width is 0.513 inches. The overall thickness of rolled rails 348 is 0.026 inches. The length and width of introducer tail 424 are 0.354 and 0.036 inches, respectively. The preferred angle of the introducer sharp 340 is 21 degrees. Preferably, semispherical introducer dimple 352 has a radius of 0.024 inches. In the preferred embodiment, shuttle 338 has an average speed of at least 1 meter/second, and has a momentum at its end of travel of about 2.65 lb-m/sec.

Preferably, housing 334, button 324, shuttle 338, base 344 and mount 312 are all injection molded from G.E. Lexan PC. Inside and outside working surfaces of arms 378 on button 324 are preferably lubricated with Dow Corning 360 Medical Fluid. Drive spring 336 has a free length of 1.25 inches, a working length of 1.00 inch, and a rate between 20 and 30 pounds per inch. Retraction spring 342 has a free length of 1.5 inches, a working length of 0.35 inches, and a rate between 0.15 and 0.35 pounds per inch. Adhesive tape 320 preferably is medical grade acrylic adhesive on polyester film (such as Acutek 0396013) with a semi-bleached kraft liner having silicon release.

Figure 29:
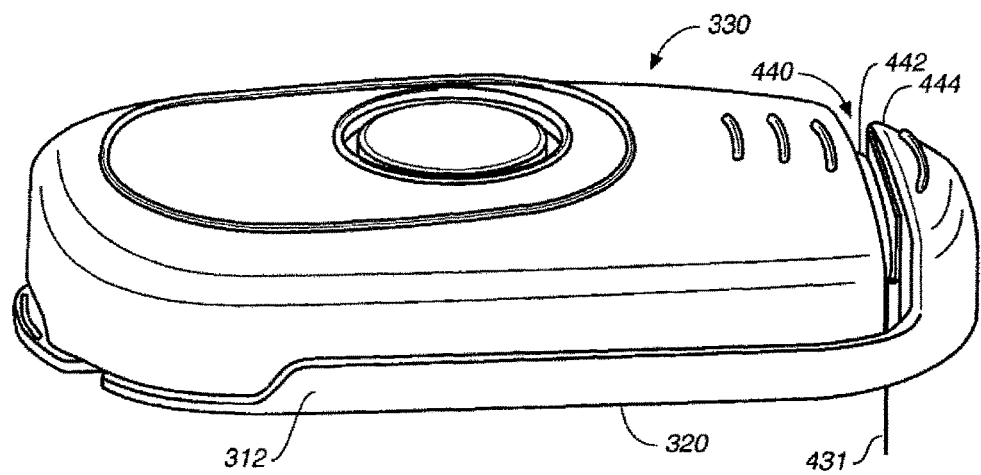
FIG. 29 is a perspective view of the transmitter attached to the adhesive mount and showing the sensor sandwiched therebetween.

Referring to FIG. 29, an interconnect 440 is shown for providing waterproof electrical connections between sensor 314 and transmitter 330. Interconnect 440 includes a seal 442 mounted on an end of transmitter 330 that contacts one side of sensor 314 when transmitter 330 is slid onto mount 312. When transmitter 330 is locked into place on mount 312, seal 442 is compressed between transmitter 330 and sensor 314 and urges sensor 314 against raised end stop 444 of mount 312.

Figure 30:
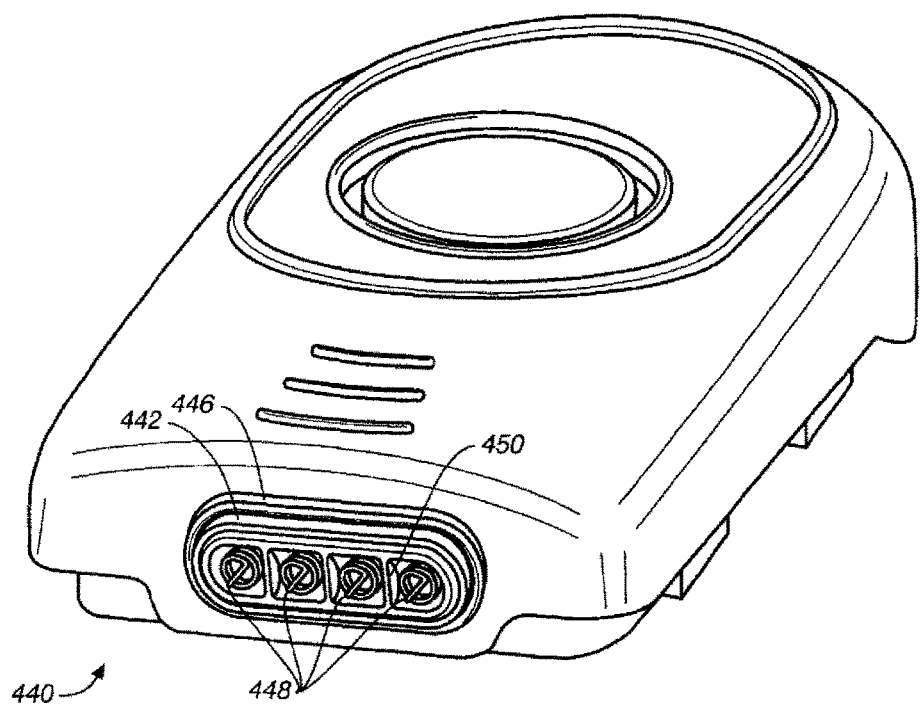
FIG. 30 is a perspective view of the interconnect on one end of the transmitter.

Referring to FIG. 30, further details of interconnect 440 are shown. Seal 442 has an exterior wall 446 for surrounding electrical contacts 448 (in this case four), and interior walls 450 for isolating electrical contacts 448 from each other. Rim 452 formed on the transmitter housing 330 surrounds the base 454 of seal 442 to prevent it from collapsing outward when compressed (see FIGS. 31-32).

Figure 31:
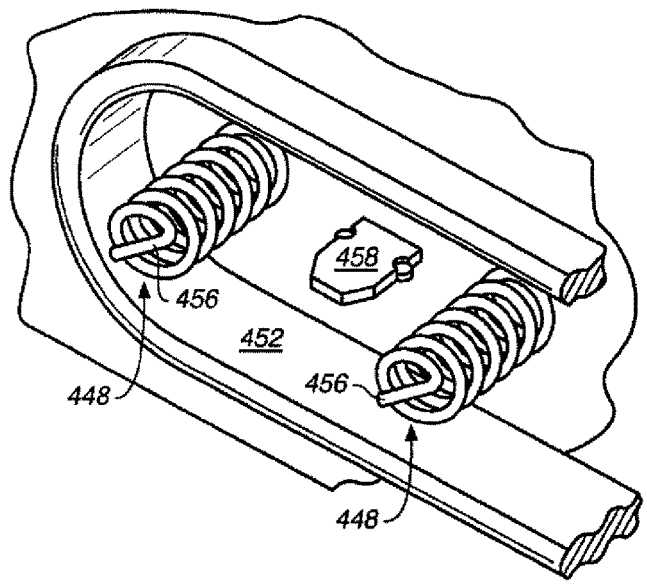
FIG. 31 is an enlarged perspective view of the interconnect of FIG. 30 with the seal and one spring removed for clarity.

Referring to FIG. 31, an enlarged partial view of FIG. 30 is shown with seal 442 and one spring removed for clarity. Electrical contacts 448 are preferably constructed from compression springs 456 mounted on connector lugs 458. Lugs 458 are stamped rearward on their edges to form protrusions that retain springs 456. Alternately or in conjunction with this stamping, plastic rings (not shown) can be melted over the base of each spring 456 for attaching it to its respective lug 458. Connector lugs 458 can protrude through slots in transmitter 330, or be insert molded integral with the plastic housing when it is molded.

Figure 32:
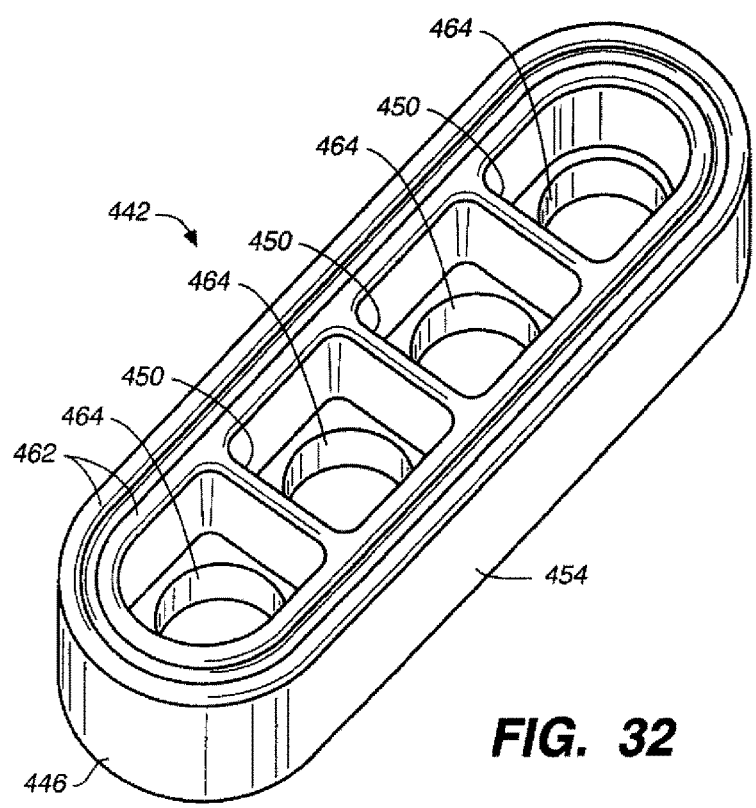
FIG. 32 is an enlarged perspective view of the interconnect seal.

Referring to FIG. 32, an enlarged perspective view of the seal 442 is shown. It has been discovered through experimentation that two lips 462 of equal height along the distal edge of exterior wall 446 provide the best seal from exterior elements. Good isolation between electrical contacts 448 is best achieved by having interior walls 450 with a height equal to that of lips 462. Recesses 464 should be sized large enough so that seal 442 does not interfere with the movement of springs 456 when seal 442 and springs 456 are compressed. In the preferred embodiment, the distal face of seal 442 defined by lips 462 is formed at a 1 degree angle to match the draft angle of mount end stop 444.

Seal 442 is preferably made of shore A 30 durometer compression molded silicone. It is envisioned that seal 442 can be shortened in the axial direction (parallel to springs 456) to reduce the force required to compress it when attaching transmitter 330 to mount 312. Best results for fastening seal 442 to transmitter 330 have been achieved with double sided adhesive tape 320, silicone adhesive on one side and acrylic adhesive on the other for sticking to the PC-ABS blend of the transmitter 330, such as product number 9731 manufactured by 3M Company of St. Paul, Minn. Springs 456 are preferably made from gold-plated beryllium copper so as to deter galvanic current effects. Preferably, main surface 346 of sensor 314 that contacts seal 442 has a uniform thickness dielectric coating with a window in it (i.e. no dielectric) where springs 456 contact sensor 314. An interconnect 440 constructed as described above remains water proof when submerged to a depth of at least 1 meter for 45 minutes.

To increase the reliability of sensor insertion, the following enhancements can be added to the inserter kit 300 described above. First, a sensor flap can be formed along the top edge of sensor 314. When sensor 314 reaches the extended, delivered position as shown in FIG. 23, the flap catches on the bottom edge of base 344 to ensure that sensor 314 separates from introducer sharp 340 as shuttle 338 returns upward to the retracted position. Adhesive can also be located on the bottom of orthogonal sensor surface 356 to ensure that sensor 314 adheres to the sensor contact portion 428 on the top of adhesive mount tape 320, as shown in FIG. 16.

Figure 33A:
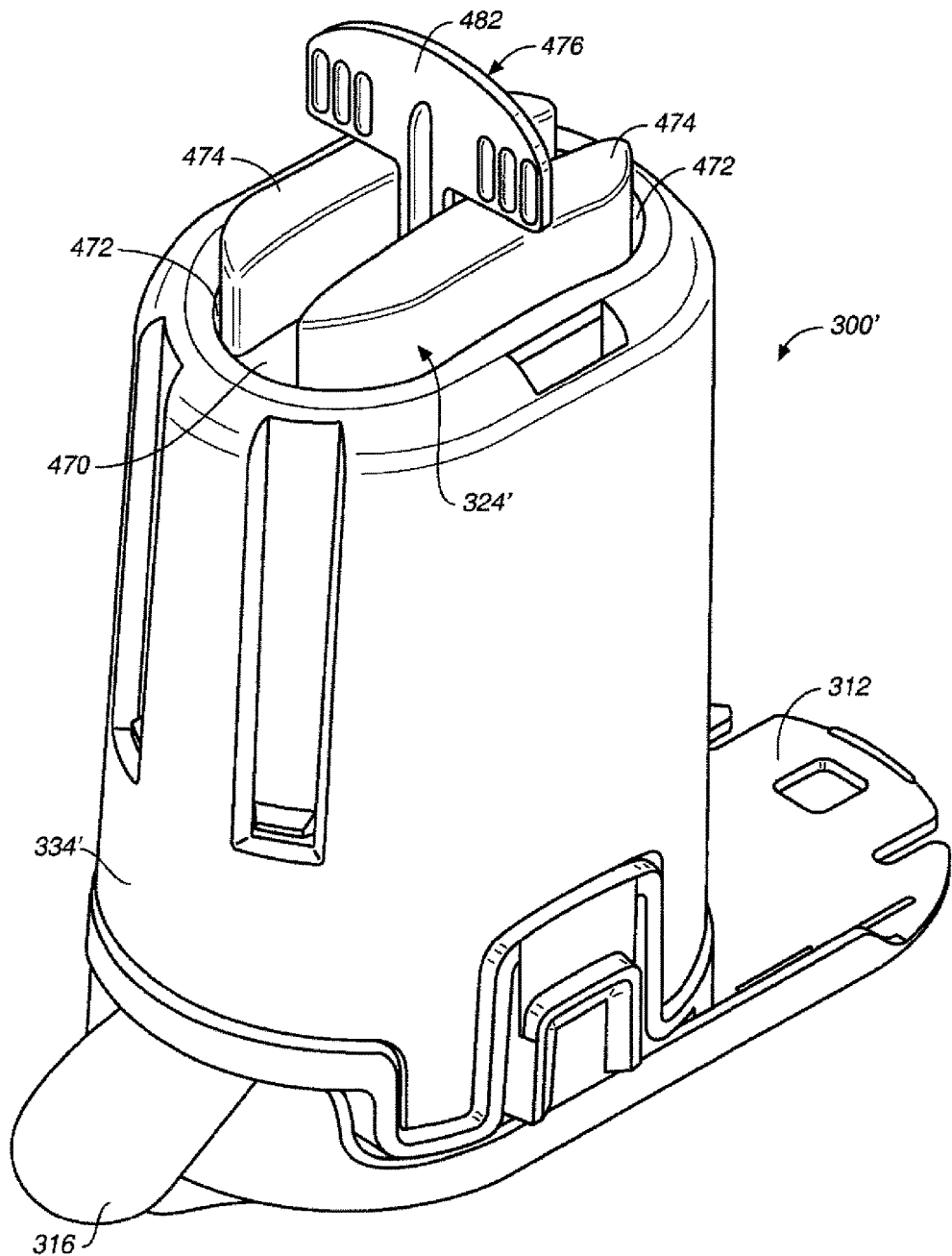
FIG. 33A is a perspective view of an alternative embodiment of a sensor inserter kit.

Referring to FIGS. 33A and 33B, actuator button 324' can be made easier for elderly patients to push by anchoring the upper end of drive spring 336 on a housing bridge 470 instead of button 324. This change also makes the insertion force of inserter 310 more consistent, and allows stronger spring forces to be used if desired. Bridge 470 spans across opening 376' and divides it into two openings 472 in the top of housing 334'. The top portion of button 324' is bifurcated into two protrusions 474 that each extend through an opening 472. A clearance hole (not shown) is provided through the center of button 324' to allow drive spring 336 to pass through and secure around a post (not shown) depending from the bottom center of bridge 470.

Safety lock key 476 can be provided to prevent actuator button 324' from being pressed until key 476 is removed. Aperture 478 is provided in the top center of bridge 470 for receiving boss 480 located at the bottom of key 476, thereby allowing key 476 to rotate. When key handle 482 is rotated perpendicular to button protrusions 474 as shown, two opposing perpendicular fins 484 on key 476 swing into inwardly facing slots (not shown) on the inside of protrusions 474 and prevent button 324' from being actuated. When key handle 482 and fins 484 are rotated parallel to button protrusions 474 such that fins 484 disengage therefrom, key 476 can be removed and button 324' can then be actuated. Other than these modifications, this inserter kit 300' functions the same as the embodiment previously described.

To provide an easier and more consistent release of shuttle 338 by actuator button 324 or 324', it is envisioned that less aggressive finger engagement with stops 386 can be employed, or the above designs can be modified to have a single, more centrally located shuttle release finger (not shown) instead of the two outboard fingers 412 shown.

The present invention should not be considered limited to the particular examples described above. Various modifications, equivalent processes, as well as numerous structures to which the present invention may be applicable and which fall within the general scope of the invention will be readily apparent to those of skill in the art to which the present invention is directed upon review of the instant specification.

What is claimed is:

1. An assembly, comprising:
   a mount configured for positioning on a skin surface;
   a sensor comprising a proximal portion and a distal portion, wherein the distal portion of the sensor is configured to be transcutaneously positioned in contact with interstitial fluid;
   an introducer configured to engage with the sensor for transcutaneous positioning of the sensor and comprising a proximal portion and a distal portion, wherein the distal portion of the introducer is configured to pierce through the skin surface; and
   a sensor inserter housing configured to be detachably coupleable to the mount to form a sensor insertion assembly, wherein the sensor inserter housing is configured to decouple from the mount when opposing forces are applied to engaging members on opposing sides of the sensor insertion assembly; and
   an actuator coupled to the introducer and configured to move the sensor and introducer in an insertion direction to an extended position in which at least part of the introducer and the sensor protrude from the housing to pierce through the skin surface prior to reaching the extended position, wherein a position of the mount is configured to be fixed relative to the sensor inserter housing when the introducer and the sensor move in the insertion direction to the extended position.

2. The assembly of claim 1, wherein the sensor inserter housing is configured to decouple from the mount after the distal portion of the sensor is transcutaneously positioned under the skin surface in contact with the interstitial fluid.

3. The assembly of claim 1, wherein the sensor is configured to be released from the introducer when the introducer moves in a retraction direction from the extended position to a retracted position.

4. The assembly of claim 3, wherein the introducer is configured to be retained entirely within the sensor inserter housing and physically separated from the sensor when in the retracted position.

5. The assembly of claim 3, wherein the sensor inserter housing is configured to decouple from the mount when the introducer is at the retracted position within the housing and separated from the sensor.

6. The assembly of claim 3, wherein the actuator is axially aligned with the sensor and the introducer along the insertion and retraction directions.

7. The assembly of claim 1, wherein the actuator includes a manual actuator configured to apply a manual force to move the introducer in the insertion direction.

8. The assembly of claim 1, wherein the mount is configured for positioning on the skin surface prior to moving the sensor and the introducer to the extended position.

9. The assembly of claim 1, wherein the mount is coupled to the sensor inserter housing prior to moving the sensor and the introducer to the extended position.

10. The assembly of claim 1, wherein the sensor insertion assembly includes one or more latch hooks coupled to one or more channels.

11. The assembly of claim 10, wherein the one or more latch hooks decouple from the one or more channels when the opposing forces are applied to the engaging members of the sensor insertion assembly.

12. The assembly of claim 1, wherein the introducer is configured to slidably receive the sensor therein.

13. The assembly of claim 1, wherein the distal portion of the introducer defines a skin-piercing edge.

14. The assembly of claim 1, wherein the introducer comprises stainless steel.

15. The assembly of claim 1, wherein the mount is configured to remain positioned on the skin surface after the sensor inserter housing is decoupled from the mount.

16. The assembly of claim 1, wherein the mount includes an adhesive layer configured to adhere to the skin surface.

17. The assembly of claim 1, further including a safety mechanism configured for detachably coupling to the actuator prior to moving the sensor and introducer in the insertion direction to the extended position.

18. An assembly, comprising:
    a mount configured for positioning on a skin surface;
    a sensor comprising a proximal portion and a distal portion, wherein the distal portion of the sensor is configured to be transcutaneously positioned in contact with interstitial fluid;
    an introducer configured to engage with the sensor for transcutaneous positioning of the sensor and comprising a proximal portion and a distal portion, wherein the distal portion of the introducer is configured to pierce through the skin surface; and
    a sensor inserter housing configured to be detachably coupleable to the mount to form a sensor insertion assembly, wherein the sensor inserter housing is configured to decouple from the mount when opposing forces are applied to engaging members on opposing sides of the sensor insertion assembly; and
    an actuator coupled to the introducer and configured to move the sensor and introducer in an insertion direction to an extended position in which at least part of the introducer and the sensor protrude from the housing to pierce through the skin surface prior to reaching the extended position, wherein the mount is configured for positioning on the skin surface prior to moving the sensor and the introducer to the extended position.

19. The assembly of claim 18, wherein the sensor inserter housing is configured to decouple from the mount after the distal portion of the sensor is transcutaneously positioned under the skin surface in contact with the interstitial fluid.

20. The assembly of claim 18, wherein a position of the mount is configured to be fixed relative to the sensor inserter housing when the introducer and the sensor move in the insertion direction to the extended position.

21. The assembly of claim 20, wherein the sensor is configured to be released from the introducer when the introducer moves in a retraction direction from the extended position to a retracted position.

22. The assembly of claim 21, wherein the introducer is configured to be retained entirely within the sensor inserter housing and physically separated from the sensor when in the retracted position.

23. The assembly of claim 21, wherein the actuator is axially aligned with the sensor and the introducer along the insertion and retraction directions.

24. The assembly of claim 18, wherein the actuator includes a manual actuator configured to apply a manual force to move the introducer in the insertion direction.

25. The assembly of claim 24, wherein the sensor inserter housing is configured to decouple from the mount when the introducer is at the retracted position within the housing and separated from the sensor.

26. The assembly of claim 18, wherein the mount is coupled to the sensor inserter housing prior to moving the sensor and the introducer to the extended position.

27. The assembly of claim 18, wherein the sensor insertion assembly includes one or more latch hooks coupled to one or more channels.

28. The assembly of claim 27, wherein the one or more latch hooks decouple from the one or more channels when the opposing forces are applied to the engaging members of the sensor insertion assembly.

29. The assembly of claim 18, wherein the introducer is configured to slidably receive the sensor therein.

30. The assembly of claim 18, wherein the distal portion of the introducer defines a skin-piercing edge.

31. The assembly of claim 18, wherein the introducer comprises stainless steel.

32. The assembly of claim 18, wherein the mount is configured to remain positioned on the skin surface after the sensor inserter housing is decoupled from the mount.

33. The assembly of claim 18, wherein the mount includes an adhesive layer configured to adhere to the skin surface.

34. The assembly of claim 18, further including a safety mechanism configured for detachably coupling to the actuator prior to moving the sensor and introducer in the insertion direction to the extended position.

* * * * *